United States Patent
Narine et al.

(10) Patent No.: US 11,570,992 B2
(45) Date of Patent: Feb. 7, 2023

(54) BICYCLIC COMPOUNDS

(71) Applicant: BASF SE, Ludwigshafen am Rhein (DE)

(72) Inventors: Arun Narine, Ludwigshafen (DE); Ashokkumar Adisechan, Navi Mumbai (IN); Rupsha Chaudhuri, Navi Mumbai (IN); Gopal Krishna Datta, Goettingen (DE); Sunderraman Sambasivan, Navi Mumbai (IN); Devendra Vyas, Navi Mumbai (IN)

(73) Assignee: BASF SE, Ludwigshafen (DE)

( * ) Notice: Subject to any disclaimer, the term of this patent is extended or adjusted under 35 U.S.C. 154(b) by 443 days.

(21) Appl. No.: 16/089,732

(22) PCT Filed: Mar. 29, 2017

(86) PCT No.: PCT/EP2017/057464
§ 371 (c)(1),
(2) Date: Sep. 28, 2018

(87) PCT Pub. No.: WO2017/167832
PCT Pub. Date: Oct. 5, 2017

(65) Prior Publication Data
US 2019/0104738 A1   Apr. 11, 2019

(30) Foreign Application Priority Data
Apr. 1, 2016   (IN) .............................. 201621011658

(51) Int. Cl.
*A01N 43/90* (2006.01)
*C07D 487/04* (2006.01)
*A01P 7/04* (2006.01)
*C07D 471/04* (2006.01)

(52) U.S. Cl.
CPC ................ *A01N 43/90* (2013.01); *A01P 7/04* (2021.08); *C07D 471/04* (2013.01); *C07D 487/04* (2013.01)

(58) Field of Classification Search
None
See application file for complete search history.

(56) References Cited

U.S. PATENT DOCUMENTS

| | | | |
|---|---|---|---|
| 9,120,792 B2 | 9/2015 | Nokura et al. | |
| 9,549,559 B2 | 1/2017 | Shimizu et al. | |
| 9,974,307 B2 | 5/2018 | Shimizu et al. | |
| 10,435,374 B2 | 10/2019 | Heilmann et al. | |
| 2005/0256000 A1 | 11/2005 | Schaper et al. | |
| 2006/0199801 A1 | 9/2006 | i Blasco et al. | |
| 2010/0113441 A1 | 5/2010 | Siegel et al. | |

FOREIGN PATENT DOCUMENTS

| | | |
|---|---|---|
| CN | 105101800 A | 11/2015 |
| EP | 1620436 A1 | 2/2006 |
| EP | 1746880 A1 | 1/2007 |
| EP | 1783114 A1 | 5/2007 |
| EP | 2831076 B1 | 5/2016 |
| WO | WO-2009/099736 A2 | 8/2009 |
| WO | WO-2011/138427 A2 | 11/2011 |
| WO | 12086848 A1 | 6/2012 |
| WO | WO-2013/018928 A1 | 2/2013 |
| WO | 13144088 A1 | 10/2013 |
| WO | 13180193 A1 | 12/2013 |
| WO | 14119670 A1 | 8/2014 |
| WO | WO-2014/119672 A1 | 8/2014 |
| WO | 15038503 A1 | 3/2015 |
| WO | 16023954 A2 | 2/2016 |
| WO | 16055431 A1 | 4/2016 |
| WO | 16071499 A1 | 5/2016 |
| WO | 16102488 A1 | 6/2016 |
| WO | 17045955 A1 | 3/2017 |

OTHER PUBLICATIONS

International Search Report, issued in PCT/EP2017/057464, dated May 11, 2017.
International Preliminary Reporton Patentability, issued in PCT/EP2017/057464, dated Oct. 2, 2018.

*Primary Examiner* — John Pak
(74) *Attorney, Agent, or Firm* — Marshall, Gerstein & Borun LLP

(57) ABSTRACT

The present invention relates to compounds of formula I,

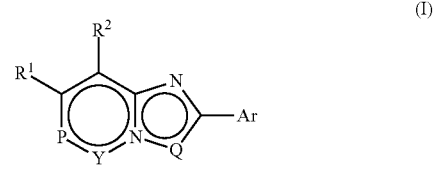

wherein the variables are defined as given in the description and claims. The invention further relates to uses, processes and composition for compounds I.

24 Claims, No Drawings

BICYCLIC COMPOUNDS

This application is a National Stage application of International Application No. PCT/EP2017/057464, filed Mar. 29, 2017. This application also claims priority under 35 U.S.C. § 119 to Indian Patent Application No. 201621011658, filed Apr. 1, 2016.

The present invention relates to substituted bicyclic compounds of formula I as agrochemical pesticides. Furthermore, the present invention relates to processes and intermediates for preparing compounds of formula I and to active compound combinations comprising them. Moreover, the present invention relates to agricultural or veterinary compositions comprising the compounds of formula I, and to the use of the compounds of formula I or compositions comprising them for combating or controlling invertebrate pests and/or for protecting crops, plants, plant propagation material and/or growing plants from attack and/or infestation by invertebrate pests. The present invention also relates to methods of applying the compounds of formula I. Furthermore, the present invention relates to seed comprising compounds according to the invention. Invertebrate pests and in particular insects, arachnids and nematodes destroy growing and harvested crops and attack wooden dwelling and commercial structures, thereby causing large economic loss to the food supply and to property. Accordingly, there is an ongoing need for new agents for combating invertebrate pests.

5,6-fused heterocycles are known for pesticidal use, for example, in patent publications WO 2012/086848, WO 2013/1 801 93 and WO 2014/119670 and represent an important class of insecticide. Imidazopyridinones have been found to be pesticidally active. In this regard, reference is, made to publication WO 2016/023954.

Due to the ability of target pests to develop resistance to pesticidally-active agents, there is an ongoing need to identify further compounds, which are suitable for combating invertebrate pests such as insects, arachnids and nematodes. Furthermore, there is a need for new compounds having a high pesticidal activity and showing a broad activity spectrum against a large number of different invertebrate pests, especially against difficult to control insects, arachnids and nematodes.

It is therefore an object of the present invention to identify and provide compounds, which exhibit a high pesticidal activity and have a broad activity spectrum against invertebrate pests.

It has been found that these objects can be achieved by substituted bicyclic compounds of formula I, as depicted and defined below, including their stereoisomers, their salts, in particular their agriculturally or veterinarily acceptable salts, their tautomers and their N-oxides.

In a first aspect, the present invention relates to the bicyclic compound of formula I,

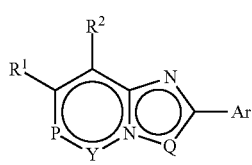

(I)

wherein
the circle in ring represents that ring is fully unsaturated;
Y is C=X, wherein X is O or S;
P is N($R^x$) or C($R^3$);
Q is N($R^y$) or C($R^4$);
provided that if P is N($R^x$), Q is C($R^4$) and if P is C($R^3$), Q is N($R^y$);
$R^x$, $R^y$ independently of each other are selected from the group consisting of $C_1$-$C_6$-alkyl $C_1$-$C_6$-alkoxy, $C_2$-$C_6$-alkenyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which are unsubstituted or substituted by halogen, C(O)—OR$^a$, NR$^b$R$^c$, $C_1$-$C_6$-alkylen-NR$^b$R$^c$, O—$C_1$-$C_6$-alkylen-NR$^b$R$^c$, $C_1$-$C_6$-alkylen-CN, NH—$C_1$-$C_6$-alkylen-NR$^b$R$^c$, C(O)—NR$^b$R$^c$, C(O)—R$^d$, SO$_2$NR$^b$R$^c$, S(=O)$_m$R$^e$, phenyl and benzyl, wherein the phenyl ring is unsubstituted or substituted by radicals R$^f$;
$R^1$ is $C_1$-$C_6$-alkyl, $C_2$-$C_6$-alkoxy, $C_2$-$C_6$-alkenyl, $C_2$-$C_6$-alkynyl, $C_3$-$C_6$-cycloalkyl, $C_3$-$C_6$-cycloalkoxy, $C_1$-$C_6$-sulfenyl, $C_1$-$C_6$-sulfinyl, or $C_1$-$C_6$-sulfonyl wherein each of the aforementioned radicals are partially or fully halogenated;
$R^2$, $R^3$, $R^4$ independently of each other are selected from the group consisting of H, halogen, N$_3$, CN, NO$_2$, —SCN, —SF$_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxyx-$C_1$-$C_4$-alkyl, which are unsubstituted or substituted by halogen, C(O)—OR$^a$, NR$^b$R$^c$, $C_1$-$C_6$-alkylen-NR$^b$R$^c$, O—$C_1$-$C_6$-alkylen-NR$^b$R$^c$, $C_1$-$C_6$-alkylen-CN, NH—$C_1$-$C_6$-alkylen-NR$^b$R$^c$, C(O)—NR$^b$R$^c$, C(O)—R$^d$, SO$_2$NR$^b$R$^c$ and S(=O)$_m$R$^e$, one radical may also be phenyl, phenoxy, phenylcarbonyl, phenylthio or benzyl, wherein the phenyl ring is unsubstituted or substituted by radicals R$^f$;
Ar is phenyl or 5- or 6-membered heteroaryl, which are unsubstituted or substituted by radicals R$^{Ar}$, which are identical or different, wherein
$R^{Ar}$ independently of each other, are selected from the group consisting of halogen, N$_3$, OH, CN, NO$_2$, —SCN, —SF$_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, which are unsubstituted or substituted by halogen, C(O)—OR$^a$, NR$^b$R$^c$, $C_1$-$C_6$-alkylen-NR$^b$R$^c$, O—$C_1$-$C_6$-alkylen-NR$^b$R$^c$, $C_1$-$C_6$-alkylen-CN, NH—$C_1$-$C_6$-alkylen-NR$^b$R$^c$, C(O)—NR$^b$R$^c$, C(O)—R$^d$, SO$_2$NR$^b$R$^c$ and S(=O)$_m$R$^e$, one radical may also be phenyl, phenoxy, phenylcarbonyl, phenylthio or benzyl, wherein the phenyl ring is unsubstituted or substituted by radicals R$^f$;
each $R^a$ is selected from H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which are unsubstituted or substituted by halogen, $C_1$-$C_6$-alkylen-NR$^b$R$^c$, $C_1$-$C_6$-alkylen-CN, phenyl and benzyl, wherein the phenyl ring is unsubstituted or substituted by radicals R$^f$;
each $R^b$ is selected from H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which are unsubstituted or substituted by halogen, $C_1$-$C_6$-alkylen-CN, phenyl and benzyl, wherein the phenyl is unsubstituted or substituted by radicals $R^f$;

each $R^c$ is selected from H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which are unsubstituted or substituted by halogen, $C_1$-$C_6$-alkylen-CN, phenyl and benzyl, wherein the phenyl ring is unsubstituted or substituted by radicals $R^f$;

each moiety $NR^bR^c$ may also form an N-bound, saturated 5- to 8-membered heterocycle, which in addition to the nitrogen atom may have 1 or 2 further heteroatoms or heteroatom moieties selected from O, $S(=O)_m$ and N—$R'$, wherein $R^1$ is H or $C_1$-$C_6$-alkyl and wherein the N-bound heterocycle is unsubstituted or substituted by radicals selected from halogen, $C_1$-$C_4$-alkyl, $C_1$-$C_4$-haloalkyl, $C_1$-$C_4$-alkoxy and $C_1$-$C_4$-haloalkoxy;

each $R^d$ is selected from H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which are unsubstituted or substituted by halogen, phenyl and benzyl, wherein the phenyl ring is unsubstituted or substituted by radicals $R^f$;

each $R^e$ is selected from $C_1$-$C_6$-alkyl, $C_3$-$C_6$-cycloalkyl, $C_3$-$C_6$-cycloalkyl-$C_1$-$C_4$-alkyl, which are unsubstituted or substituted by halogen, phenyl and benzyl, wherein the phenyl ring is unsubstituted or substituted by $R^f$;

each $R^f$ is selected from halogen, $N_3$, OH, CN, $NO_2$, SCN, $SF_5$, $C_1$-$C_6$ alkyl, $C_1$-$C_6$ alkoxy, $C_2$-$C_6$ alkenyl, $C_2$-$C_6$ alkynyl, $C_1$-$C_6$ alkoxy-$C_1$-$C_4$ alkyl, $C_1$-$C_6$ alkoxy-$C_1$-$C_4$ alkoxy, $C_3$-$C_6$ cycloalkyl, $C_3$-$C_6$ cycloalkoxy, $C_3$-$C_6$ cycloalkyl-$C_1$-$C_4$ alkyl, $C_3$-$C_6$ cycloalkoxy-$C_1$-$C_4$ alkyl, which are unsubstituted or substituted by halogen;

where m is 0, 1 or 2 and the N-oxides, stereoisomers, tautomers and agriculturally or veterinarily acceptable salts thereof.

General Procedure:

With due modification of the starting compounds, the compounds of formula I can principally be prepared by procedures as given in below schemes.

6H-imidazo[1,2-c]pyrimidin-5-thione Ia (X=S) can be prepared in an 4-step synthesis starting from cytidines 1 (Scheme 1). Condensation of cytidines 1 with alpha-haloaldehydes 2 as described, for example, Jansa et al. Journal of Heterocyclic Chemistry, 52(5), 1382-1389; 2015 leads to bicycles 3, which can be halogenated with, e.g. NIS or NBS, as described, for example, by Jansa et al. Tetrahedron, 71(1), 27-36; 2015. Halides 4 in turn can be subjected to a Suzuki coupling reaction with an arylboronic acid to form 6H-imidazo[1,2-c]pyrimidin-5-ones Ia (X=O) as described by, for example. Lee et al. PCT Int. Appl., 2009093981, 30 Jul. 2009. Finally reaction of compounds Ia (X=O) with a thiolating agent such as $P_2S_5$ or Lawesson's reagent will readily afford the compounds Ia (X=S) as described, for example, by Bigot et al. PCT Int. Appl., 2015052103, 16 Apr. 2015. Preparation of trifluoromethyl-substituted cytidine 1 ($R^1$=$CF_3$, $R^2$=H, $R^a$=H) has been prepared previously (Gershon et al. Journal of Heterocyclic Chemistry, 20(1), 219-23; 1983).

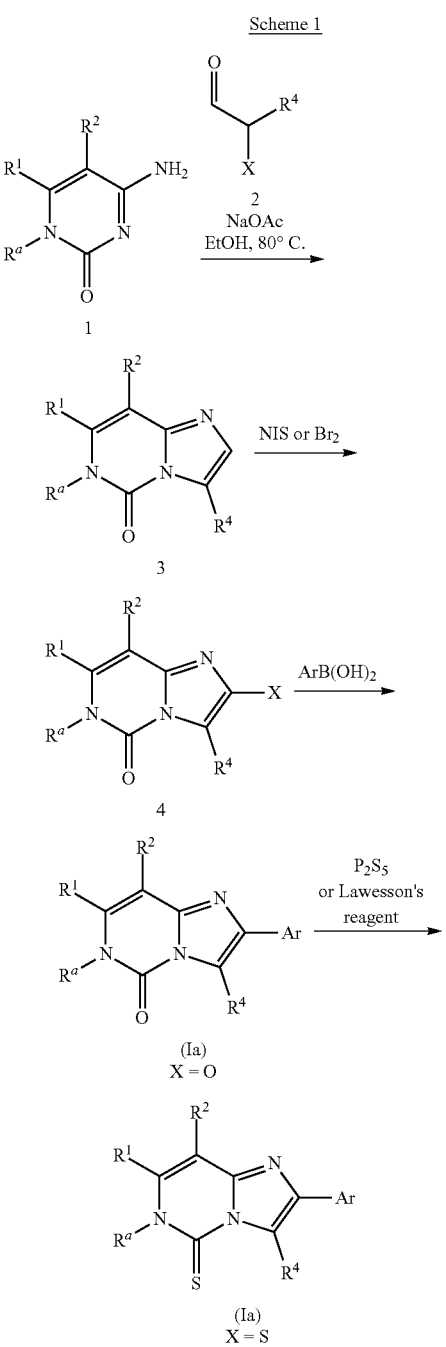

Alternatively compounds 6 can be prepared by condesation of aminopyridines 5 with an aldehydes 2 as described by, for example, Wade et al. U.S. Pat. No. 4,503,050, 5 Mar. 1985 (Scheme 2). Hydrolyis of chloro or methoxy group in compounds 6 (R=Cl, OMe) under standard conditions can afford compounds (Ia).

Scheme 2

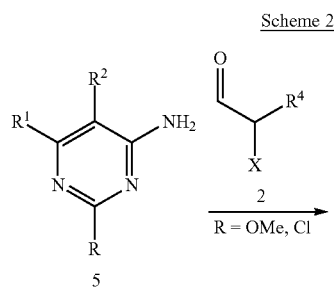

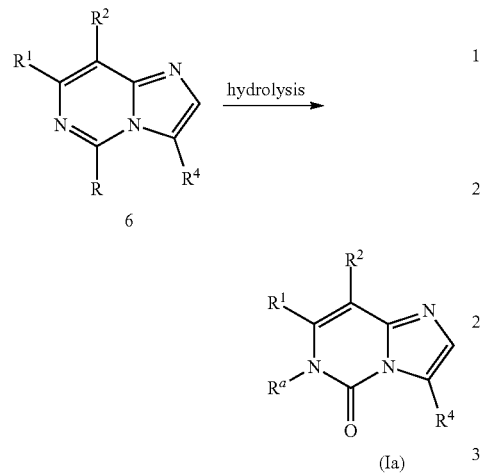

Direct condesation of alpha-halo-alpha-arylaldehydes (e.g. 7) and cytidines 1 can directly afforded compounds (Ia) as described by, for example, Meng et al. Bioorganic & Medicinal Chemistry Letters, 23(10), 2863-2867; 2013 (Scheme 3).

Scheme 3

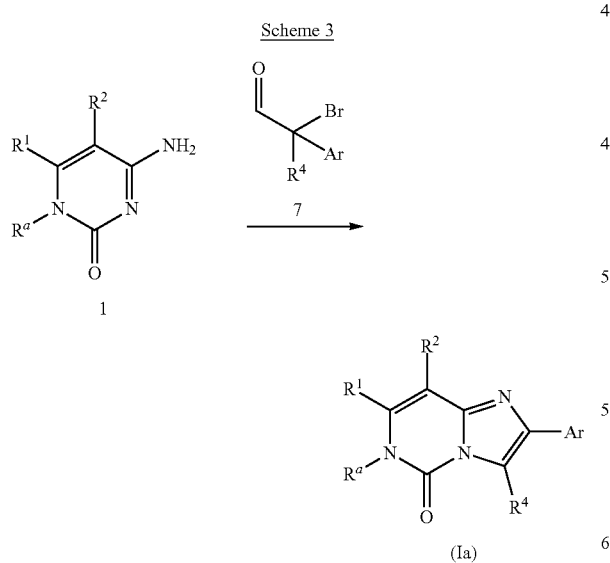

Compounds Ia can be prepared by N-alkylation of compounds 8 with an alkylation agent $R^a$—X as described, for example, by Martin-Martin et al. Bioorganic & Medicinal Chemistry Letters, 25(6), 1310-1317; 2015 (Scheme 4).

Scheme 4

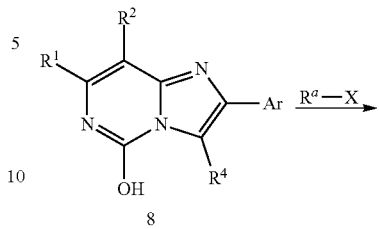

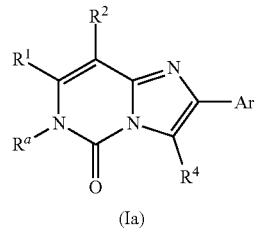

3H-[1,2,4]triazolo[1,5-a]pyridin-5-thiones Ib (X=S) can be prepared in a 4-step synthesis starting from N-aminopyridones 9 (Scheme 5). Condensation of compounds 9 with formic acid or an orthoformate as described, for example, Kubo et al. Yakugaku Zasshi, 99(8), 788-93; 1979 leads to bicycles 10. In analogy to for the synthesis of compounds (Ia) in Scheme 1, subsequent halogentation and Suzuki coupling of compounds 11 would lead to compounds Ib (X=O), which following thiolation would produce compound Ib (X=S).

Scheme 5

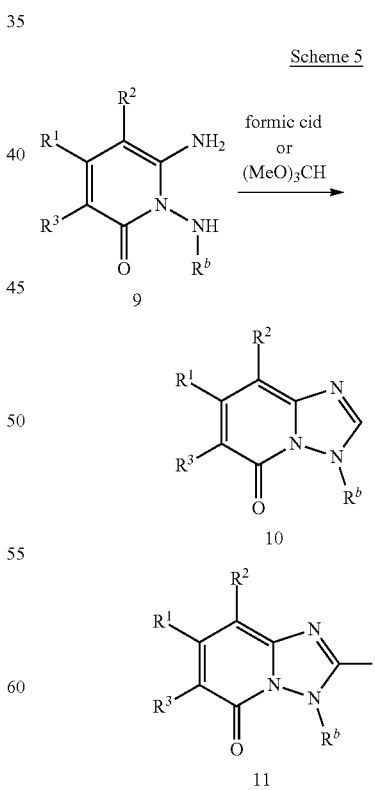

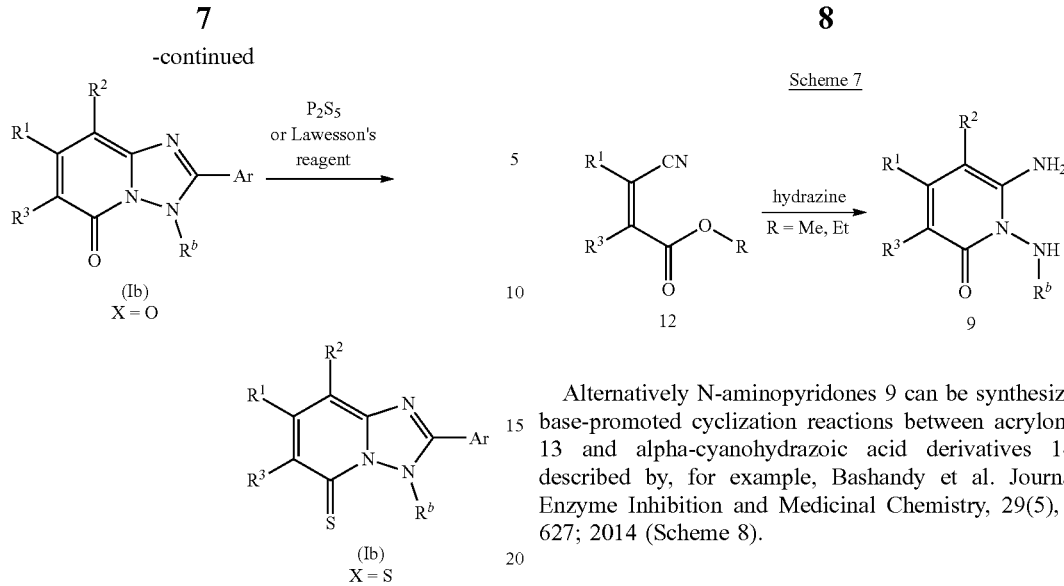

An cyclization reaction of aryl aldehydes and N-aminopyridones 9 in the presence of e.g. sodium metabisulfite as described, for example, by Kumartha et al Synthetic Communications, 44(23), 3414-3425; 2014 leads to the direct formation of Ib (X=O) (Scheme 6).

N-aminopyridones 9 can, in turn, be prepared by reaction of beta-cyanoacylates 12 with hydrazine as described by, for example, Kubo et al. Yakugaku Zasshi, 99(8), 788-93; 1979 (Scheme 7).

Alternatively N-aminopyridones 9 can be synthesized in base-promoted cyclization reactions between acrylonitrles 13 and alpha-cyanohydrazoic acid derivatives 14 as described by, for example, Bashandy et al. Journal of Enzyme Inhibition and Medicinal Chemistry, 29(5), 619-627; 2014 (Scheme 8).

The procedures described above can be used individually or in combination of one another to obtain compounds of formula 1.

The starting materials required for preparing the compounds of formula I are commercially available or can be prepared in accordance with the procedures known in literature.

The reaction mixtures are worked up in a customary manner, for example by mixing with water, separating the phases and, if appropriate, chromatographic purification of the crude products. Some of the intermediates and end products are obtained in the form of colorless or slightly brownish viscous oils which are purified or freed from volatile components under reduced pressure and at moderately elevated temperature. If the intermediates and end products are obtained as solids, purification can also be carried out by recrystallization or digestion.

If individual compounds of formula I cannot be obtained by the routes described above, they can be prepared by derivatization of other compounds of formula I or intermediates thereof.

The N-oxides may be prepared from the inventive compounds according to conventional oxidation methods, e.g. by treating compounds I with an organic peracid such as metachloroperbenzoic acid (cf. WO 03/64572 or J. Med. Chem. 38(11), 1892-903, 1995); or with inorganic oxidizing agents such as hydrogen peroxide (cf. J. Heterocyc. Chem. 18(7), 1305-8, 1981) or oxone (cf. J. Am. Chem. Soc.

123(25), 5962-5973, 2001). The oxidation may lead to pure mono-N-oxides or to a mixture of different N-oxides, which can be separated by conventional methods such as chromatography.

If the synthesis yields mixtures of isomers, a separation is generally not necessarily required since in some cases the individual isomers can be interconverted during work-up for use or during application (for example under the action of light, acids or bases). Such conversions may also take place after use, for example in the treatment of plants in the treated plant, or in the harmful fungus to be controlled.

A skilled person will readily understand that the preferences for the substituents, also in particular the ones given in the tables below for the respective substituents, given herein in connection with compounds I apply for the intermediates accordingly. Thereby, the substituents in each case have independently of each other or more preferably in combination the meanings as defined herein.

Unless otherwise indicated, the term "compound(s) according to the invention" or "compound(s) of the invention" or "compound(s) of formula (I)", refers to the compounds of formula I.

The term "compound(s) according to the invention", or "compounds of formula I" comprises the compound(s) as defined herein as well as a stereoisomer, salt, tautomer or N-oxide thereof. The term "compound(s) of the present invention" is to be understood as equivalent to the term "compound(s) according to the invention", therefore also comprising a stereoisomer, salt, tautomer or N-oxide thereof.

The term "composition(s) according to the invention" or "composition(s) of the present invention" encompasses composition(s) comprising at least one compound of formula I according to the invention as defined above. The compositions of the invention are preferably agricultural or veterinary compositions.

Depending on the substitution pattern, the compounds according to the invention may have one or more centers of chirality, in which case they are present as mixtures of enantiomers or diastereomers. The invention provides both the single pure enantiomers or pure diastereomers of the compounds according to the invention, and their mixtures and the use according to the invention of the pure enantiomers or pure diastereomers of the compounds according to the invention or their mixtures. Suitable compounds according to the invention also include all possible geometrical stereoisomers (cis/trans isomers) and mixtures thereof. Cis/trans isomers may be present with respect to an alkene, carbon-nitrogen double-bond or amide group. The term "stereoisomer(s)" encompasses both optical isomers, such as enantiomers or diastereomers, the latter existing due to more than one center of chirality in the molecule, as well as geometrical isomers (cis/trans isomers). The present invention relates to every possible stereoisomer of the compounds of formula I, i.e. to single enantiomers or diastereomers, as well as to mixtures thereof.

The compounds according to the invention may be amorphous or may exist in one or more different crystalline states (polymorphs) which may have different macroscopic properties such as stability or show different biological properties such as activities. The present invention relates to amorphous and crystalline compounds according to the invention, mixtures of different crystalline states of the respective compounds according to the invention, as well as amorphous or crystalline salts thereof.

Salts of the compounds according to the invention preferably agriculturally and/or veterinary acceptable salts, preferably agriculturally acceptable salts. They can be formed in a customary manner, e.g. by reacting the compound with an acid of the anion in question if the compounds according to the invention have a basic functionality or by reacting acidic compounds according to the invention with a suitable base.

Veterinary and/or agriculturally useful salts of the compounds according to the invention encompass especially the acid addition salts of those acids whose cations and anions, respectively, have no adverse effect on the pesticidal action of the compounds according to the invention.

Suitable cations are in particular the ions of the alkali metals, preferably Li, Na and K, of the alkaline earth metals, preferably Ca, Mg and Ba, and of the transition metals, preferably Mn, Cu, Zn and Fe, and also ammonium ($NH_4^+$) and substituted ammonium in which one to four of the H atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethyl-ammonium, tetramethylammonium, tetraethylammonium, tetrabutylammonium, 2-hydroxyethyl-ammonium, 2-(2-hydroxyethoxy)ethyl-ammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting compounds according to the invention with an acid of the corresponding anion, preferably of hydrochloric acid, hydrobromic acid, sulfuric acid, phosphoric acid or nitric acid.

The term "N-oxide" includes any compound of the present invention which has at least one tertiary nitrogen atom that is oxidized to an N-oxide moiety.

The organic moieties mentioned in the above definitions of the variables are—like the term halogen—collective terms for individual listings of the individual group members. The prefix $C_n$-$C_m$ indicates in each case the possible number of carbon atoms in the group.

The term "halogen" denotes in each case F, Br, Cl or I, in particular F, Br or Cl.

The term "alkyl" as used herein and in the alkyl moieties of alkylamino, alkylcarbonyl, alkylthio, alkylsulfinyl, alkylsulfonyl and alkoxyalkyl denotes in each case a straight-chain or branched alkyl group having usually from 1 to 10 carbon atoms, frequently from 1 to 6 carbon atoms, preferably 1 to 4 carbon atoms, more preferably from 1 to 3 carbon atoms. Examples of an alkyl group are $CH_3$, $C_2H_5$, n-propyl, iso-propyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methyl pentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl.

The term "haloalkyl" as used herein and in the haloalkyl moieties of haloalkylcarbonyl, haloalkoxycarbonyl, haloalkylthio, haloalkylsulfonyl, haloalkylsulfinyl, haloalkoxy and haloalkoxyalkyl, denotes in each case a straight-chain or branched alkyl group having usually from 1 to 6 carbon atoms, preferably from 1 to 4 carbon atoms, wherein the H atoms of this group are partially or fully replaced with halogen atoms. Preferred haloalkyl moieties are selected from $C_1$-$C_4$-haloalkyl, more preferably from $C_1$-$C_3$-haloalkyl or $C_1$-$C_2$-haloalkyl, in particular from $C_1$-$C_2$-fluoroalkyl such as fluoromethyl, difluoromethyl, trifluoromethyl, 1-fluoroethyl, 2-fluoroethyl, 2,2-difluoro-ethyl, 2,2,2-trifluoroethyl, pentafluoroethyl, and the like.

The term "alkoxy" as used herein denotes in each case a straight-chain or branched alkyl group which is bonded via an oxygen atom and has usually from 1 to 6 carbon atoms, preferably 1 to 4 carbon atoms. Examples of an alkoxy group are methoxy, ethoxy, n-propoxy, iso-propoxy, n-butyloxy, 2-butyloxy, iso-butyloxy, tert.-butyloxy, and the like.

The term "alkoxyalkyl" as used herein refers to alkyl usually comprising 1 to 4, preferably 1 to 2 carbon atoms, wherein 1 carbon atom carries an alkoxy radical usually comprising 1 to 4, preferably 1 or 2 carbon atoms as defined above. Examples are $CH_2OCH_3$, $CH_2$—$OC_2H_5$, 2-(methoxy)ethyl, and 2-(ethoxy)ethyl.

The term "haloalkoxy" as used herein denotes in each case a straight-chain or branched alkoxy group having from 1 to 6 carbon atoms, preferably 1 to 4 carbon atoms, wherein the H atoms of this group are partially or fully replaced with halogen atoms, in particular fluorine atoms. Preferred haloalkoxy moieties include $C_1$-$C_4$-haloalkoxy, in particular $C_1$-$C_2$-fluoroalkoxy, such as fluoromethoxy, difluoromethoxy, trifluoromethoxy, 1-fluoroethoxy, 2-fluoroethoxy, 2,2-difluoroethoxy, 2,2,2-trifluoro-ethoxy, 2-chloro-2-fluoroethoxy, 2-chloro-2,2-difluoro-ethoxy, 2,2-dichloro-2-fluorethoxy, 2,2,2-tri-chloroethoxy, pentafluoroethoxy and the like.

The term "alkylthio "(alkylsulfanyl: alkyl-S—)" as used herein refers to a straight-chain or branched saturated alkyl group having 1 to 6 carbon atoms, preferably 1 to 4 carbon atoms (=$C_1$-$C_4$-alkylthio), more preferably 1 to 3 carbon atoms, which is attached via a sulfur atom. Examples include methylthio, ethylthio, propylthio, isopropylthio, and n-butylthio.

The term "haloalkylthio" as used herein refers to an alkylthio group as mentioned above wherein the H atoms are partially or fully substituted by fluorine, chlorine, bromine and/or iodine. Examples include chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio and the like.

The term "alkylsulfinyl" (alkylsulfoxyl: $C_1$-$C_6$-alkyl-S(=O)—), as used herein refers to a straight-chain or branched saturated alkyl group (as mentioned above) having 1 to 6 carbon atoms, preferably 1 to 4 carbon atoms (=$C_1$-$C_4$-alkylsulfinyl), more preferably 1 to 3 carbon atoms bonded through the sulfur atom of the sulfinyl group at any position in the alkyl group.

The term "alkylsulfonyl" (alkyl-S(=O)$_2$-) as used herein refers to a straight-chain or branched saturated alkyl group having 1 to 6 carbon atoms, preferably 1 to 4 carbon atoms (=$C_1$-$C_4$-alkylsulfonyl), preferably 1 to 3 carbon atoms, which is bonded via the sulfur atom of the sulfonyl group at any position in the alkyl group.

The term "alkoxycarbonyl" refers to an alkylcarbonyl group as defined above, which is bonded via an oxygen atom to the remainder of the molecule.

The term "alkenyl" as used herein denotes in each case a singly unsaturated hydrocarbon radical having usually 2 to 6, preferably 2 to 4 carbon atoms, wherein the double bond may be present in any position, e.g. vinyl, allyl (2-propen-1-yl), 1-propen-1-yl, 2-propen-2-yl, methallyl (2-methylprop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl and the like.

The term "haloalkenyl" as used herein refers to an alkenyl group as defined above, wherein the H atoms are partially or fully replaced with halogen atoms.

The term "alkynyl" as used herein denotes in each case a singly unsaturated hydrocarbon radical having usually 2 to 6, preferably 2 to 4 carbon atoms, wherein the triple bond may be present in any position, e.g. ethynyl, propargyl (2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term "haloalkynyl" as used herein refers to an alkynyl group as defined above, wherein the H atoms are partially or fully replaced with halogen atoms.

The term "cycloalkyl" as used herein and in the cycloalkyl moieties of cycloalkoxy and cycloalkyl-thio denotes in each case a monocyclic cycloaliphatic radical having usually from 3 to 8 or from 3 to 6 carbon atoms, such as cyclopropyl, cyclobutyl, cyclopentyl, cyclohexyl, cycloheptyl, cyclooctyl, cyclononyl and cyclodecyl or cyclopropyl, cyclobutyl, cyclopentyl and cyclohexyl.

The term "halocycloalkyl" as used herein and in the halocycloalkyl moieties of halocycloalkoxy and halocycloalkylthio denotes in each case a monocyclic cycloaliphatic radical having usually from 3 to 8 C atoms or 3 to 6 C atoms, wherein at least one, e.g. 1, 2, 3, 4 or 5 of the H atoms, are replaced by halogen, in particular by fluorine or chlorine. Examples are 1- and 2-fluorocyclopropyl, 1,2-, 2,2- and 2,3-difluorocyclopropyl, 1,2,2-trifluorocyclopropyl, 2,2,3,3-tetrafluorocyclpropyl, 1- and 2-chlorocyclopropyl, 1,2-, 2,2- and 2,3-dichlorocyclopropyl, 1,2,2-trichlorocyclopropyl, 2,2,3,3-tetrachlorocyclpropyl, 1-,2- and 3-fluorocyclopentyl, 1,2-, 2,2-, 2,3-, 3,3-, 3,4-, 2,5-difluorocyclopentyl, 1-,2- and 3-chlorocyclopentyl, 1,2-, 2,2-, 2,3-, 3,3-, 3,4-, 2,5-dichlorocyclopentyl and the like.

The term "cycloalkenyl" as used herein and in the cycloalkenyl moieties of cycloalkenyloxy and cycloalkenylthio denotes in each case a monocyclic singly unsaturated non-aromatic radical having usually from 3 to 8, e.g. 3 or 4 or from 5 to 10 carbon atoms, preferably from 3- to 8 carbon atoms. Exemplary cycloalkenyl groups include cyclopropenyl, cycloheptenyl or cyclooctenyl.

The term "substituted" if not specified otherwise refers to substituted by 1, 2 or maximum possible number of substituents. If substituents as defined in compounds of formula I are more than one then they are independently from each other are same or different if not mentioned otherwise.

The term "carbocycle" or "carbocyclyl" includes, unless otherwise indicated, in general a 3- to 12-membered, preferably a 3- to 8-membered or a 5- to 8-membered, more preferably a 5- or 6-membered mono-cyclic, non-aromatic ring comprising 3 to 12, preferably 3 to 8 or 5 to 8, more preferably 5 or 6 carbon atoms. Preferably, the term "carbocycle" covers cycloalkyl and cycloalkenyl groups as defined above, for example cyclopropane, cyclobutane, cyclopentane and cyclohexane rings.

The term "heterocycle" or "heterocyclyl" includes, unless otherwise indicated, in general 3- to 10-membered, preferably 3- to 8-membered or 5- to 8-membered, more preferably 5- or 6-membered, in particular 6-membered monocyclic heterocyclic non-aromatic radicals. The heterocyclic non-aromatic radicals usually comprise 1, 2, 3, 4 or 5, preferably 1, 2 or 3 heteroatoms selected from N, O and S as ring members, where S-atoms as ring members may be present as S, SO or $SO_2$. If not mentioned contrary, the N and S atoms of the heterocycle can be oxidized. Examples of 5- or 6-membered heterocyclic radicals comprise saturated or unsaturated, non-aromatic heterocyclic rings, such as oxiranyl, oxetanyl, thietanyl, thietanyl-S-oxid (S-oxothietanyl), thietanyl-S-dioxid (S-dioxothiethanyl), pyrrolidinyl, pyrrolinyl, pyrazolinyl, tetrahydrofuranyl, dihydrofuranyl, 1,3-dioxolanyl, thiolanyl, S-oxothiolanyl, S-dioxothiolanyl, dihydrothienyl, S-oxodihydrothienyl, S-dioxodihydrothienyl, oxazolidinyl, oxazolinyl, thiazolinyl, oxathiolanyl, piperidinyl, piperazinyl, pyranyl, dihydropyranyl, tetrahydropyranyl, 1,3- and 1,4-dioxanyl, thiopyranyl, S.oxothiopyranyl, S-dioxothiopyranyl, dihydrothiopyranyl, S-oxodihydrothiopyranyl, S-dioxodihydrothiopyranyl, tetrahydrothiopyranyl, S-oxotetrahydrothiopyranyl, S-dioxotetrahydrothiopyranyl, morpholinyl, thiomorpholinyl, S-oxothiomorpholinyl, S-dioxothiomorpholinyl, thiazinyl and the like. Examples for heterocyclic ring also comprising 1 or 2 carbonyl groups as ring members comprise pyrrolidin-2-onyl, pyrrolidin-2,5-dionyl, imidazolidin-2-onyl, oxazolidin-2-onyl, thiazolidin-2-onyl and the like.

The term "partially or fully unsaturated heterocycle" or "partially or fully unsaturated heterocyclic ring" refers to heterocycle which is partially unsaturated or heterocycle which is fully unsaturated. Partially unsaturated heterocycle includes monocyclic 3- or 6-membered partially unsaturated heterocyclic radicals comprising as ring members 1, 2, 3 or 4 heteroatoms selected from N, O and S. Examples of 3- to 6-membered partially unsaturated heterocycles include azirine, oxeteen, dihydropyrol, dihydrofuran, dihydrothiophene, dihydrooxazole, dihydroimidazole, dihydrothiazole, tetrahydropyrazine, dihydrooxazine. Fully unsaturated heterocycle includes monocyclic 5- or 6-membered fully unsaturated heterocyclic radicals comprising as ring members 1, 2, 3 or 4 heteroatoms selected from N, O and S. Examples of 5- or 6-membered fully unsaturated heterocycles include pyridyl, i.e. 2-, 3-, or 4-pyridyl, pyrimidinyl, i.e. 2-, 4- or 5-pyrimidinyl, pyrazinyl, pyridazinyl, i.e. 3- or 4-pyridazinyl, thienyl, i.e. 2- or 3-thienyl, furyl, i.e. 2- or 3-furyl, pyrrolyl, i.e. 2- or 3-pyrrolyl, oxazolyl, i.e. 2-, 3- or 5-oxazolyl, isoxazolyl, i.e. 3-, 4- or 5-isoxazolyl, thiazolyl, i.e. 2-, 3- or 5-thiazolyl, isothiazolyl, i.e. 3-, 4- or 5-isothiazolyl, pyrazolyl, i.e. 1-, 3-, 4- or 5-pyrazolyl, i.e. 1-, 2-, 4- or 5-imidazolyl, oxadiazolyl, e.g. 2- or 5-[1,3,4]oxadiazolyl, 4- or 5-(1,2,3-oxadiazol)yl, 3- or 5-(1,2,4-oxadiazol)yl, 2- or 5-(1,3,4-thiadiazol)yl, thiadiazolyl, e.g. 2- or 5-(1,3,4-thiadiazol)yl, 4- or 5-(1,2,3-thiadiazol)yl, 3- or 5-(1,2,4-thiadiazol)yl, triazolyl, e.g. 1H-, 2H- or 3H-1,2,3-triazol-4-yl, 2H-triazol-3-yl, 1H-, 2H-, or 4H-1,2,4-triazolyl and tetrazolyl, i.e. 1H- or 2H-tetrazolyl. The term "partially or fully unsaturated heterocycle" or "partially or fully unsaturated heterocyclic ring" also includes bicyclic 8 to 10-membered partially or fully unsaturated heterocyclic radicals comprising as ring members 1, 2 or 3 heteroatoms selected from N, O and S, wherein a 5- or 6-membered hetercyclic ring is fused to a phenyl ring or to a 5- or 6-membered heteroaromatic radical. Examples of a 5- or 6-membered heteroaromatic ring fused to a phenyl ring or to a 5- or 6-membered heteroaromatic radical include benzofuranyl, benzothienyl, indolyl, indazolyl, benzimidazolyl, benzoxathiazolyl, benzoxadiazolyl, benzothiadiazolyl, benzoxazinyl, chinolinyl, isochinolinyl, purinyl, 1,8-naphthyridyl, pteridyl, pyrido[3,2-d]pyrimidyl or pyridoimidazolyl and the like. These fused hetaryl radicals may be bonded to the remainder of the molecule via any ring atom of 5- or 6-membered heteroaromatic ring or via a carbon atom of the fused phenyl moiety.

The term "heteroaryl" refers to "fully unsaturated heterocycle".

The terms "alkylene", "alkenylene", and "alkynylene" refer to alkyl, alkenyl, and alkynyl as defined above, respectively, which are bonded to the remainder of the molecule, via two atoms, preferably via two carbon atoms, of the respective group, so that they represent a linker between two moieties of the molecule. In particular, the term "alkylene" may refer to alkyl chains such as —$CH_2CH_2$—, —$CH(CH_3)$—, —$CH_2CH_2CH_2$—, —$CH(CH_3)CH_2$—, —$CH_2CH(CH_3)$—, —$CH_2CH_2CH_2CH_2$—, —$CH_2CH_2CH_2CH_2CH_2$—, —$CH_2CH_2CH_2CH_2CH_2CH_2$—, and —$CH_2CH_2CH_2CH_2CH_2CH_2CH_2$—. Similarly, "alkenylene" and "alkynylene" may refer to alkenyl and alkynyl chains, respectively.

The term "CN" refers to cyano group.

With respect to the variables, the particularly preferred embodiments of the compounds of the formula I.

In one preferred embodiment of compounds of formula I, X is O.

In another preferred embodiment of compounds of formula I, X is S.

In one preferred embodiment of compounds of formula I, P is $NR^x$ and Q is $CR^4$.

In another preferred embodiment of compounds of formula I, P is $CR^3$ and Q is $NR^y$.

In one preferred embodiment of the present invention the compound of formula I is compound of formula I-A or compounds of formula I-B.

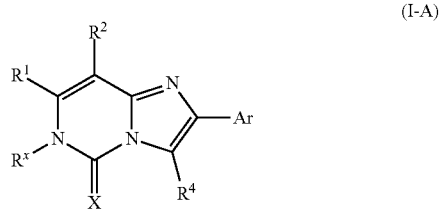

(I-A)

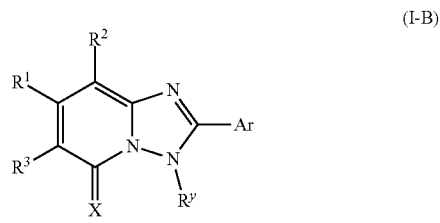

(I-B)

In one more preferred embodiment the compounds of formula I is compounds of formula I-A.

In another more preferred embodiment the compounds of formula I is compounds of formula I-B.

In one preferred embodiment of compounds of formula I, $R^x$ is selected from $C_1$-$C_3$ alkyl, $C_1$-$C_3$ alkoxy, $C_2$-$C_3$ alkenyl, $C_2$-$C_3$ alkynyl, $C_3$-$C_6$ cycloalkyl, $C_1$-$C_3$haloalkyl, $C_1$-$C_3$haloalkoxy, $C_2$-$C_3$ haloalkenyl, $C_2$-$C_3$ haloalkynyl and $C_3$-$C_6$ halocycloalkyl.

In more preferred embodiment of compounds of formula I, $R^x$ is selected from $C_1$-$C_3$ alkyl, $C_2$-$C_3$ alkenyl, $C_2$-$C_3$alkynyl, $C_3$-$C_6$cycloalkyl, and $C_1$-$C_3$haloalkyl.

In most preferred embodiment of compounds of formula I, $R^x$ is selected from $CH_3$, $C_2H_5$, n-propyl, isopropyl, cyclopropyl, allyl and propargyl.

In perticularly preferred embodiment of compounds of formula I, $R^x$ is $CH_3$ or $C_2H_5$.

In one preferred embodiment of compounds of formula I, $R^y$ is selected from $C_1$-$C_3$ alkyl, $C_1$-$C_3$ alkoxy, $C_2$-$C_3$ alkenyl, $C_2$-$C_3$ alkynyl, $C_3$-$C_6$ cycloalkyl, $C_1$-$C_3$haloalkyl, $C_1$-$C_3$haloalkoxy, $C_2$-$C_3$ haloalkenyl, $C_2$-$C_3$ haloalkynyl and $C_3$-$C_6$ halocycloalkyl.

In more preferred embodiment of compounds of formula I, $R^y$ is selected from $CH_3$, $C_2H_5$, n-propyl, isopropyl, cyclopropyl, allyl and propargyl.

In most preferred embodiment of compounds of formula I, $R^y$ is $CH_3$ or $C_2H_5$.

In one preferred embodiment of compounds of formula I, $R^a$ is selected from H, $C_1$-$C_3$alkyl, $C_1$-$C_3$ alkoxy, $C_2$-$C_3$ alkenyl, $C_2$-$C_3$ alkynyl, $C_3$-$C_6$ cycloalkyl, $C_1$-$C_3$haloalkyl, $C_1$-$C_3$haloalkoxy, $C_2$-$C_3$ haloalkenyl, $C_2$-$C_3$ haloalkynyl and $C_3$-$C_6$ halocycloalkyl.

In most preferred embodiment of compounds of formula I, $R^a$ is selected from H, $CH_3$, $C_2H_5$, n-propyl, isopropyl, cyclopropyl, allyl and propargyl.

In one preferred embodiment of compounds of formula I, $R^b$ is selected from H, $C_1$-$C_3$alkyl, $C_1$-$C_3$ alkoxy, $C_2$-$C_3$ alkenyl, $C_2$-$C_3$ alkynyl, $C_3$-$C_6$ cycloalkyl, $C_1$-$C_3$haloalkyl, $C_1$-$C_3$haloalkoxy, $C_2$-$C_3$ haloalkenyl, $C_2$-$C_3$ haloalkynyl and $C_3$-$C_6$ halocycloalkyl.

In most preferred embodiment of compounds of formula I, $R^b$ is selected from H, $CH_3$, $C_2H_5$, n-propyl, isopropyl, cyclopropyl, allyl and propargyl.

In one preferred embodiment of compounds of formula I, $R^c$ is selected from H, $C_1$-$C_3$ alkyl, $C_1$-$C_3$ alkoxy, $C_2$-$C_3$ alkenyl, $C_2$-$C_3$ alkynyl, $C_3$-$C_6$ cycloalkyl, $C_1$-$C_3$haloalkyl, $C_1$-$C_3$haloalkoxy, $C_2$-$C_3$ haloalkenyl, $C_2$-$C_3$ haloalkynyl and $C_3$-$C_6$ halocycloalkyl.

In most preferred embodiment of compounds of formula I, $R^c$ is selected from H, $CH_3$, $C_2H_5$, n-propyl, isopropyl, cyclopropyl, allyl and propargyl.

In one preferred embodiment of compounds of formula I, $R^b$ is selected from H, CN, $C_1$-$C_3$ alkyl, $C_1$-$C_3$ alkoxy, $C_2$-$C_3$ alkenyl, $C_2$-$C_3$ alkynyl, $C_3$-$C_6$ cycloalkyl, $C_1$-$C_3$haloalkyl, $C_1$-$C_3$haloalkoxy, $C_2$-$C_3$ haloalkenyl, $C_2$-$C_3$ haloalkynyl and $C_3$-$C_6$ halocycloalkyl.

In another preferred embodiment of compounds of formula I, $R^2$ is selected from H, $C_1$-$C_3$ alkyl, $C_1$-$C_3$ alkoxy, $C_2$-$C_3$ alkenyl, $C_2$-$C_3$ alkynyl, $C_3$-$C_6$ cycloalkyl, $C_1$-$C_3$haloalkyl, $C_1$-$C_3$haloalkoxy, $C_2$-$C_3$ haloalkenyl, $C_2$-$C_3$ haloalkynyl and $C_3$-$C_6$ halocycloalkyl.

In more preferred embodiment of compounds of formula I, $R^2$ is selected from H, $CH_3$, $C_2H_5$, n-propyl, isopropyl, cyclopropyl, allyl and propargyl.

In most preferred embodiment of compounds of formula I, $R^2$ is selected from H, $CH_3$ and $C_2H_5$.

In perticularly preferred embodiment of compounds of formula I, $R^2$ is H.

In one preferred embodiment of compounds of formula I, $R^3$ is selected from H, CN, $C_1$-$C_3$ alkyl, $C_1$-$C_3$ alkoxy, $C_2$-$C_3$ alkenyl, $C_2$-$C_3$ alkynyl, $C_3$-$C_6$ cycloalkyl, $C_1$-$C_3$haloalkyl, $C_1$-$C_3$haloalkoxy, $C_2$-$C_3$ haloalkenyl, $C_2$-$C_3$ haloalkynyl and $C_3$-$C_6$ halocycloalkyl.

In most preferred embodiment of compounds of formula I, $R^3$ is selected from H, $CH_3$, $C_2H_5$, n-propyl, isopropyl, cyclopropyl, allyl and propargyl.

In most preferred embodiment of compounds of formula I, $R^3$ is selected from H, $CH_3$ and $C_2H_5$.

In one preferred embodiment of compounds of formula I, $R^4$ is selected from H, CN, $C_1$-$C_3$ alkyl, $C_1$-$C_3$ alkoxy, $C_2$-$C_3$ alkenyl, $C_2$-$C_3$ alkynyl, $C_3$-$C_6$ cycloalkyl, $C_1$-$C_3$haloalkyl, $C_1$-$C_3$haloalkoxy, $C_2$-$C_3$ haloalkenyl, $C_2$-$C_3$ haloalkynyl and $C_3$-$C_6$ halocycloalkyl.

In most preferred embodiment of compounds of formula I, $R^4$ is selected from H, $CH_3$, $C_2H_5$, n-propyl, isopropyl, cyclopropyl, allyl and propargyl.

In most preferred embodiment of compounds of formula I, $R^4$ is selected from H, $CH_3$ and $C_2H_5$.

In a preferred embodiment of compounds of formula I, $R^e$ is selected from $C_1$-$C_3$ alkyl, $C_1$-$C_3$ alkoxy, $C_2$-$C_3$ alkenyl, $C_2$-$C_3$ alkynyl, $C_3$-$C_6$ cycloalkyl, $C_1$-$C_3$haloalkyl, $C_1$-$C_3$haloalkoxy, $C_2$-$C_3$ haloalkenyl, $C_2$-$C_3$ haloalkynyl and $C_3$-$C_6$ halocycloalkyl.

In more preferred embodiment of compounds of formula I, $R^e$ is selected from $C_1$-$C_3$ alkyl, $C_3$-$C_6$ cycloalkyl, $C_1$-$C_3$haloalkyl, and $C_3$-$C_6$ halocycloalkyl.

In most preferred embodiment of compounds of formula I, $R^e$ is selected from $CH_3$, $C_2H_5$, n-propyl, isopropyl, cyclopropyl, allyl and propargyl.

In one preferred embodiment of compounds of formula I, $R^f$ is selected from halogen, CN, $C_1$-$C_3$ alkyl, $C_1$-$C_3$ alkoxy, $C_2$-$C_3$ alkenyl, $C_2$-$C_3$ alkynyl, $C_3$-$C_6$ cycloalkyl, $C_1$-$C_3$haloalkyl, $C_1$-$C_3$haloalkoxy, $C_2$-$C_3$ haloalkenyl, $C_2$-$C_3$ haloalkynyl and $C_3$-$C_6$ halocycloalkyl.

In more preferred embodiment of compounds of formula I, $R^f$ is selected from Cl, F, Br, $OCH_3$, $OC_2H_5$, $SCH_3$, $SC_2H_5$, CN, $CH_3$, $C_2H_5$, n-propyl, isopropyl, cyclopropyl, allyl, propargyl, $CF_3$, $CHF_2$, and $CF_2CF_3$.

In one preferred embodiment of compounds of formula I, $R^1$ is partially or completely halogenated $C_1$-$C_6$ alkyl, more preferably $C_1$-$C_4$ alkyl, particularly $C_1$-$C_2$ alkyl such as $CF_3$, $CF_2CF_3$ and $CF(CF_3)_2$.

In another preferred embodiment of compounds of formula I, $R^1$ is partially or completely halogenated $C_1$-$C_6$-alkoxy, more preferably $C_1$-$C_4$ alkoxy, particularly $C_1$-$C_2$ alkoxy such as $OCF_3$, $OCH_2CHF_2$ and $OCH_2CF_3$.

In another preferred embodiment of compounds of formula I, $R^1$ is partially or completely halogenated $C_2$-$C_6$ alkenyl or $C_2$-$C_6$ alkynyl.

In another preferred embodiment of compounds of formula I, $R^1$ is partially or completely halogenated $C_3$-$C_6$ cycloalkyl or $C_3$-$C_6$ cycloalkoxy.

In another preferred embodiment of compounds of formula I, $R^1$ is partially or completely halogenated $C_1$-$C_6$ sulfenyl such as $SCF_3$, $C_1$-$C_6$ sulfinyl such as $S(=O)CF_3$ or $C_1$-$C_6$ sulfonyl such as $S(=O)_2CF_3$.

In more preferred embodiment of compounds of formula I, $R^1$ is $CF_3$, $CF_2CF_3$, $OCHF_2$, $CF(CF_3)_2$, $SCF_3$, $OCF_3$, $S(=O)CF_3$ or $S(=O)_2CF_3$.

In a particularly preferred embodiment of compounds of formula I, $R^f$ is $CF_3$, $CF_2CF_3$, $CF(CF_3)_2$, $SCF_3$, $OCF_3$, $S(=O)CF_3$ or $S(=O)_2CF_3$.

In a particular embodiment of compounds of formula I, $R^1$ is $CF_3$, $CF_2CF_3$, $OCHF_2$, or $OCF_3$.

In a particular embodiment of compounds of formula I, $R^1$ is $CF_3$.

In one preferred embodiment of compounds of formula I, Ar is phenyl.

In another preferred embodiment of compound of formula I, Ar is heteroaryl.

In more preferred embodiment of compound of formula I, wherein Ar is phenyl or 5-6 membered heteroaryl substituted with $S(=O)_m R^e$ at the ortho position to the bond connecting to 9-membered heteroaryl of compound of formula I, and optionally further substituted with 1 or 2 $R^{Ar}$, preferably selected from halogen, $C_1$-$C_6$ alkyl, $C_1$-$C_6$haloalkyl, $C_1$-$C_6$alkoxy, $C_1$-$C_6$haloalkoxy, phenyl, and benzyl, wherein the phenyl ring is unsubstituted or substituted by radicals $R^f$.

In another preferred embodiment of compounds of formula I, Ar is selected from formula Ar-1 to Ar-9, wherein the formula Ar-1 to Ar-9 are substituted with 1, 2, or 3 $R^{Ar}$, and wherein one $R^{Ar}$ substituent is preferably at the ortho position to ⁃ bond;

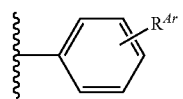
Ar-1

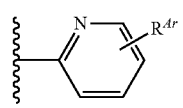
Ar-2

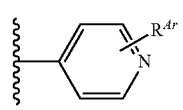
Ar-3

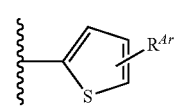
Ar-4

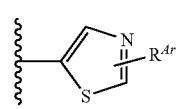
Ar-5

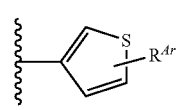
Ar-6

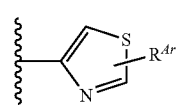
Ar-7

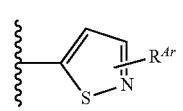
Ar-8

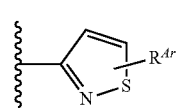
Ar-9

In one preferred embodiment of compounds of formula I, $R^{Ar}$ is selected from halogen, $C_1$-$C_6$ alkyl, $C_1$-$C_6$haloalkyl, $C_1$-$C_6$alkoxy, $C_1$-$C_6$haloalkoxy, $S(=O)_m R^e$, phenyl, phenoxy, phenylcarbonyl, phenylthio and benzyl, wherein the phenyl ring is unsubstituted or substituted by radicals $R^f$.

In more preferred embodiment of compounds of formula I, $R^{Ar}$ is selected from halogen, $C_1$-$C_6$ alkyl, $C_1$-$C_6$haloalkyl, $C_1$-$C_6$alkoxy, $C_1$-$C_6$haloalkoxy, $S(=O)_m R^e$, phenyl, and benzyl, wherein the phenyl ring is unsubstituted or substituted by radicals $R^f$.

In one preferred embodiment of compounds of formula I, $R^{Ar}$ is selected from halogen, $C_1$-$C_6$ alkyl, $C_1$-$C_6$haloalkyl, $C_1$-$C_6$alkoxy, and $C_1$-$C_6$haloalkoxy. In another preferred embodiment of compounds of formula I, $R^{Ar}$ is selected from $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, $C_3$-$C_6$ halocycloalkyl, $C_3$-$C_6$cycloalkoxy and $C_3$-$C_6$halocycloalkoxy.

In another preferred embodiment of compounds of formula I, $R^{Ar}$ is selected from $C_1$-$C_6$-sulfenyl, $C_1$-$C_6$-sulfinyl and $C_1$-$C_6$-sulfonyl.

In more preferred embodiment of compounds of formula I, $R^{Ar}$ is selected from Cl, F, Br, $CH_3$, $SCH_3$, $SC_2H_5$, $S(=O)CH_3$, $S(=O)C_2H_5$, $S(=O)_2CH_3$, $S(=O)_2C_2H_5$.

In most preferred embodiment of compounds of formula I, $R^{Ar}$ is $S(=O)_2C_2H_5$.

In a particularly preferred embodiment of compound of formula I, Ar is selected from the group of formula Ar-1a to Ar-1f, Ar-2a to Ar-2f, Ar-3a to Ar-3c, Ar-4a to Ar-4f, Ar-6a to Ar-6c, Ar-8a to Ar-8c, Ar-9a to Ar-9c and Ar-10a to Ar-10j:

In a particularly preferred embodiment of compound of formula I, Ar is selected from the group of formula Ar-1a to Ar-1f, Ar-2a to Ar-2f, Ar-3a to Ar-3c, Ar-4a to Ar-4f, Ar-6a to Ar-6c, Ar-8a to Ar-8c, and Ar-9a to Ar-9c:

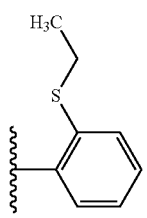
Ar-1a

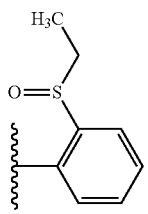
Ar-1b

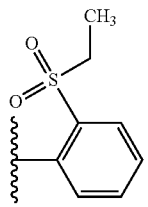
Ar-1c

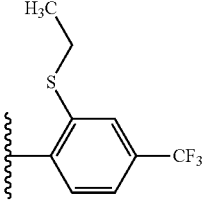
Ar-1d

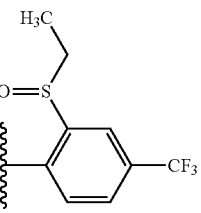
Ar-1e

-continued
Ar-1f
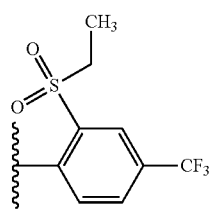
Ar-2a
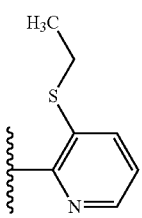
Ar-2b
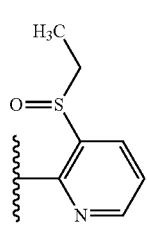
Ar-2c
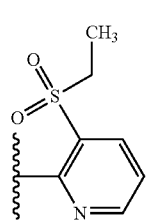
Ar-2d
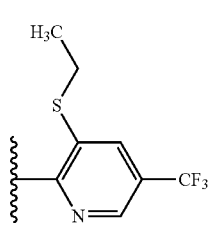
Ar-2e
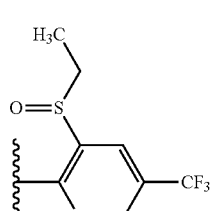
Ar-2f
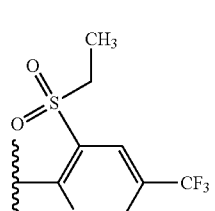
-continued
Ar-3a
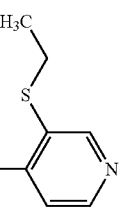
Ar-3b
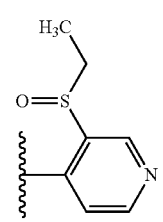
Ar-3c
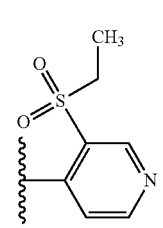
Ar-4a
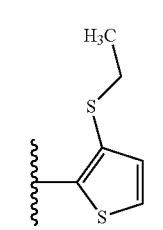
Ar-4b
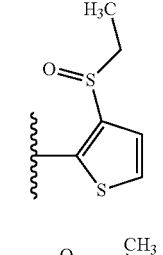
Ar-4c
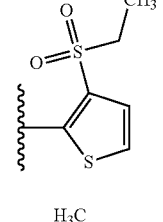
Ar-4d
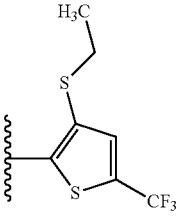

-continued
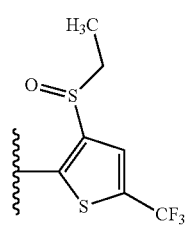
Ar-4e
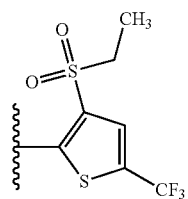
Ar-4f
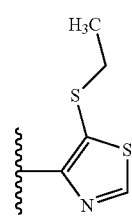
Ar-6a
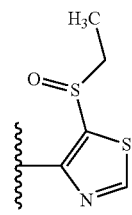
Ar-6b
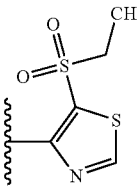
Ar-6c
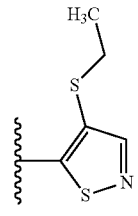
Ar-8a
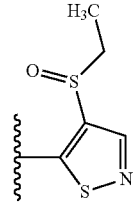
Ar-8b
-continued
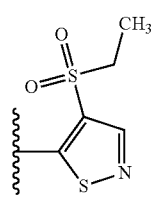
Ar-8c
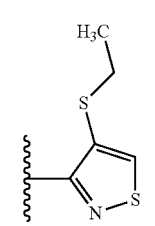
Ar-9a
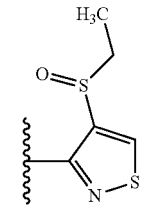
Ar-9b
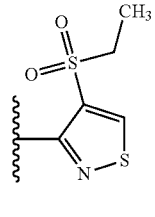
Ar-9c
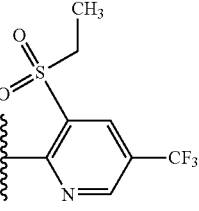
Ar-10a
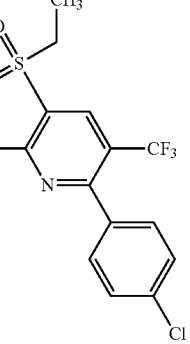
Ar-10b

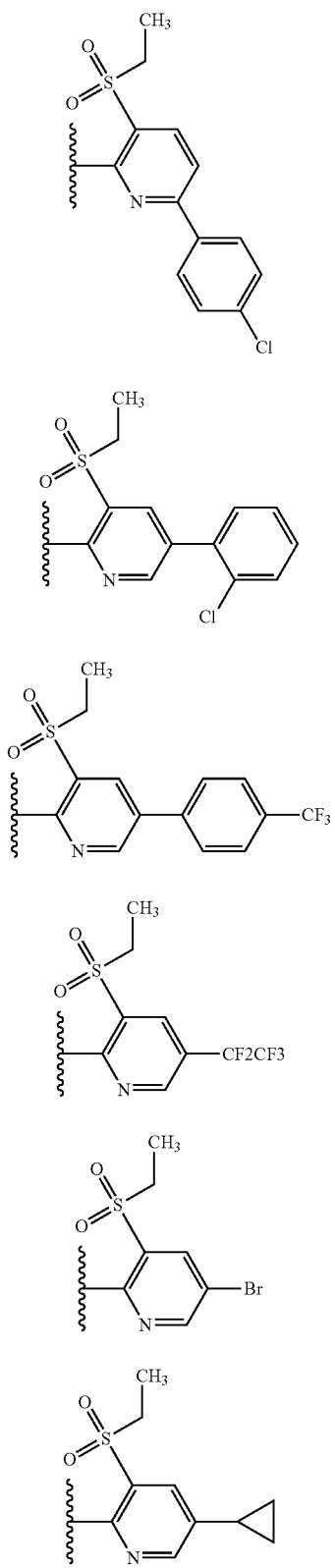
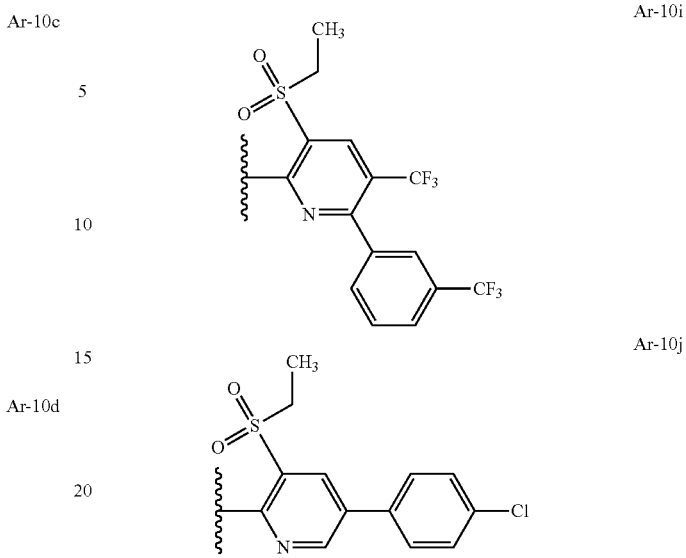

Each of the groups mentioned for a substituent in the tables is furthermore per se, independently of the combination in which it is mentioned, a particularly preferred aspect of the substituent in question.

In another preferred embodiment the compounds of formula I are compounds of formula I-A, wherein $R^x$ is selected from $C_1$-$C_3$ alkyl, $C_2$-$C_3$ alkenyl, $C_2$-$C_3$ alkynyl, $C_3$-$C_6$ cycloalkyl, and $C_1$-$C_3$haloalkyl;

$R^1$ is selected from partially or completely halogenated, $C_1$-$C_6$ alkyl, $C_1$-$C_6$ sulfenyl, $C_1$-$C_6$ sulfinyl, and $C_1$-$C_6$ sulfonyl;

$R^2$ is selected from H, $CH_3$, $C_2H_5$, n-propyl, isopropyl, cyclopropyl, allyl and propargyl;

$R^4$ is selected from H, $CH_3$, $C_2H_5$, n-propyl, isopropyl, cyclopropyl, allyl and propargyl;

Ar is a phenyl or 5-6 membered heteroaryl substituted with $R^{Ar}$;

$R^{Ar}$ is selected from halogen, $C_1$-$C_6$ alkyl, $C_1$-$C_6$haloalkyl, $C_1$-$C_6$alkoxy, $C_1$-$C_6$haloalkoxy, $S(=O)_m R^e$, phenyl, phenoxy, phenylcarbonyl, phenylthio and benzyl, wherein the phenyl ring is unsubstituted or substituted by radicals $R^f$;

$R^e$ is selected from $C_1$-$C_3$ alkyl, $C_3$-$C_6$ cycloalkyl, $C_1$-$C_3$haloalkyl, and $C_3$-$C_6$ halocycloalkyl;

$R^f$ is selected from Cl, F, Br, $OCH_3$, $OC_2H_5$, $SCH_3$, $SC_2H_5$, CN, $CH_3$, $C_2H_5$, n-propyl, isopropyl, cyclopropyl, allyl, propargyl, $CF_3$, $CHF_2$, and $CF_2CF_3$.

In another more preferred embodiment the compounds of formula I are compounds of formula I-A, wherein $R^x$ is $CH_3$ or $C_2H_5$;

$R^1$ is selected from $CF_3$, $CF_2CF_3$, $CF(CF_3)_2$, $SCF_3$, $OCF_3$, $OCHF_2$, $S(=O)CF_3$, and $S(=O)_2CF_3$;

$R^2$ is selected from H, $CH_3$, and $C_2H_5$;

$R^4$ is selected from H, $CH_3$, and $C_2H_5$;

Ar is a phenyl or 5-6 membered heteroaryl substituted with $S(=O)_m R^e$ at the ortho position to bond connecting to 9-membered heteroaryl of compound of formula I, and optionally further substituted with 1 or 2 $R^{Ar}$, preferably selected from halogen, $C_1$-$C_6$ alkyl, $C_1$-$C_6$haloalkyl, $C_1$-$C_6$alkoxy, $C_1$-$C_6$ haloalkoxy, phenyl, and benzyl, wherein the phenyl ring is unsubstituted or substituted by radicals $R^f$.

In another preferred embodiment the compounds of formula I are compounds of formula I-B, wherein $R^y$ is selected from $C_1$-$C_3$ alkyl, $C_2$-$C_3$ alkenyl, $C_2$-$C_3$ alkynyl, $C_3$-$C_6$ cycloalkyl, and $C_1$-$C_3$haloalkyl;

$R^1$ is selected from partially or completely halogenated, $C_1$-$C_6$ alkyl, $C_1$-$C_6$ sulfenyl, $C_1$-$C_6$ sulfinyl, and $C_1$-$C_6$ sulfonyl;

$R^2$ is selected from H, $CH_3$, $C_2H_5$, n-propyl, isopropyl, cyclopropyl, allyl and propargyl;

$R^3$ is selected from H, $CH_3$, $C_2H_5$, n-propyl, isopropyl, cyclopropyl, allyl and propargyl;

Ar is a phenyl or 5-6 membered heteroaryl substituted with $R^{Ar}$.

$R^{Ar}$ is selected from halogen, $C_1$-$C_6$ alkyl, $C_1$-$C_6$haloalkyl, $C_1$-$C_6$alkoxy, $C_1$-$C_6$ haloalkoxy, $S(=O)_mR^e$, phenyl, phenoxy, phenylcarbonyl, phenylthio and benzyl, wherein the phenyl ring is unsubstituted or substituted by radicals $R^f$;

$R^e$ is selected from $C_1$-$C_3$ alkyl, $C_3$-$C_6$ cycloalkyl, $C_1$-$C_3$haloalkyl, and $C_3$-$C_6$ halocycloalkyl;

$R^f$ is selected from Cl, F, Br, $OCH_3$, $OC_2H_5$, $SCH_3$, $SC_2H_5$, CN, $CH_3$, $C_2H_5$, n-propyl, isopropyl, cyclopropyl, allyl, propargyl, $CF_3$, $CHF_2$, and $CF_2CF_3$.

In another more preferred embodiment the compounds of formula I are compounds of formula I-B, wherein $R^y$ is $CH_3$ or $C_2H_5$;

$R^1$ is selected from $CF_3$, $CF_2CF_3$, $CF(CF_3)_2$, $SCF_3$, $OCF_3$, $OCHF_2$, $S(=O)CF_3$, and $S(=O)_2CF_3$;

$R^2$ is selected from H, $CH_3$, and $C_2H_5$;

$R^3$ is selected from H, $CH_3$, and $C_2H_5$;

Ar is a phenyl or 5-6 membered heteroaryl substituted with $S(=O)_mR^e$ at the ortho position to bond connecting to 9-membered heteroaryl of compound of formula I, and optionally further substituted with 1 or 2 $R^{Ar}$, preferably selected from halogen, $C_1$-$C_6$ alkyl, $C_1$-$C_6$haloalkyl, $C_1$-$C_6$alkoxy, $C_1$-$C_6$ haloalkoxy, phenyl, and benzyl, wherein the phenyl ring of $R^{Ar}$ is unsubstituted or substituted by radicals $R^f$.

According to particularly preferred embodiment of the compound of formula I, compounds of the invention are the compounds of the formulae I-A and I-B that are compiled in the Tables 1-1 to 1-12 and Tables 2-1 to 2-12.

Table 1-1 Compounds of formula I-A in which X is O, $R^x$ is $CH_3$, $R^4$ is H and the meaning for the combination of $R^1$, $R^2$ and Ar for each individual compound corresponds in each case to one line of Table A.

Table 1-2 Compounds of formula I-A in which X is O, $R^x$ is $CH_3$, $R^4$ is $CH_3$ and the meaning for the combination of $R^1$, $R^2$ and Ar for each individual compound corresponds in each case to one line of Table A.

Table 1-3 Compounds of formula I-A in which X is O, $R^x$ is $CH_3$, $R^4$ is $C_2H_5$ and the meaning for the combination of $R^1$, $R^2$ and Ar for each individual compound corresponds in each case to one line of Table A.

Table 1-4 Compounds of formula I-A in which X is O, $R^x$ is $C_2H_5$, $R^4$ is H and the meaning for the combination of $R^1$, $R^2$ and Ar for each individual compound corresponds in each case to one line of Table A.

Table 1-5 Compounds of formula I-A in which X is O, $R^x$ is $C_2H_5$, $R^4$ is $CH_3$ and the meaning for the combination of $R^1$, $R^2$ and Ar for each individual compound corresponds in each case to one line of Table A.

Table 1-6 Compounds of formula I-A in which X is O, $R^x$ is $C_2H_5$, $R^4$ is $C_2H_5$ and the meaning for the combination of $R^1$, $R^2$ and Ar for each individual compound corresponds in each case to one line of Table A.

Table 1-7 Compounds of formula I-A in which X is S, $R^x$ is $CH_3$, $R^4$ is H and the meaning for the combination of $R^1$, $R^2$ and Ar for each individual compound corresponds in each case to one line of Table A.

Table 1-8 Compounds of formula I-A in which X is S, $R^x$ is $CH_3$, $R^4$ is $CH_3$ and the meaning for the combination of $R^1$, $R^2$ and Ar for each individual compound corresponds in each case to one line of Table A.

Table 1-9 Compounds of formula I-A in which X is S, $R^x$ is $CH_3$, $R^4$ is $C_2H_5$ and the meaning for the combination of $R^1$, $R^2$ and Ar for each individual compound corresponds in each case to one line of Table A.

Table 1-10 Compounds of formula I-A in which X is S, $R^x$ is $C_2H_5$, $R^4$ is H and the meaning for the combination of $R^1$, $R^2$ and Ar for each individual compound corresponds in each case to one line of Table A.

Table 1-11 Compounds of formula I-A in which X is S, $R^x$ is $C_2H_5$, $R^4$ is $CH_3$ and the meaning for the combination of $R^1$, $R^2$ and Ar for each individual compound corresponds in each case to one line of Table A.

Table 1-12 Compounds of formula I-A in which X is S, $R^x$ is $C_2H_5$, $R^4$ is $C_2H_5$ and the meaning for the combination of $R^1$, $R^2$ and Ar for each individual compound corresponds in each case to one line of Table A.

Table 2-1 Compounds of formula I-B in which X is O, $R^y$ is $CH_3$, $R^3$ is H and the meaning for the combination of $R^1$, $R^2$ and Ar for each individual compound corresponds in each case to one line of Table A.

Table 2-2 Compounds of formula I-B in which X is O, $R^y$ is $CH_3$, $R^3$ is $CH_3$ and the meaning for the combination of $R^1$, $R^2$ and Ar for each individual compound corresponds in each case to one line of Table A.

Table 2-3 Compounds of formula I-B in which X is O, $R^y$ is $CH_3$, $R^3$ is $C_2H_5$ and the meaning for the combination of $R^1$, $R^2$ and Ar for each individual compound corresponds in each case to one line of Table A.

Table 2-4 Compounds of formula I-B in which X is O, $R^y$ is $C_2H_5$, $R^3$ is H and the meaning for the combination of $R^1$, $R^2$ and Ar for each individual compound corresponds in each case to one line of Table A.

Table 2-5 Compounds of formula I-B in which X is O, $R^y$ is $C_2H_5$, $R^3$ is $CH_3$ and the meaning for the combination of $R^1$, $R^2$ and Ar for each individual compound corresponds in each case to one line of Table A.

Table 2-6 Compounds of formula I-B in which X is O, $R^y$ is $C_2H_5$, $R^3$ is $C_2H_5$ and the meaning for the combination of $R^1$, $R^2$ and Ar for each individual compound corresponds in each case to one line of Table A.

Table 2-7 Compounds of formula I-B in which X is S, $R^y$ is $CH_3$, $R^3$ is H and the meaning for the combination of $R^1$, $R^2$ and Ar for each individual compound corresponds in each case to one line of Table A.

Table 2-8 Compounds of formula I-B in which X is S, $R^y$ is $CH_3$, $R^3$ is $CH_3$ and the meaning for the combination of $R^1$, $R^2$ and Ar for each individual compound corresponds in each case to one line of Table A.

Table 2-9 Compounds of formula I-B in which X is S, $R^y$ is $CH_3$, $R^3$ is $C_2H_5$ and the meaning for the combination of $R^1$, $R^2$ and Ar for each individual compound corresponds in each case to one line of Table A.

Table 2-10 Compounds of formula I-B in which X is S, $R^y$ is $C_2H_5$, $R^3$ is H and the meaning for the combination of $R^1$, $R^2$ and Ar for each individual compound corresponds in each case to one line of Table A.

Table 2-11 Compounds of formula I-B in which X is S, $R^y$ is $C_2H_5$, $R^3$ is $CH_3$ and the meaning for the combination of $R^1$, $R^2$ and Ar for each individual compound corresponds in each case to one line of Table A.

Table 2-12 Compounds of formula I-B in which X is S, $R^y$ is $C_2H_5$, $R^3$ is $C_2H_5$ and the meaning for the combination of $R^1$, $R^2$ and Ar for each individual compound corresponds in each case to one line of Table A.

TABLE A

| Line | $R^1$ | $R^2$ | Ar |
| --- | --- | --- | --- |
| A-1 | $CF_3$ | H | Ar-1a |
| A-2 | $CF_3$ | H | Ar-1b |
| A-3 | $CF_3$ | H | Ar-1c |
| A-4 | $CF_3$ | H | Ar-1d |
| A-5 | $CF_3$ | H | Ar-1e |
| A-6 | $CF_3$ | H | Ar-1f |
| A-7 | $CF_3$ | H | Ar-2a |
| A-8 | $CF_3$ | H | Ar-2b |
| A-9 | $CF_3$ | H | Ar-2c |
| A-10 | $CF_3$ | H | Ar-2d |
| A-11 | $CF_3$ | H | Ar-2e |
| A-12 | $CF_3$ | H | Ar-2f |
| A-13 | $CF_3$ | H | Ar-3a |
| A-14 | $CF_3$ | H | Ar-3b |
| A-15 | $CF_3$ | H | Ar-3c |
| A-16 | $CF_3$ | H | Ar-4a |
| A-17 | $CF_3$ | H | Ar-4b |
| A-18 | $CF_3$ | H | Ar-4c |
| A-19 | $CF_3$ | H | Ar-4d |
| A-20 | $CF_3$ | H | Ar-4e |
| A-21 | $CF_3$ | H | Ar-4f |
| A-22 | $CF_3$ | H | Ar-6a |
| A-23 | $CF_3$ | H | Ar-6b |
| A-24 | $CF_3$ | H | Ar-6c |
| A-25 | $CF_3$ | H | Ar-8a |
| A-26 | $CF_3$ | H | Ar-8b |
| A-27 | $CF_3$ | H | Ar-8c |
| A-28 | $CF_3$ | H | Ar-9a |
| A-29 | $CF_3$ | H | Ar-9b |
| A-30 | $CF_3$ | H | Ar-9c |
| A-31 | $CF_3$ | H | Ar-10a |
| A-32 | $CF_3$ | H | Ar-10b |
| A-33 | $CF_3$ | H | Ar-10c |
| A-34 | $CF_3$ | H | Ar-10d |
| A-35 | $CF_3$ | H | Ar-10e |
| A-36 | $CF_3$ | H | Ar-10f |
| A-37 | $CF_3$ | H | Ar-10g |
| A-38 | $CF_3$ | H | Ar-10h |
| A-39 | $CF_3$ | H | Ar-10i |
| A-40 | $CF_3$ | H | Ar-10j |
| A-41 | $CF_3$ | $CH_3$ | Ar-1a |
| A-42 | $CF_3$ | $CH_3$ | Ar-1b |
| A-43 | $CF_3$ | $CH_3$ | Ar-1c |
| A-44 | $CF_3$ | $CH_3$ | Ar-1d |
| A-45 | $CF_3$ | $CH_3$ | Ar-1e |
| A-46 | $CF_3$ | $CH_3$ | Ar-1f |
| A-47 | $CF_3$ | $CH_3$ | Ar-2a |
| A-48 | $CF_3$ | $CH_3$ | Ar-2b |
| A-49 | $CF_3$ | $CH_3$ | Ar-2c |
| A-50 | $CF_3$ | $CH_3$ | Ar-2d |
| A-51 | $CF_3$ | $CH_3$ | Ar-2e |
| A-52 | $CF_3$ | $CH_3$ | Ar-2f |
| A-53 | $CF_3$ | $CH_3$ | Ar-3a |
| A-54 | $CF_3$ | $CH_3$ | Ar-3b |
| A-55 | $CF_3$ | $CH_3$ | Ar-3c |
| A-56 | $CF_3$ | $CH_3$ | Ar-4a |
| A-57 | $CF_3$ | $CH_3$ | Ar-4b |
| A-58 | $CF_3$ | $CH_3$ | Ar-4c |
| A-59 | $CF_3$ | $CH_3$ | Ar-4d |
| A-60 | $CF_3$ | $CH_3$ | Ar-4e |
| A-61 | $CF_3$ | $CH_3$ | Ar-4f |
| A-62 | $CF_3$ | $CH_3$ | Ar-6a |
| A-63 | $CF_3$ | $CH_3$ | Ar-6b |
| A-64 | $CF_3$ | $CH_3$ | Ar-6c |
| A-65 | $CF_3$ | $CH_3$ | Ar-8a |
| A-66 | $CF_3$ | $CH_3$ | Ar-8b |
| A-67 | $CF_3$ | $CH_3$ | Ar-8c |
| A-68 | $CF_3$ | $CH_3$ | Ar-9a |
| A-69 | $CF_3$ | $CH_3$ | Ar-9b |
| A-70 | $CF_3$ | $CH_3$ | Ar-9c |
| A-71 | $CF_3$ | $CH_3$ | Ar-10a |
| A-72 | $CF_3$ | $CH_3$ | Ar-10b |
| A-73 | $CF_3$ | $CH_3$ | Ar-10c |
| A-74 | $CF_3$ | $CH_3$ | Ar-10d |
| A-75 | $CF_3$ | $CH_3$ | Ar-10e |
| A-76 | $CF_3$ | $CH_3$ | Ar-10f |
| A-77 | $CF_3$ | $CH_3$ | Ar-10g |
| A-78 | $CF_3$ | $CH_3$ | Ar-10h |
| A-79 | $CF_3$ | $CH_3$ | Ar-10i |
| A-80 | $CF_3$ | $CH_3$ | Ar-10j |
| A-81 | $CF_3$ | $C_2H_5$ | Ar-1a |
| A-82 | $CF_3$ | $C_2H_5$ | Ar-1b |
| A-83 | $CF_3$ | $C_2H_5$ | Ar-1c |
| A-84 | $CF_3$ | $C_2H_5$ | Ar-1d |
| A-85 | $CF_3$ | $C_2H_5$ | Ar-1e |
| A-86 | $CF_3$ | $C_2H_5$ | Ar-1f |
| A-87 | $CF_3$ | $C_2H_5$ | Ar-2a |
| A-88 | $CF_3$ | $C_2H_5$ | Ar-2b |
| A-89 | $CF_3$ | $C_2H_5$ | Ar-2c |
| A-90 | $CF_3$ | $C_2H_5$ | Ar-2d |
| A-91 | $CF_3$ | $C_2H_5$ | Ar-2e |
| A-92 | $CF_3$ | $C_2H_5$ | Ar-2f |
| A-93 | $CF_3$ | $C_2H_5$ | Ar-3a |
| A-94 | $CF_3$ | $C_2H_5$ | Ar-3b |
| A-95 | $CF_3$ | $C_2H_5$ | Ar-3c |
| A-96 | $CF_3$ | $C_2H_5$ | Ar-4a |
| A-97 | $CF_3$ | $C_2H_5$ | Ar-4b |
| A-98 | $CF_3$ | $C_2H_5$ | Ar-4c |
| A-99 | $CF_3$ | $C_2H_5$ | Ar-4d |
| A-100 | $CF_3$ | $C_2H_5$ | Ar-4e |
| A-101 | $CF_3$ | $C_2H_5$ | Ar-4f |
| A-102 | $CF_3$ | $C_2H_5$ | Ar-6a |
| A-103 | $CF_3$ | $C_2H_5$ | Ar-6b |
| A-104 | $CF_3$ | $C_2H_5$ | Ar-6c |
| A-105 | $CF_3$ | $C_2H_5$ | Ar-8a |
| A-106 | $CF_3$ | $C_2H_5$ | Ar-8b |
| A-107 | $CF_3$ | $C_2H_5$ | Ar-8c |
| A-108 | $CF_3$ | $C_2H_5$ | Ar-9a |
| A-109 | $CF_3$ | $C_2H_5$ | Ar-9b |
| A-110 | $CF_3$ | $C_2H_5$ | Ar-9c |
| A-111 | $CF_3$ | $C_2H_5$ | Ar-10a |
| A-112 | $CF_3$ | $C_2H_5$ | Ar-10b |
| A-113 | $CF_3$ | $C_2H_5$ | Ar-10c |
| A-114 | $CF_3$ | $C_2H_5$ | Ar-10d |
| A-115 | $CF_3$ | $C_2H_5$ | Ar-10e |
| A-116 | $CF_3$ | $C_2H_5$ | Ar-10f |
| A-117 | $CF_3$ | $C_2H_5$ | Ar-10g |
| A-118 | $CF_3$ | $C_2H_5$ | Ar-10h |
| A-119 | $CF_3$ | $C_2H_5$ | Ar-10i |
| A-120 | $CF_3$ | $C_2H_5$ | Ar-10j |
| A-121 | $CF_2CF_3$ | H | Ar-1a |
| A-122 | $CF_2CF_3$ | H | Ar-1b |
| A-123 | $CF_2CF_3$ | H | Ar-1c |
| A-124 | $CF_2CF_3$ | H | Ar-1d |
| A-125 | $CF_2CF_3$ | H | Ar-1e |
| A-126 | $CF_2CF_3$ | H | Ar-1f |
| A-127 | $CF_2CF_3$ | H | Ar-2a |
| A-128 | $CF_2CF_3$ | H | Ar-2b |
| A-129 | $CF_2CF_3$ | H | Ar-2c |
| A-130 | $CF_2CF_3$ | H | Ar-2d |
| A-131 | $CF_2CF_3$ | H | Ar-2e |
| A-132 | $CF_2CF_3$ | H | Ar-2f |
| A-133 | $CF_2CF_3$ | H | Ar-3a |
| A-134 | $CF_2CF_3$ | H | Ar-3b |
| A-135 | $CF_2CF_3$ | H | Ar-3c |
| A-136 | $CF_2CF_3$ | H | Ar-4a |
| A-137 | $CF_2CF_3$ | H | Ar-4b |
| A-138 | $CF_2CF_3$ | H | Ar-4c |
| A-139 | $CF_2CF_3$ | H | Ar-4d |
| A-140 | $CF_2CF_3$ | H | Ar-4e |
| A-141 | $CF_2CF_3$ | H | Ar-4f |
| A-142 | $CF_2CF_3$ | H | Ar-6a |
| A-143 | $CF_2CF_3$ | H | Ar-6b |
| A-144 | $CF_2CF_3$ | H | Ar-6c |
| A-145 | $CF_2CF_3$ | H | Ar-8a |
| A-146 | $CF_2CF_3$ | H | Ar-8b |
| A-147 | $CF_2CF_3$ | H | Ar-8c |

TABLE A-continued

| Line | R¹ | R² | Ar |
|---|---|---|---|
| A-148 | CF$_2$CF$_3$ | H | Ar-9a |
| A-149 | CF$_2$CF$_3$ | H | Ar-9b |
| A-150 | CF$_2$CF$_3$ | H | Ar-9c |
| A-151 | CF$_2$CF$_3$ | H | Ar-10a |
| A-152 | CF$_2$CF$_3$ | H | Ar-10b |
| A-153 | CF$_2$CF$_3$ | H | Ar-10c |
| A-154 | CF$_2$CF$_3$ | H | Ar-10d |
| A-155 | CF$_2$CF$_3$ | H | Ar-10e |
| A-156 | CF$_2$CF$_3$ | H | Ar-10f |
| A-157 | CF$_2$CF$_3$ | H | Ar-10g |
| A-158 | CF$_2$CF$_3$ | H | Ar-10h |
| A-159 | CF$_2$CF$_3$ | H | Ar-10i |
| A-160 | CF$_2$CF$_3$ | H | Ar-10j |
| A-161 | CF$_2$CF$_3$ | CH$_3$ | Ar-1a |
| A-162 | CF$_2$CF$_3$ | CH$_3$ | Ar-1b |
| A-163 | CF$_2$CF$_3$ | CH$_3$ | Ar-1c |
| A-164 | CF$_2$CF$_3$ | CH$_3$ | Ar-1d |
| A-165 | CF$_2$CF$_3$ | CH$_3$ | Ar-1e |
| A-166 | CF$_2$CF$_3$ | CH$_3$ | Ar-1f |
| A-167 | CF$_2$CF$_3$ | CH$_3$ | Ar-2a |
| A-168 | CF$_2$CF$_3$ | CH$_3$ | Ar-2b |
| A-169 | CF$_2$CF$_3$ | CH$_3$ | Ar-2c |
| A-170 | CF$_2$CF$_3$ | CH$_3$ | Ar-2d |
| A-171 | CF$_2$CF$_3$ | CH$_3$ | Ar-2e |
| A-172 | CF$_2$CF$_3$ | CH$_3$ | Ar-2f |
| A-173 | CF$_2$CF$_3$ | CH$_3$ | Ar-3a |
| A-174 | CF$_2$CF$_3$ | CH$_3$ | Ar-3b |
| A-175 | CF$_2$CF$_3$ | CH$_3$ | Ar-3c |
| A-176 | CF$_2$CF$_3$ | CH$_3$ | Ar-4a |
| A-177 | CF$_2$CF$_3$ | CH$_3$ | Ar-4b |
| A-178 | CF$_2$CF$_3$ | CH$_3$ | Ar-4c |
| A-179 | CF$_2$CF$_3$ | CH$_3$ | Ar-4d |
| A-180 | CF$_2$CF$_3$ | CH$_3$ | Ar-4e |
| A-181 | CF$_2$CF$_3$ | CH$_3$ | Ar-4f |
| A-182 | CF$_2$CF$_3$ | CH$_3$ | Ar-6a |
| A-183 | CF$_2$CF$_3$ | CH$_3$ | Ar-6b |
| A-184 | CF$_2$CF$_3$ | CH$_3$ | Ar-6c |
| A-185 | CF$_2$CF$_3$ | CH$_3$ | Ar-8a |
| A-186 | CF$_2$CF$_3$ | CH$_3$ | Ar-8b |
| A-187 | CF$_2$CF$_3$ | CH$_3$ | Ar-8c |
| A-188 | CF$_2$CF$_3$ | CH$_3$ | Ar-9a |
| A-189 | CF$_2$CF$_3$ | CH$_3$ | Ar-9b |
| A-190 | CF$_2$CF$_3$ | CH$_3$ | Ar-9c |
| A-191 | CF$_2$CF$_3$ | CH$_3$ | Ar-10a |
| A-192 | CF$_2$CF$_3$ | CH$_3$ | Ar-10b |
| A-193 | CF$_2$CF$_3$ | CH$_3$ | Ar-10c |
| A-194 | CF$_2$CF$_3$ | CH$_3$ | Ar-10d |
| A-195 | CF$_2$CF$_3$ | CH$_3$ | Ar-10e |
| A-196 | CF$_2$CF$_3$ | CH$_3$ | Ar-10f |
| A-197 | CF$_2$CF$_3$ | CH$_3$ | Ar-10g |
| A-198 | CF$_2$CF$_3$ | CH$_3$ | Ar-10h |
| A-199 | CF$_2$CF$_3$ | CH$_3$ | Ar-10i |
| A-200 | CF$_2$CF$_3$ | CH$_3$ | Ar-10j |
| A-201 | CF$_2$CF$_3$ | C$_2$H$_5$ | Ar-1a |
| A-202 | CF$_2$CF$_3$ | C$_2$H$_5$ | Ar-1b |
| A-203 | CF$_2$CF$_3$ | C$_2$H$_5$ | Ar-1c |
| A-204 | CF$_2$CF$_3$ | C$_2$H$_5$ | Ar-1d |
| A-205 | CF$_2$CF$_3$ | C$_2$H$_5$ | Ar-1e |
| A-206 | CF$_2$CF$_3$ | C$_2$H$_5$ | Ar-1f |
| A-207 | CF$_2$CF$_3$ | C$_2$H$_5$ | Ar-2a |
| A-208 | CF$_2$CF$_3$ | C$_2$H$_5$ | Ar-2b |
| A-209 | CF$_2$CF$_3$ | C$_2$H$_5$ | Ar-2c |
| A-210 | CF$_2$CF$_3$ | C$_2$H$_5$ | Ar-2d |
| A-211 | CF$_2$CF$_3$ | C$_2$H$_5$ | Ar-2e |
| A-212 | CF$_2$CF$_3$ | C$_2$H$_5$ | Ar-2f |
| A-213 | CF$_2$CF$_3$ | C$_2$H$_5$ | Ar-3a |
| A-214 | CF$_2$CF$_3$ | C$_2$H$_5$ | Ar-3b |
| A-215 | CF$_2$CF$_3$ | C$_2$H$_5$ | Ar-3c |
| A-216 | CF$_2$CF$_3$ | C$_2$H$_5$ | Ar-4a |
| A-217 | CF$_2$CF$_3$ | C$_2$H$_5$ | Ar-4b |
| A-218 | CF$_2$CF$_3$ | C$_2$H$_5$ | Ar-4c |
| A-219 | CF$_2$CF$_3$ | C$_2$H$_5$ | Ar-4d |
| A-220 | CF$_2$CF$_3$ | C$_2$H$_5$ | Ar-4e |
| A-221 | CF$_2$CF$_3$ | C$_2$H$_5$ | Ar-4f |
| A-222 | CF$_2$CF$_3$ | C$_2$H$_5$ | Ar-6a |
| A-223 | CF$_2$CF$_3$ | C$_2$H$_5$ | Ar-6b |
| A-224 | CF$_2$CF$_3$ | C$_2$H$_5$ | Ar-6c |
| A-225 | CF$_2$CF$_3$ | C$_2$H$_5$ | Ar-8a |
| A-226 | CF$_2$CF$_3$ | C$_2$H$_5$ | Ar-8b |
| A-227 | CF$_2$CF$_3$ | C$_2$H$_5$ | Ar-8c |
| A-228 | CF$_2$CF$_3$ | C$_2$H$_5$ | Ar-9a |
| A-229 | CF$_2$CF$_3$ | C$_2$H$_5$ | Ar-9b |
| A-230 | CF$_2$CF$_3$ | C$_2$H$_5$ | Ar-9c |
| A-231 | CF$_2$CF$_3$ | C$_2$H$_5$ | Ar-10a |
| A-232 | CF$_2$CF$_3$ | C$_2$H$_5$ | Ar-10b |
| A-233 | CF$_2$CF$_3$ | C$_2$H$_5$ | Ar-10c |
| A-234 | CF$_2$CF$_3$ | C$_2$H$_5$ | Ar-10d |
| A-235 | CF$_2$CF$_3$ | C$_2$H$_5$ | Ar-10e |
| A-236 | CF$_2$CF$_3$ | C$_2$H$_5$ | Ar-10f |
| A-237 | CF$_2$CF$_3$ | C$_2$H$_5$ | Ar-10g |
| A-238 | CF$_2$CF$_3$ | C$_2$H$_5$ | Ar-10h |
| A-239 | CF$_2$CF$_3$ | C$_2$H$_5$ | Ar-10i |
| A-240 | CF$_2$CF$_3$ | C$_2$H$_5$ | Ar-10j |
| A-241 | CF(CF$_3$)$_2$ | H | Ar-1a |
| A-242 | CF(CF$_3$)$_2$ | H | Ar-1b |
| A-243 | CF(CF$_3$)$_2$ | H | Ar-1c |
| A-244 | CF(CF$_3$)$_2$ | H | Ar-1d |
| A-245 | CF(CF$_3$)$_2$ | H | Ar-1e |
| A-246 | CF(CF$_3$)$_2$ | H | Ar-1f |
| A-247 | CF(CF$_3$)$_2$ | H | Ar-2a |
| A-248 | CF(CF$_3$)$_2$ | H | Ar-2b |
| A-249 | CF(CF$_3$)$_2$ | H | Ar-2c |
| A-250 | CF(CF$_3$)$_2$ | H | Ar-2d |
| A-251 | CF(CF$_3$)$_2$ | H | Ar-2e |
| A-252 | CF(CF$_3$)$_2$ | H | Ar-2f |
| A-253 | CF(CF$_3$)$_2$ | H | Ar-3a |
| A-254 | CF(CF$_3$)$_2$ | H | Ar-3b |
| A-255 | CF(CF$_3$)$_2$ | H | Ar-3c |
| A-256 | CF(CF$_3$)$_2$ | H | Ar-4a |
| A-257 | CF(CF$_3$)$_2$ | H | Ar-4b |
| A-258 | CF(CF$_3$)$_2$ | H | Ar-4c |
| A-259 | CF(CF$_3$)$_2$ | H | Ar-4d |
| A-260 | CF(CF$_3$)$_2$ | H | Ar-4e |
| A-261 | CF(CF$_3$)$_2$ | H | Ar-4f |
| A-262 | CF(CF$_3$)$_2$ | H | Ar-6a |
| A-263 | CF(CF$_3$)$_2$ | H | Ar-6b |
| A-264 | CF(CF$_3$)$_2$ | H | Ar-6c |
| A-265 | CF(CF$_3$)$_2$ | H | Ar-8a |
| A-266 | CF(CF$_3$)$_2$ | H | Ar-8b |
| A-267 | CF(CF$_3$)$_2$ | H | Ar-8c |
| A-268 | CF(CF$_3$)$_2$ | H | Ar-9a |
| A-269 | CF(CF$_3$)$_2$ | H | Ar-9b |
| A-270 | CF(CF$_3$)$_2$ | H | Ar-9c |
| A-271 | CF(CF$_3$)$_2$ | H | Ar-10a |
| A-272 | CF(CF$_3$)$_2$ | H | Ar-10b |
| A-273 | CF(CF$_3$)$_2$ | H | Ar-10c |
| A-274 | CF(CF$_3$)$_2$ | H | Ar-10d |
| A-275 | CF(CF$_3$)$_2$ | H | Ar-10e |
| A-276 | CF(CF$_3$)$_2$ | H | Ar-10f |
| A-277 | CF(CF$_3$)$_2$ | H | Ar-10g |
| A-278 | CF(CF$_3$)$_2$ | H | Ar-10h |
| A-279 | CF(CF$_3$)$_2$ | H | Ar-10i |
| A-280 | CF(CF$_3$)$_2$ | H | Ar-10j |
| A-281 | CF(CF$_3$)$_2$ | CH$_3$ | Ar-1a |
| A-282 | CF(CF$_3$)$_2$ | CH$_3$ | Ar-1b |
| A-283 | CF(CF$_3$)$_2$ | CH$_3$ | Ar-1c |
| A-284 | CF(CF$_3$)$_2$ | CH$_3$ | Ar-1d |
| A-285 | CF(CF$_3$)$_2$ | CH$_3$ | Ar-1e |
| A-286 | CF(CF$_3$)$_2$ | CH$_3$ | Ar-1f |
| A-287 | CF(CF$_3$)$_2$ | CH$_3$ | Ar-2a |
| A-288 | CF(CF$_3$)$_2$ | CH$_3$ | Ar-2b |
| A-289 | CF(CF$_3$)$_2$ | CH$_3$ | Ar-2c |
| A-290 | CF(CF$_3$)$_2$ | CH$_3$ | Ar-2d |
| A-291 | CF(CF$_3$)$_2$ | CH$_3$ | Ar-2e |
| A-292 | CF(CF$_3$)$_2$ | CH$_3$ | Ar-2f |
| A-293 | CF(CF$_3$)$_2$ | CH$_3$ | Ar-3a |
| A-294 | CF(CF$_3$)$_2$ | CH$_3$ | Ar-3b |
| A-295 | CF(CF$_3$)$_2$ | CH$_3$ | Ar-3c |
| A-296 | CF(CF$_3$)$_2$ | CH$_3$ | Ar-4a |
| A-297 | CF(CF$_3$)$_2$ | CH$_3$ | Ar-4b |
| A-298 | CF(CF$_3$)$_2$ | CH$_3$ | Ar-4c |
| A-299 | CF(CF$_3$)$_2$ | CH$_3$ | Ar-4d |
| A-300 | CF(CF$_3$)$_2$ | CH$_3$ | Ar-4e |
| A-301 | CF(CF$_3$)$_2$ | CH$_3$ | Ar-4f |
| A-302 | CF(CF$_3$)$_2$ | CH$_3$ | Ar-6a |
| A-303 | CF(CF$_3$)$_2$ | CH$_3$ | Ar-6b |

TABLE A-continued

| Line | R¹ | R² | Ar |
|---|---|---|---|
| A-304 | CF(CF₃)₂ | CH₃ | Ar-6c |
| A-305 | CF(CF₃)₂ | CH₃ | Ar-8a |
| A-306 | CF(CF₃)₂ | CH₃ | Ar-8b |
| A-307 | CF(CF₃)₂ | CH₃ | Ar-8c |
| A-308 | CF(CF₃)₂ | CH₃ | Ar-9a |
| A-309 | CF(CF₃)₂ | CH₃ | Ar-9b |
| A-310 | CF(CF₃)₂ | CH₃ | Ar-9c |
| A-311 | CF(CF₃)₂ | CH₃ | Ar-10a |
| A-312 | CF(CF₃)₂ | CH₃ | Ar-10b |
| A-313 | CF(CF₃)₂ | CH₃ | Ar-10c |
| A-314 | CF(CF₃)₂ | CH₃ | Ar-10d |
| A-315 | CF(CF₃)₂ | CH₃ | Ar-10e |
| A-316 | CF(CF₃)₂ | CH₃ | Ar-10f |
| A-317 | CF(CF₃)₂ | CH₃ | Ar-10g |
| A-318 | CF(CF₃)₂ | CH₃ | Ar-10h |
| A-319 | CF(CF₃)₂ | CH₃ | Ar-10i |
| A-320 | CF(CF₃)₂ | CH₃ | Ar-10j |
| A-321 | CF(CF₃)₂ | C₂H₅ | Ar-1a |
| A-322 | CF(CF₃)₂ | C₂H₅ | Ar-1b |
| A-323 | CF(CF₃)₂ | C₂H₅ | Ar-1c |
| A-324 | CF(CF₃)₂ | C₂H₅ | Ar-1d |
| A-325 | CF(CF₃)₂ | C₂H₅ | Ar-1e |
| A-326 | CF(CF₃)₂ | C₂H₅ | Ar-1f |
| A-327 | CF(CF₃)₂ | C₂H₅ | Ar-2a |
| A-328 | CF(CF₃)₂ | C₂H₅ | Ar-2b |
| A-329 | CF(CF₃)₂ | C₂H₅ | Ar-2c |
| A-330 | CF(CF₃)₂ | C₂H₅ | Ar-2d |
| A-331 | CF(CF₃)₂ | C₂H₅ | Ar-2e |
| A-332 | CF(CF₃)₂ | C₂H₅ | Ar-2f |
| A-333 | CF(CF₃)₂ | C₂H₅ | Ar-3a |
| A-334 | CF(CF₃)₂ | C₂H₅ | Ar-3b |
| A-335 | CF(CF₃)₂ | C₂H₅ | Ar-3c |
| A-336 | CF(CF₃)₂ | C₂H₅ | Ar-4a |
| A-337 | CF(CF₃)₂ | C₂H₅ | Ar-4b |
| A-338 | CF(CF₃)₂ | C₂H₅ | Ar-4c |
| A-339 | CF(CF₃)₂ | C₂H₅ | Ar-4d |
| A-340 | CF(CF₃)₂ | C₂H₅ | Ar-4e |
| A-341 | CF(CF₃)₂ | C₂H₅ | Ar-4f |
| A-342 | CF(CF₃)₂ | C₂H₅ | Ar-6a |
| A-343 | CF(CF₃)₂ | C₂H₅ | Ar-6b |
| A-344 | CF(CF₃)₂ | C₂H₅ | Ar-6c |
| A-345 | CF(CF₃)₂ | C₂H₅ | Ar-8a |
| A-346 | CF(CF₃)₂ | C₂H₅ | Ar-8b |
| A-347 | CF(CF₃)₂ | C₂H₅ | Ar-8c |
| A-348 | CF(CF₃)₂ | C₂H₅ | Ar-9a |
| A-349 | CF(CF₃)₂ | C₂H₅ | Ar-9b |
| A-350 | CF(CF₃)₂ | C₂H₅ | Ar-9c |
| A-351 | CF(CF₃)₂ | C₂H₅ | Ar-10a |
| A-352 | CF(CF₃)₂ | C₂H₅ | Ar-10b |
| A-353 | CF(CF₃)₂ | C₂H₅ | Ar-10c |
| A-354 | CF(CF₃)₂ | C₂H₅ | Ar-10d |
| A-355 | CF(CF₃)₂ | C₂H₅ | Ar-10e |
| A-356 | CF(CF₃)₂ | C₂H₅ | Ar-10f |
| A-357 | CF(CF₃)₂ | C₂H₅ | Ar-10g |
| A-358 | CF(CF₃)₂ | C₂H₅ | Ar-10h |
| A-359 | CF(CF₃)₂ | C₂H₅ | Ar-10i |
| A-360 | CF(CF₃)₂ | C₂H₅ | Ar-10j |
| A-361 | SCF₃ | H | Ar-1a |
| A-362 | SCF₃ | H | Ar-1b |
| A-363 | SCF₃ | H | Ar-1c |
| A-364 | SCF₃ | H | Ar-1d |
| A-365 | SCF₃ | H | Ar-1e |
| A-366 | SCF₃ | H | Ar-1f |
| A-367 | SCF₃ | H | Ar-2a |
| A-368 | SCF₃ | H | Ar-2b |
| A-369 | SCF₃ | H | Ar-2c |
| A-370 | SCF₃ | H | Ar-2d |
| A-371 | SCF₃ | H | Ar-2e |
| A-372 | SCF₃ | H | Ar-2f |
| A-373 | SCF₃ | H | Ar-3a |
| A-374 | SCF₃ | H | Ar-3b |
| A-375 | SCF₃ | H | Ar-3c |
| A-376 | SCF₃ | H | Ar-4a |
| A-377 | SCF₃ | H | Ar-4b |
| A-378 | SCF₃ | H | Ar-4c |
| A-379 | SCF₃ | H | Ar-4d |
| A-380 | SCF₃ | H | Ar-4e |
| A-381 | SCF₃ | H | Ar-4f |
| A-382 | SCF₃ | H | Ar-6a |
| A-383 | SCF₃ | H | Ar-6b |
| A-384 | SCF₃ | H | Ar-6c |
| A-385 | SCF₃ | H | Ar-8a |
| A-386 | SCF₃ | H | Ar-8b |
| A-387 | SCF₃ | H | Ar-8c |
| A-388 | SCF₃ | H | Ar-9a |
| A-389 | SCF₃ | H | Ar-9b |
| A-390 | SCF₃ | H | Ar-9c |
| A-391 | SCF₃ | H | Ar-10a |
| A-392 | SCF₃ | H | Ar-10b |
| A-393 | SCF₃ | H | Ar-10c |
| A-394 | SCF₃ | H | Ar-10d |
| A-395 | SCF₃ | H | Ar-10e |
| A-396 | SCF₃ | H | Ar-10f |
| A-397 | SCF₃ | H | Ar-10g |
| A-398 | SCF₃ | H | Ar-10h |
| A-399 | SCF₃ | H | Ar-10i |
| A-400 | SCF₃ | H | Ar-10j |
| A-401 | SCF₃ | CH₃ | Ar-1a |
| A-402 | SCF₃ | CH₃ | Ar-1b |
| A-403 | SCF₃ | CH₃ | Ar-1c |
| A-404 | SCF₃ | CH₃ | Ar-1d |
| A-405 | SCF₃ | CH₃ | Ar-1e |
| A-406 | SCF₃ | CH₃ | Ar-1f |
| A-407 | SCF₃ | CH₃ | Ar-2a |
| A-408 | SCF₃ | CH₃ | Ar-2b |
| A-409 | SCF₃ | CH₃ | Ar-2c |
| A-410 | SCF₃ | CH₃ | Ar-2d |
| A-411 | SCF₃ | CH₃ | Ar-2e |
| A-412 | SCF₃ | CH₃ | Ar-2f |
| A-413 | SCF₃ | CH₃ | Ar-3a |
| A-414 | SCF₃ | CH₃ | Ar-3b |
| A-415 | SCF₃ | CH₃ | Ar-3c |
| A-416 | SCF₃ | CH₃ | Ar-4a |
| A-417 | SCF₃ | CH₃ | Ar-4b |
| A-418 | SCF₃ | CH₃ | Ar-4c |
| A-419 | SCF₃ | CH₃ | Ar-4d |
| A-420 | SCF₃ | CH₃ | Ar-4e |
| A-421 | SCF₃ | CH₃ | Ar-4f |
| A-422 | SCF₃ | CH₃ | Ar-6a |
| A-423 | SCF₃ | CH₃ | Ar-6b |
| A-424 | SCF₃ | CH₃ | Ar-6c |
| A-425 | SCF₃ | CH₃ | Ar-8a |
| A-426 | SCF₃ | CH₃ | Ar-8b |
| A-427 | SCF₃ | CH₃ | Ar-8c |
| A-428 | SCF₃ | CH₃ | Ar-9a |
| A-429 | SCF₃ | CH₃ | Ar-9b |
| A-430 | SCF₃ | CH₃ | Ar-9c |
| A-431 | SCF₃ | CH₃ | Ar-10a |
| A-432 | SCF₃ | CH₃ | Ar-10b |
| A-433 | SCF₃ | CH₃ | Ar-10c |
| A-434 | SCF₃ | CH₃ | Ar-10d |
| A-435 | SCF₃ | CH₃ | Ar-10e |
| A-436 | SCF₃ | CH₃ | Ar-10f |
| A-437 | SCF₃ | CH₃ | Ar-10g |
| A-438 | SCF₃ | CH₃ | Ar-10h |
| A-439 | SCF₃ | CH₃ | Ar-10i |
| A-440 | SCF₃ | CH₃ | Ar-10j |
| A-441 | SCF₃ | C₂H₅ | Ar-1a |
| A-442 | SCF₃ | C₂H₅ | Ar-1b |
| A-443 | SCF₃ | C₂H₅ | Ar-1c |
| A-444 | SCF₃ | C₂H₅ | Ar-1d |
| A-445 | SCF₃ | C₂H₅ | Ar-1e |
| A-446 | SCF₃ | C₂H₅ | Ar-1f |
| A-447 | SCF₃ | C₂H₅ | Ar-2a |
| A-448 | SCF₃ | C₂H₅ | Ar-2b |
| A-449 | SCF₃ | C₂H₅ | Ar-2c |
| A-450 | SCF₃ | C₂H₅ | Ar-2d |
| A-451 | SCF₃ | C₂H₅ | Ar-2e |
| A-452 | SCF₃ | C₂H₅ | Ar-2f |
| A-453 | SCF₃ | C₂H₅ | Ar-3a |
| A-454 | SCF₃ | C₂H₅ | Ar-3b |
| A-455 | SCF₃ | C₂H₅ | Ar-3c |
| A-456 | SCF₃ | C₂H₅ | Ar-4a |
| A-457 | SCF₃ | C₂H₅ | Ar-4b |
| A-458 | SCF₃ | C₂H₅ | Ar-4c |
| A-459 | SCF₃ | C₂H₅ | Ar-4d |

TABLE A-continued

| Line | R¹ | R² | Ar |
|---|---|---|---|
| A-460 | SCF₃ | C₂H₅ | Ar-4e |
| A-461 | SCF₃ | C₂H₅ | Ar-4f |
| A-462 | SCF₃ | C₂H₅ | Ar-6a |
| A-463 | SCF₃ | C₂H₅ | Ar-6b |
| A-464 | SCF₃ | C₂H₅ | Ar-6c |
| A-465 | SCF₃ | C₂H₅ | Ar-8a |
| A-466 | SCF₃ | C₂H₅ | Ar-8b |
| A-467 | SCF₃ | C₂H₅ | Ar-8c |
| A-468 | SCF₃ | C₂H₅ | Ar-9a |
| A-469 | SCF₃ | C₂H₅ | Ar-9b |
| A-470 | SCF₃ | C₂H₅ | Ar-9c |
| A-471 | SCF₃ | C₂H₅ | Ar-10a |
| A-472 | SCF₃ | C₂H₅ | Ar-10b |
| A-473 | SCF₃ | C₂H₅ | Ar-10c |
| A-474 | SCF₃ | C₂H₅ | Ar-10d |
| A-475 | SCF₃ | C₂H₅ | Ar-10e |
| A-476 | SCF₃ | C₂H₅ | Ar-10f |
| A-477 | SCF₃ | C₂H₅ | Ar-10g |
| A-478 | SCF₃ | C₂H₅ | Ar-10h |
| A-479 | SCF₃ | C₂H₅ | Ar-10i |
| A-480 | SCF₃ | C₂H₅ | Ar-10j |
| A-481 | OCF₃ | H | Ar-1a |
| A-482 | OCF₃ | H | Ar-1b |
| A-483 | OCF₃ | H | Ar-1c |
| A-484 | OCF₃ | H | Ar-1d |
| A-485 | OCF₃ | H | Ar-1e |
| A-486 | OCF₃ | H | Ar-1f |
| A-487 | OCF₃ | H | Ar-2a |
| A-488 | OCF₃ | H | Ar-2b |
| A-489 | OCF₃ | H | Ar-2c |
| A-490 | OCF₃ | H | Ar-2d |
| A-491 | OCF₃ | H | Ar-2e |
| A-492 | OCF₃ | H | Ar-2f |
| A-493 | OCF₃ | H | Ar-3a |
| A-494 | OCF₃ | H | Ar-3b |
| A-495 | OCF₃ | H | Ar-3c |
| A-496 | OCF₃ | H | Ar-4a |
| A-497 | OCF₃ | H | Ar-4b |
| A-498 | OCF₃ | H | Ar-4c |
| A-499 | OCF₃ | H | Ar-4d |
| A-500 | OCF₃ | H | Ar-4e |
| A-501 | OCF₃ | H | Ar-4f |
| A-502 | OCF₃ | H | Ar-6a |
| A-503 | OCF₃ | H | Ar-6b |
| A-504 | OCF₃ | H | Ar-6c |
| A-505 | OCF₃ | H | Ar-8a |
| A-506 | OCF₃ | H | Ar-8b |
| A-507 | OCF₃ | H | Ar-8c |
| A-508 | OCF₃ | H | Ar-9a |
| A-509 | OCF₃ | H | Ar-9b |
| A-510 | OCF₃ | H | Ar-9c |
| A-511 | OCF₃ | H | Ar-10a |
| A-512 | OCF₃ | H | Ar-10b |
| A-513 | OCF₃ | H | Ar-10c |
| A-514 | OCF₃ | H | Ar-10d |
| A-515 | OCF₃ | H | Ar-10e |
| A-516 | OCF₃ | H | Ar-10f |
| A-517 | OCF₃ | H | Ar-10g |
| A-518 | OCF₃ | H | Ar-10h |
| A-519 | OCF₃ | H | Ar-10i |
| A-520 | OCF₃ | H | Ar-10j |
| A-521 | OCF₃ | CH₃ | Ar-1a |
| A-522 | OCF₃ | CH₃ | Ar-1b |
| A-523 | OCF₃ | CH₃ | Ar-1c |
| A-524 | OCF₃ | CH₃ | Ar-1d |
| A-525 | OCF₃ | CH₃ | Ar-1e |
| A-526 | OCF₃ | CH₃ | Ar-1f |
| A-527 | OCF₃ | CH₃ | Ar-2a |
| A-528 | OCF₃ | CH₃ | Ar-2b |
| A-529 | OCF₃ | CH₃ | Ar-2c |
| A-530 | OCF₃ | CH₃ | Ar-2d |
| A-531 | OCF₃ | CH₃ | Ar-2e |
| A-532 | OCF₃ | CH₃ | Ar-2f |
| A-533 | OCF₃ | CH₃ | Ar-3a |
| A-534 | OCF₃ | CH₃ | Ar-3b |
| A-535 | OCF₃ | CH₃ | Ar-3c |
| A-536 | OCF₃ | CH₃ | Ar-4a |
| A-537 | OCF₃ | CH₃ | Ar-4b |
| A-538 | OCF₃ | CH₃ | Ar-4c |
| A-539 | OCF₃ | CH₃ | Ar-4d |
| A-540 | OCF₃ | CH₃ | Ar-4e |
| A-541 | OCF₃ | CH₃ | Ar-4f |
| A-542 | OCF₃ | CH₃ | Ar-6a |
| A-543 | OCF₃ | CH₃ | Ar-6b |
| A-544 | OCF₃ | CH₃ | Ar-6c |
| A-545 | OCF₃ | CH₃ | Ar-8a |
| A-546 | OCF₃ | CH₃ | Ar-8b |
| A-547 | OCF₃ | CH₃ | Ar-8c |
| A-548 | OCF₃ | CH₃ | Ar-9a |
| A-549 | OCF₃ | CH₃ | Ar-9b |
| A-550 | OCF₃ | CH₃ | Ar-9c |
| A-551 | OCF₃ | CH₃ | Ar-10a |
| A-552 | OCF₃ | CH₃ | Ar-10b |
| A-553 | OCF₃ | CH₃ | Ar-10c |
| A-554 | OCF₃ | CH₃ | Ar-10d |
| A-555 | OCF₃ | CH₃ | Ar-10e |
| A-556 | OCF₃ | CH₃ | Ar-10f |
| A-557 | OCF₃ | CH₃ | Ar-10g |
| A-558 | OCF₃ | CH₃ | Ar-10h |
| A-559 | OCF₃ | CH₃ | Ar-10i |
| A-560 | OCF₃ | CH₃ | Ar-10j |
| A-561 | OCF₃ | C₂H₅ | Ar-1a |
| A-562 | OCF₃ | C₂H₅ | Ar-1b |
| A-563 | OCF₃ | C₂H₅ | Ar-1c |
| A-564 | OCF₃ | C₂H₅ | Ar-1d |
| A-565 | OCF₃ | C₂H₅ | Ar-1e |
| A-566 | OCF₃ | C₂H₅ | Ar-1f |
| A-567 | OCF₃ | C₂H₅ | Ar-2a |
| A-568 | OCF₃ | C₂H₅ | Ar-2b |
| A-569 | OCF₃ | C₂H₅ | Ar-2c |
| A-570 | OCF₃ | C₂H₅ | Ar-2d |
| A-571 | OCF₃ | C₂H₅ | Ar-2e |
| A-572 | OCF₃ | C₂H₅ | Ar-2f |
| A-573 | OCF₃ | C₂H₅ | Ar-3a |
| A-574 | OCF₃ | C₂H₅ | Ar-3b |
| A-575 | OCF₃ | C₂H₅ | Ar-3c |
| A-576 | OCF₃ | C₂H₅ | Ar-4a |
| A-577 | OCF₃ | C₂H₅ | Ar-4b |
| A-578 | OCF₃ | C₂H₅ | Ar-4c |
| A-579 | OCF₃ | C₂H₅ | Ar-4d |
| A-580 | OCF₃ | C₂H₅ | Ar-4e |
| A-581 | OCF₃ | C₂H₅ | Ar-4f |
| A-582 | OCF₃ | C₂H₅ | Ar-6a |
| A-583 | OCF₃ | C₂H₅ | Ar-6b |
| A-584 | OCF₃ | C₂H₅ | Ar-6c |
| A-585 | OCF₃ | C₂H₅ | Ar-8a |
| A-586 | OCF₃ | C₂H₅ | Ar-8b |
| A-587 | OCF₃ | C₂H₅ | Ar-8c |
| A-588 | OCF₃ | C₂H₅ | Ar-9a |
| A-589 | OCF₃ | C₂H₅ | Ar-9b |
| A-590 | OCF₃ | C₂H₅ | Ar-9c |
| A-591 | OCF₃ | C₂H₅ | Ar-10a |
| A-592 | OCF₃ | C₂H₅ | Ar-10b |
| A-593 | OCF₃ | C₂H₅ | Ar-10c |
| A-594 | OCF₃ | C₂H₅ | Ar-10d |
| A-595 | OCF₃ | C₂H₅ | Ar-10e |
| A-596 | OCF₃ | C₂H₅ | Ar-10f |
| A-597 | OCF₃ | C₂H₅ | Ar-10g |
| A-598 | OCF₃ | C₂H₅ | Ar-10h |
| A-599 | OCF₃ | C₂H₅ | Ar-10i |
| A-600 | OCF₃ | C₂H₅ | Ar-10j |
| A-601 | OCHF₂ | H | Ar-1a |
| A-602 | OCHF₂ | H | Ar-1b |
| A-603 | OCHF₂ | H | Ar-1c |
| A-604 | OCHF₂ | H | Ar-1d |
| A-605 | OCHF₂ | H | Ar-1e |
| A-606 | OCHF₂ | H | Ar-1f |
| A-607 | OCHF₂ | H | Ar-2a |
| A-608 | OCHF₂ | H | Ar-2b |
| A-609 | OCHF₂ | H | Ar-2c |
| A-610 | OCHF₂ | H | Ar-2d |
| A-611 | OCHF₂ | H | Ar-2e |
| A-612 | OCHF₂ | H | Ar-2f |
| A-613 | OCHF₂ | H | Ar-3a |
| A-614 | OCHF₂ | H | Ar-3b |
| A-615 | OCHF₂ | H | Ar-3c |

TABLE A-continued

| Line | R¹ | R² | Ar |
|---|---|---|---|
| A-616 | OCHF$_2$ | H | Ar-4a |
| A-617 | OCHF$_2$ | H | Ar-4b |
| A-618 | OCHF$_2$ | H | Ar-4c |
| A-619 | OCHF$_2$ | H | Ar-4d |
| A-620 | OCHF$_2$ | H | Ar-4e |
| A-621 | OCHF$_2$ | H | Ar-4f |
| A-622 | OCHF$_2$ | H | Ar-6a |
| A-623 | OCHF$_2$ | H | Ar-6b |
| A-624 | OCHF$_2$ | H | Ar-6c |
| A-625 | OCHF$_2$ | H | Ar-8a |
| A-626 | OCHF$_2$ | H | Ar-8b |
| A-627 | OCHF$_2$ | H | Ar-8c |
| A-628 | OCHF$_2$ | H | Ar-9a |
| A-629 | OCHF$_2$ | H | Ar-9b |
| A-630 | OCHF$_2$ | H | Ar-9c |
| A-631 | OCHF$_2$ | H | Ar-10a |
| A-632 | OCHF$_2$ | H | Ar-10b |
| A-633 | OCHF$_2$ | H | Ar-10c |
| A-634 | OCHF$_2$ | H | Ar-10d |
| A-635 | OCHF$_2$ | H | Ar-10e |
| A-636 | OCHF$_2$ | H | Ar-10f |
| A-637 | OCHF$_2$ | H | Ar-10g |
| A-638 | OCHF$_2$ | H | Ar-10h |
| A-639 | OCHF$_2$ | H | Ar-10i |
| A-640 | OCHF$_2$ | H | Ar-10j |
| A-641 | OCHF$_2$ | CH$_3$ | Ar-1a |
| A-642 | OCHF$_2$ | CH$_3$ | Ar-1b |
| A-643 | OCHF$_2$ | CH$_3$ | Ar-1c |
| A-644 | OCHF$_2$ | CH$_3$ | Ar-1d |
| A-645 | OCHF$_2$ | CH$_3$ | Ar-1e |
| A-646 | OCHF$_2$ | CH$_3$ | Ar-1f |
| A-647 | OCHF$_2$ | CH$_3$ | Ar-2a |
| A-648 | OCHF$_2$ | CH$_3$ | Ar-2b |
| A-649 | OCHF$_2$ | CH$_3$ | Ar-2c |
| A-650 | OCHF$_2$ | CH$_3$ | Ar-2d |
| A-651 | OCHF$_2$ | CH$_3$ | Ar-2e |
| A-652 | OCHF$_2$ | CH$_3$ | Ar-2f |
| A-653 | OCHF$_2$ | CH$_3$ | Ar-3a |
| A-654 | OCHF$_2$ | CH$_3$ | Ar-3b |
| A-655 | OCHF$_2$ | CH$_3$ | Ar-3c |
| A-656 | OCHF$_2$ | CH$_3$ | Ar-4a |
| A-657 | OCHF$_2$ | CH$_3$ | Ar-4b |
| A-658 | OCHF$_2$ | CH$_3$ | Ar-4c |
| A-659 | OCHF$_2$ | CH$_3$ | Ar-4d |
| A-660 | OCHF$_2$ | CH$_3$ | Ar-4e |
| A-661 | OCHF$_2$ | CH$_3$ | Ar-4f |
| A-662 | OCHF$_2$ | CH$_3$ | Ar-6a |
| A-663 | OCHF$_2$ | CH$_3$ | Ar-6b |
| A-664 | OCHF$_2$ | CH$_3$ | Ar-6c |
| A-665 | OCHF$_2$ | CH$_3$ | Ar-8a |
| A-666 | OCHF$_2$ | CH$_3$ | Ar-8b |
| A-667 | OCHF$_2$ | CH$_3$ | Ar-8c |
| A-668 | OCHF$_2$ | CH$_3$ | Ar-9a |
| A-669 | OCHF$_2$ | CH$_3$ | Ar-9b |
| A-670 | OCHF$_2$ | CH$_3$ | Ar-9c |
| A-671 | OCHF$_2$ | CH$_3$ | Ar-10a |
| A-672 | OCHF$_2$ | CH$_3$ | Ar-10b |
| A-673 | OCHF$_2$ | CH$_3$ | Ar-10c |
| A-674 | OCHF$_2$ | CH$_3$ | Ar-10d |
| A-675 | OCHF$_2$ | CH$_3$ | Ar-10e |
| A-676 | OCHF$_2$ | CH$_3$ | Ar-10f |
| A-677 | OCHF$_2$ | CH$_3$ | Ar-10g |
| A-678 | OCHF$_2$ | CH$_3$ | Ar-10h |
| A-679 | OCHF$_2$ | CH$_3$ | Ar-10i |
| A-680 | OCHF$_2$ | CH$_3$ | Ar-10j |
| A-681 | OCHF$_2$ | C$_2$H$_5$ | Ar-1a |
| A-682 | OCHF$_2$ | C$_2$H$_5$ | Ar-1b |
| A-683 | OCHF$_2$ | C$_2$H$_5$ | Ar-1c |
| A-684 | OCHF$_2$ | C$_2$H$_5$ | Ar-1d |
| A-685 | OCHF$_2$ | C$_2$H$_5$ | Ar-1e |
| A-686 | OCHF$_2$ | C$_2$H$_5$ | Ar-1f |
| A-687 | OCHF$_2$ | C$_2$H$_5$ | Ar-2a |
| A-688 | OCHF$_2$ | C$_2$H$_5$ | Ar-2b |
| A-689 | OCHF$_2$ | C$_2$H$_5$ | Ar-2c |
| A-690 | OCHF$_2$ | C$_2$H$_5$ | Ar-2d |
| A-691 | OCHF$_2$ | C$_2$H$_5$ | Ar-2e |
| A-692 | OCHF$_2$ | C$_2$H$_5$ | Ar-2f |
| A-693 | OCHF$_2$ | C$_2$H$_5$ | Ar-3a |
| A-694 | OCHF$_2$ | C$_2$H$_5$ | Ar-3b |
| A-695 | OCHF$_2$ | C$_2$H$_5$ | Ar-3c |
| A-696 | OCHF$_2$ | C$_2$H$_5$ | Ar-4a |
| A-697 | OCHF$_2$ | C$_2$H$_5$ | Ar-4b |
| A-698 | OCHF$_2$ | C$_2$H$_5$ | Ar-4c |
| A-699 | OCHF$_2$ | C$_2$H$_5$ | Ar-4d |
| A-700 | OCHF$_2$ | C$_2$H$_5$ | Ar-4e |
| A-701 | OCHF$_2$ | C$_2$H$_5$ | Ar-4f |
| A-702 | OCHF$_2$ | C$_2$H$_5$ | Ar-6a |
| A-703 | OCHF$_2$ | C$_2$H$_5$ | Ar-6b |
| A-704 | OCHF$_2$ | C$_2$H$_5$ | Ar-6c |
| A-705 | OCHF$_2$ | C$_2$H$_5$ | Ar-8a |
| A-706 | OCHF$_2$ | C$_2$H$_5$ | Ar-8b |
| A-707 | OCHF$_2$ | C$_2$H$_5$ | Ar-8c |
| A-708 | OCHF$_2$ | C$_2$H$_5$ | Ar-9a |
| A-709 | OCHF$_2$ | C$_2$H$_5$ | Ar-9b |
| A-710 | OCHF$_2$ | C$_2$H$_5$ | Ar-9c |
| A-711 | OCHF$_2$ | C$_2$H$_5$ | Ar-10a |
| A-712 | OCHF$_2$ | C$_2$H$_5$ | Ar-10b |
| A-713 | OCHF$_2$ | C$_2$H$_5$ | Ar-10c |
| A-714 | OCHF$_2$ | C$_2$H$_5$ | Ar-10d |
| A-715 | OCHF$_2$ | C$_2$H$_5$ | Ar-10e |
| A-716 | OCHF$_2$ | C$_2$H$_5$ | Ar-10f |
| A-717 | OCHF$_2$ | C$_2$H$_5$ | Ar-10g |
| A-718 | OCHF$_2$ | C$_2$H$_5$ | Ar-10h |
| A-719 | OCHF$_2$ | C$_2$H$_5$ | Ar-10i |
| A-720 | OCHF$_2$ | C$_2$H$_5$ | Ar-10j |
| A-721 | S(=O)CF$_3$ | H | Ar-1a |
| A-722 | S(=O)CF$_3$ | H | Ar-1b |
| A-723 | S(=O)CF$_3$ | H | Ar-1c |
| A-724 | S(=O)CF$_3$ | H | Ar-1d |
| A-725 | S(=O)CF$_3$ | H | Ar-1e |
| A-726 | S(=O)CF$_3$ | H | Ar-1f |
| A-727 | S(=O)CF$_3$ | H | Ar-2a |
| A-728 | S(=O)CF$_3$ | H | Ar-2b |
| A-729 | S(=O)CF$_3$ | H | Ar-2c |
| A-730 | S(=O)CF$_3$ | H | Ar-2d |
| A-731 | S(=O)CF$_3$ | H | Ar-2e |
| A-732 | S(=O)CF$_3$ | H | Ar-2f |
| A-733 | S(=O)CF$_3$ | H | Ar-3a |
| A-734 | S(=O)CF$_3$ | H | Ar-3b |
| A-735 | S(=O)CF$_3$ | H | Ar-3c |
| A-736 | S(=O)CF$_3$ | H | Ar-4a |
| A-737 | S(=O)CF$_3$ | H | Ar-4b |
| A-738 | S(=O)CF$_3$ | H | Ar-4c |
| A-739 | S(=O)CF$_3$ | H | Ar-4d |
| A-740 | S(=O)CF$_3$ | H | Ar-4e |
| A-741 | S(=O)CF$_3$ | H | Ar-4f |
| A-742 | S(=O)CF$_3$ | H | Ar-6a |
| A-743 | S(=O)CF$_3$ | H | Ar-6b |
| A-744 | S(=O)CF$_3$ | H | Ar-6c |
| A-745 | S(=O)CF$_3$ | H | Ar-8a |
| A-746 | S(=O)CF$_3$ | H | Ar-8b |
| A-747 | S(=O)CF$_3$ | H | Ar-8c |
| A-748 | S(=O)CF$_3$ | H | Ar-9a |
| A-749 | S(=O)CF$_3$ | H | Ar-9b |
| A-750 | S(=O)CF$_3$ | H | Ar-9c |
| A-751 | S(=O)CF$_3$ | H | Ar-10a |
| A-752 | S(=O)CF$_3$ | H | Ar-10b |
| A-753 | S(=O)CF$_3$ | H | Ar-10c |
| A-754 | S(=O)CF$_3$ | H | Ar-10d |
| A-755 | S(=O)CF$_3$ | H | Ar-10e |
| A-756 | S(=O)CF$_3$ | H | Ar-10f |
| A-757 | S(=O)CF$_3$ | H | Ar-10g |
| A-758 | S(=O)CF$_3$ | H | Ar-10h |
| A-759 | S(=O)CF$_3$ | H | Ar-10i |
| A-760 | S(=O)CF$_3$ | H | Ar-10j |
| A-761 | S(=O)CF$_3$ | CH$_3$ | Ar-1a |
| A-762 | S(=O)CF$_3$ | CH$_3$ | Ar-1b |
| A-763 | S(=O)CF$_3$ | CH$_3$ | Ar-1c |
| A-764 | S(=O)CF$_3$ | CH$_3$ | Ar-1d |
| A-765 | S(=O)CF$_3$ | CH$_3$ | Ar-1e |
| A-766 | S(=O)CF$_3$ | CH$_3$ | Ar-1f |
| A-767 | S(=O)CF$_3$ | CH$_3$ | Ar-2a |
| A-768 | S(=O)CF$_3$ | CH$_3$ | Ar-2b |
| A-769 | S(=O)CF$_3$ | CH$_3$ | Ar-2c |
| A-770 | S(=O)CF$_3$ | CH$_3$ | Ar-2d |
| A-771 | S(=O)CF$_3$ | CH$_3$ | Ar-2e |

TABLE A-continued

| Line | R¹ | R² | Ar |
|---|---|---|---|
| A-772 | S(=O)CF$_3$ | CH$_3$ | Ar-2f |
| A-773 | S(=O)CF$_3$ | CH$_3$ | Ar-3a |
| A-774 | S(=O)CF$_3$ | CH$_3$ | Ar-3b |
| A-775 | S(=O)CF$_3$ | CH$_3$ | Ar-3c |
| A-776 | S(=O)CF$_3$ | CH$_3$ | Ar-4a |
| A-777 | S(=O)CF$_3$ | CH$_3$ | Ar-4b |
| A-778 | S(=O)CF$_3$ | CH$_3$ | Ar-4c |
| A-779 | S(=O)CF$_3$ | CH$_3$ | Ar-4d |
| A-780 | S(=O)CF$_3$ | CH$_3$ | Ar-4e |
| A-781 | S(=O)CF$_3$ | CH$_3$ | Ar-4f |
| A-782 | S(=O)CF$_3$ | CH$_3$ | Ar-6a |
| A-783 | S(=O)CF$_3$ | CH$_3$ | Ar-6b |
| A-784 | S(=O)CF$_3$ | CH$_3$ | Ar-6c |
| A-785 | S(=O)CF$_3$ | CH$_3$ | Ar-8a |
| A-786 | S(=O)CF$_3$ | CH$_3$ | Ar-8b |
| A-787 | S(=O)CF$_3$ | CH$_3$ | Ar-8c |
| A-788 | S(=O)CF$_3$ | CH$_3$ | Ar-9a |
| A-789 | S(=O)CF$_3$ | CH$_3$ | Ar-9b |
| A-790 | S(=O)CF$_3$ | CH$_3$ | Ar-9c |
| A-791 | S(=O)CF$_3$ | CH$_3$ | Ar-10a |
| A-792 | S(=O)CF$_3$ | CH$_3$ | Ar-10b |
| A-793 | S(=O)CF$_3$ | CH$_3$ | Ar-10c |
| A-794 | S(=O)CF$_3$ | CH$_3$ | Ar-10d |
| A-795 | S(=O)CF$_3$ | CH$_3$ | Ar-10e |
| A-796 | S(=O)CF$_3$ | CH$_3$ | Ar-10f |
| A-797 | S(=O)CF$_3$ | CH$_3$ | Ar-10g |
| A-798 | S(=O)CF$_3$ | CH$_3$ | Ar-10h |
| A-799 | S(=O)CF$_3$ | CH$_3$ | Ar-10i |
| A-800 | S(=O)CF$_3$ | CH$_3$ | Ar-10j |
| A-801 | S(=O)CF$_3$ | C$_2$H$_5$ | Ar-1a |
| A-802 | S(=O)CF$_3$ | C$_2$H$_5$ | Ar-1b |
| A-803 | S(=O)CF$_3$ | C$_2$H$_5$ | Ar-1c |
| A-804 | S(=O)CF$_3$ | C$_2$H$_5$ | Ar-1d |
| A-805 | S(=O)CF$_3$ | C$_2$H$_5$ | Ar-1e |
| A-806 | S(=O)CF$_3$ | C$_2$H$_5$ | Ar-1f |
| A-807 | S(=O)CF$_3$ | C$_2$H$_5$ | Ar-2a |
| A-808 | S(=O)CF$_3$ | C$_2$H$_5$ | Ar-2b |
| A-809 | S(=O)CF$_3$ | C$_2$H$_5$ | Ar-2c |
| A-810 | S(=O)CF$_3$ | C$_2$H$_5$ | Ar-2d |
| A-811 | S(=O)CF$_3$ | C$_2$H$_5$ | Ar-2e |
| A-812 | S(=O)CF$_3$ | C$_2$H$_5$ | Ar-2f |
| A-813 | S(=O)CF$_3$ | C$_2$H$_5$ | Ar-3a |
| A-814 | S(=O)CF$_3$ | C$_2$H$_5$ | Ar-3b |
| A-815 | S(=O)CF$_3$ | C$_2$H$_5$ | Ar-3c |
| A-816 | S(=O)CF$_3$ | C$_2$H$_5$ | Ar-4a |
| A-817 | S(=O)CF$_3$ | C$_2$H$_5$ | Ar-4b |
| A-818 | S(=O)CF$_3$ | C$_2$H$_5$ | Ar-4c |
| A-819 | S(=O)CF$_3$ | C$_2$H$_5$ | Ar-4d |
| A-820 | S(=O)CF$_3$ | C$_2$H$_5$ | Ar-4e |
| A-821 | S(=O)CF$_3$ | C$_2$H$_5$ | Ar-4f |
| A-822 | S(=O)CF$_3$ | C$_2$H$_5$ | Ar-6a |
| A-823 | S(=O)CF$_3$ | C$_2$H$_5$ | Ar-6b |
| A-824 | S(=O)CF$_3$ | C$_2$H$_5$ | Ar-6c |
| A-825 | S(=O)CF$_3$ | C$_2$H$_5$ | Ar-8a |
| A-826 | S(=O)CF$_3$ | C$_2$H$_5$ | Ar-8b |
| A-827 | S(=O)CF$_3$ | C$_2$H$_5$ | Ar-8c |
| A-828 | S(=O)CF$_3$ | C$_2$H$_5$ | Ar-9a |
| A-829 | S(=O)CF$_3$ | C$_2$H$_5$ | Ar-9b |
| A-830 | S(=O)CF$_3$ | C$_2$H$_5$ | Ar-9c |
| A-831 | S(=O)CF$_3$ | C$_2$H$_5$ | Ar-10a |
| A-832 | S(=O)CF$_3$ | C$_2$H$_5$ | Ar-10b |
| A-833 | S(=O)CF$_3$ | C$_2$H$_5$ | Ar-10c |
| A-834 | S(=O)CF$_3$ | C$_2$H$_5$ | Ar-10d |
| A-835 | S(=O)CF$_3$ | C$_2$H$_5$ | Ar-10e |
| A-836 | S(=O)CF$_3$ | C$_2$H$_5$ | Ar-10f |
| A-837 | S(=O)CF$_3$ | C$_2$H$_5$ | Ar-10g |
| A-838 | S(=O)CF$_3$ | C$_2$H$_5$ | Ar-10h |
| A-839 | S(=O)CF$_3$ | C$_2$H$_5$ | Ar-10i |
| A-840 | S(=O)CF$_3$ | C$_2$H$_5$ | Ar-10j |
| A-841 | S(=O)$_2$CF$_3$ | H | Ar-1a |
| A-842 | S(=O)$_2$CF$_3$ | H | Ar-1b |
| A-843 | S(=O)$_2$CF$_3$ | H | Ar-1c |
| A-844 | S(=O)$_2$CF$_3$ | H | Ar-1d |
| A-845 | S(=O)$_2$CF$_3$ | H | Ar-1e |
| A-846 | S(=O)$_2$CF$_3$ | H | Ar-1f |
| A-847 | S(=O)$_2$CF$_3$ | H | Ar-2a |
| A-848 | S(=O)$_2$CF$_3$ | H | Ar-2b |
| A-849 | S(=O)$_2$CF$_3$ | H | Ar-2c |
| A-850 | S(=O)$_2$CF$_3$ | H | Ar-2d |
| A-851 | S(=O)$_2$CF$_3$ | H | Ar-2e |
| A-852 | S(=O)$_2$CF$_3$ | H | Ar-2f |
| A-853 | S(=O)$_2$CF$_3$ | H | Ar-3a |
| A-854 | S(=O)$_2$CF$_3$ | H | Ar-3b |
| A-855 | S(=O)$_2$CF$_3$ | H | Ar-3c |
| A-856 | S(=O)$_2$CF$_3$ | H | Ar-4a |
| A-857 | S(=O)$_2$CF$_3$ | H | Ar-4b |
| A-858 | S(=O)$_2$CF$_3$ | H | Ar-4c |
| A-859 | S(=O)$_2$CF$_3$ | H | Ar-4d |
| A-860 | S(=O)$_2$CF$_3$ | H | Ar-4e |
| A-861 | S(=O)$_2$CF$_3$ | H | Ar-4f |
| A-862 | S(=O)$_2$CF$_3$ | H | Ar-6a |
| A-863 | S(=O)$_2$CF$_3$ | H | Ar-6b |
| A-864 | S(=O)$_2$CF$_3$ | H | Ar-6c |
| A-865 | S(=O)$_2$CF$_3$ | H | Ar-8a |
| A-866 | S(=O)$_2$CF$_3$ | H | Ar-8b |
| A-867 | S(=O)$_2$CF$_3$ | H | Ar-8c |
| A-868 | S(=O)$_2$CF$_3$ | H | Ar-9a |
| A-869 | S(=O)$_2$CF$_3$ | H | Ar-9b |
| A-870 | S(=O)$_2$CF$_3$ | H | Ar-9c |
| A-871 | S(=O)$_2$CF$_3$ | H | Ar-10a |
| A-872 | S(=O)$_2$CF$_3$ | H | Ar-10b |
| A-873 | S(=O)$_2$CF$_3$ | H | Ar-10c |
| A-874 | S(=O)$_2$CF$_3$ | H | Ar-10d |
| A-875 | S(=O)$_2$CF$_3$ | H | Ar-10e |
| A-876 | S(=O)$_2$CF$_3$ | H | Ar-10f |
| A-877 | S(=O)$_2$CF$_3$ | H | Ar-10g |
| A-878 | S(=O)$_2$CF$_3$ | H | Ar-10h |
| A-879 | S(=O)$_2$CF$_3$ | H | Ar-10i |
| A-880 | S(=O)$_2$CF$_3$ | H | Ar-10j |
| A-881 | S(=O)$_2$CF$_3$ | CH$_3$ | Ar-1a |
| A-882 | S(=O)$_2$CF$_3$ | CH$_3$ | Ar-1b |
| A-883 | S(=O)$_2$CF$_3$ | CH$_3$ | Ar-1c |
| A-884 | S(=O)$_2$CF$_3$ | CH$_3$ | Ar-1d |
| A-885 | S(=O)$_2$CF$_3$ | CH$_3$ | Ar-1e |
| A-886 | S(=O)$_2$CF$_3$ | CH$_3$ | Ar-1f |
| A-887 | S(=O)$_2$CF$_3$ | CH$_3$ | Ar-2a |
| A-888 | S(=O)$_2$CF$_3$ | CH$_3$ | Ar-2b |
| A-889 | S(=O)$_2$CF$_3$ | CH$_3$ | Ar-2c |
| A-890 | S(=O)$_2$CF$_3$ | CH$_3$ | Ar-2d |
| A-891 | S(=O)$_2$CF$_3$ | CH$_3$ | Ar-2e |
| A-892 | S(=O)$_2$CF$_3$ | CH$_3$ | Ar-2f |
| A-893 | S(=O)$_2$CF$_3$ | CH$_3$ | Ar-3a |
| A-894 | S(=O)$_2$CF$_3$ | CH$_3$ | Ar-3b |
| A-895 | S(=O)$_2$CF$_3$ | CH$_3$ | Ar-3c |
| A-896 | S(=O)$_2$CF$_3$ | CH$_3$ | Ar-4a |
| A-897 | S(=O)$_2$CF$_3$ | CH$_3$ | Ar-4b |
| A-898 | S(=O)$_2$CF$_3$ | CH$_3$ | Ar-4c |
| A-899 | S(=O)$_2$CF$_3$ | CH$_3$ | Ar-4d |
| A-900 | S(=O)$_2$CF$_3$ | CH$_3$ | Ar-4e |
| A-901 | S(=O)$_2$CF$_3$ | CH$_3$ | Ar-4f |
| A-902 | S(=O)$_2$CF$_3$ | CH$_3$ | Ar-6a |
| A-903 | S(=O)$_2$CF$_3$ | CH$_3$ | Ar-6b |
| A-904 | S(=O)$_2$CF$_3$ | CH$_3$ | Ar-6c |
| A-905 | S(=O)$_2$CF$_3$ | CH$_3$ | Ar-8a |
| A-906 | S(=O)$_2$CF$_3$ | CH$_3$ | Ar-8b |
| A-907 | S(=O)$_2$CF$_3$ | CH$_3$ | Ar-8c |
| A-908 | S(=O)$_2$CF$_3$ | CH$_3$ | Ar-9a |
| A-909 | S(=O)$_2$CF$_3$ | CH$_3$ | Ar-9b |
| A-910 | S(=O)$_2$CF$_3$ | CH$_3$ | Ar-9c |
| A-911 | S(=O)$_2$CF$_3$ | CH$_3$ | Ar-10a |
| A-912 | S(=O)$_2$CF$_3$ | CH$_3$ | Ar-10b |
| A-913 | S(=O)$_2$CF$_3$ | CH$_3$ | Ar-10c |
| A-914 | S(=O)$_2$CF$_3$ | CH$_3$ | Ar-10d |
| A-915 | S(=O)$_2$CF$_3$ | CH$_3$ | Ar-10e |
| A-916 | S(=O)$_2$CF$_3$ | CH$_3$ | Ar-10f |
| A-917 | S(=O)$_2$CF$_3$ | CH$_3$ | Ar-10g |
| A-918 | S(=O)$_2$CF$_3$ | CH$_3$ | Ar-10h |
| A-919 | S(=O)$_2$CF$_3$ | CH$_3$ | Ar-10i |
| A-920 | S(=O)$_2$CF$_3$ | CH$_3$ | Ar-10j |
| A-921 | S(=O)$_2$CF$_3$ | C$_2$H$_5$ | Ar-1a |
| A-922 | S(=O)$_2$CF$_3$ | C$_2$H$_5$ | Ar-1b |
| A-923 | S(=O)$_2$CF$_3$ | C$_2$H$_5$ | Ar-1c |
| A-924 | S(=O)$_2$CF$_3$ | C$_2$H$_5$ | Ar-1d |
| A-925 | S(=O)$_2$CF$_3$ | C$_2$H$_5$ | Ar-1e |
| A-926 | S(=O)$_2$CF$_3$ | C$_2$H$_5$ | Ar-1f |
| A-927 | S(=O)$_2$CF$_3$ | C$_2$H$_5$ | Ar-2a |

TABLE A-continued

| Line | R¹ | R² | Ar |
|---|---|---|---|
| A-928 | S(=O)$_2$CF$_3$ | C$_2$H$_5$ | Ar-2b |
| A-929 | S(=O)$_2$CF$_3$ | C$_2$H$_5$ | Ar-2c |
| A-930 | S(=O)$_2$CF$_3$ | C$_2$H$_5$ | Ar-2d |
| A-931 | S(=O)$_2$CF$_3$ | C$_2$H$_5$ | Ar-2e |
| A-932 | S(=O)$_2$CF$_3$ | C$_2$H$_5$ | Ar-2f |
| A-933 | S(=O)$_2$CF$_3$ | C$_2$H$_5$ | Ar-3a |
| A-934 | S(=O)$_2$CF$_3$ | C$_2$H$_5$ | Ar-3b |
| A-935 | S(=O)$_2$CF$_3$ | C$_2$H$_5$ | Ar-3c |
| A-936 | S(=O)$_2$CF$_3$ | C$_2$H$_5$ | Ar-4a |
| A-937 | S(=O)$_2$CF$_3$ | C$_2$H$_5$ | Ar-4b |
| A-938 | S(=O)$_2$CF$_3$ | C$_2$H$_5$ | Ar-4c |
| A-939 | S(=O)$_2$CF$_3$ | C$_2$H$_5$ | Ar-4d |
| A-940 | S(=O)$_2$CF$_3$ | C$_2$H$_5$ | Ar-4e |
| A-941 | S(=O)$_2$CF$_3$ | C$_2$H$_5$ | Ar-4f |
| A-942 | S(=O)$_2$CF$_3$ | C$_2$H$_5$ | Ar-6a |
| A-943 | S(=O)$_2$CF$_3$ | C$_2$H$_5$ | Ar-6b |
| A-944 | S(=O)$_2$CF$_3$ | C$_2$H$_5$ | Ar-6c |
| A-945 | S(=O)$_2$CF$_3$ | C$_2$H$_5$ | Ar-8a |
| A-946 | S(=O)$_2$CF$_3$ | C$_2$H$_5$ | Ar-8b |
| A-947 | S(=O)$_2$CF$_3$ | C$_2$H$_5$ | Ar-8c |
| A-948 | S(=O)$_2$CF$_3$ | C$_2$H$_5$ | Ar-9a |
| A-949 | S(=O)$_2$CF$_3$ | C$_2$H$_5$ | Ar-9b |
| A-950 | S(=O)$_2$CF$_3$ | C$_2$H$_5$ | Ar-9c |
| A-951 | S(=O)$_2$CF$_3$ | C$_2$H$_5$ | Ar-10a |
| A-952 | S(=O)$_2$CF$_3$ | C$_2$H$_5$ | Ar-10b |
| A-953 | S(=O)$_2$CF$_3$ | C$_2$H$_5$ | Ar-10c |
| A-954 | S(=O)$_2$CF$_3$ | C$_2$H$_5$ | Ar-10d |
| A-955 | S(=O)$_2$CF$_3$ | C$_2$H$_5$ | Ar-10e |
| A-956 | S(=O)$_2$CF$_3$ | C$_2$H$_5$ | Ar-10f |
| A-957 | S(=O)$_2$CF$_3$ | C$_2$H$_5$ | Ar-10g |
| A-958 | S(=O)$_2$CF$_3$ | C$_2$H$_5$ | Ar-10h |
| A-959 | S(=O)$_2$CF$_3$ | C$_2$H$_5$ | Ar-10i |
| A-960 | S(=O)$_2$CF$_3$ | C$_2$H$_5$ | Ar-10j |

As used herein, the term "compound(s) of the present invention" or "compound(s) according to the invention" refers to the compound(s) of formula (I) as defined above, which are also referred to as "compound(s) of formula I" or "compound(s) I" or "formula I compound(s)", and includes their salts, tautomers, stereoisomers, and N-oxides.

The present invention also relates to a mixture of at least one compound of the present invention with at least one mixing partner as defined herein after. Preferred are binary mixtures of one compound of the present invention as component I with one mixing partner as defined herein after as component II. Preferred weight ratios for such binary mixtures are from 5000:1 to 1:5000, preferably from 1000:1 to 1:1000, more preferably from 100:1 to 1:100, particularly preferably from 10:1 to 1:10. In such binary mixtures, components I and II may be used in equal amounts, or an excess of component I, or an excess of component II may be used.

Mixing partners can be selected from pesticides, in particular insecticides, nematicides, and acaricides, fungicides, herbicides, plant growth regulators, fertilizers, and the like. Preferred mixing partners are insecticides, nematicides and fungicides.

The following list M of pesticides, grouped and numbered according the Mode of Action Classification of the Insecticide Resistance Action Committee (IRAC), together with which the compounds of the present invention can be used and with which potential synergistic effects might be produced, is intended to illustrate the possible combinations, but not to impose any limitation:

M.1 Acetylcholine esterase (AChE) inhibitors from the class of: M.1A carbamates, for example aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or from the class of M.1B organophosphates, for example acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos- methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;

M.2. GABA-gated chloride channel antagonists such as: M.2A cyclodiene organochlorine compounds, as for example endosulfan or chlordane; or M.2B fiproles (phenylpyrazoles), as for example ethiprole, fipronil, flufiprole, pyrafluprole and pyriprole;

M.3 Sodium channel modulators from the class of M.3A pyrethroids, for example acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, heptafluthrin, imiprothrin, meperfluthrin, metofluthrin, momfluorothrin, permethrin, phenothrin, prallethrin, profluthrin, pyrethrin (pyrethrum), resmethrin, silafluofen, tefluthrin, tetramethylfluthrin, tetramethrin, tralomethrin and transfluthrin; or M.3B sodium channel modulators such as DDT or methoxychlor;

M.4 Nicotinic acetylcholine receptor agonists (nAChR) from the class of M.4A neonicotinoids, for example acetamiprid, clothianidin, cycloxaprid, dinotefuran, imidacloprid, nitenpyram, thiacloprid and thiamethoxam; or the compounds M.4A.2: (2E+1-[(6-Chloropyridin-3-yl)methyl]-N'-nitro-2-pentylidenehydrazinecarboximidamide; or M4.A.3: 1-[(6-Chloropyridin-3-yl)methyl]-7-methyl-8-nitro-5-propoxy-1,2,3,5,6,7-hexahydroimidazo[1,2-a]pyridine; or from the class M.4B nicotine;

M.5 Nicotinic acetylcholine receptor allosteric activators from the class of spinosyns, for example spinosad or spinetoram;

M.6 Chloride channel activators from the class of avermectins and milbemycins, for example abamectin, emamectin benzoate, ivermectin, lepimectin or milbemectin;

M.7 Juvenile hormone mimics, such as M.7A juvenile hormone analogues as hydroprene, kinoprene and methoprene; or others as M.7B fenoxycarb or M.7C pyriproxyfen;

M.8 miscellaneous non-specific (multi-site) inhibitors, for example M.8A alkyl halides as methyl bromide and other alkyl halides, or M.8B chloropicrin, or M.8C sulfuryl fluoride, or M.8D borax, or M.8E tartar emetic;

M.9 Selective homopteran feeding blockers, for example M.9B pymetrozine, or M.9C flonicamid;

M.10 Mite growth inhibitors, for example M.10A clofentezine, hexythiazox and diflovidazin, or M.10B etoxazole;

M.11 Microbial disruptors of insect midgut membranes, for example *Bacillus thuringiensis* or *Bacillus sphaericus* and the insecticdal proteins they produce such as *Bacillus thuringiensis* subsp. israelensis, *Bacillus sphaericus*, *Bacillus thuringiensis* subsp. aizawai, *Bacillus thuringiensis* subsp. kurstaki and *Bacillus thuringiensis* subsp. tenebrionis, or the Bt crop proteins: Cry1Ab, Cry1Ac, Cry1Fa, Cry2Ab, mCry3A, Cry3Ab, Cry3Bb and Cry34/35Ab1;

M.12 Inhibitors of mitochondrial ATP synthase, for example M.12A diafenthiuron, or M.126 organotin miticides such as azocyclotin, cyhexatin or fenbutatin oxide, or M.12C propargite, or M.12D tetradifon;

M.13 Uncouplers of oxidative phosphorylation via disruption of the proton gradient, for example chlorfenapyr, DNOC or sulfluramid;

M.14 Nicotinic acetylcholine receptor (nAChR) channel blockers, for example nereistoxin analogues as bensultap, cartap hydrochloride, thiocyclam or thiosultap sodium;

M.15 Inhibitors of the chitin biosynthesis type 0, such as benzoylureas as for example bistrifluron, chlorfluazuron, diflubenzuron, flucycloxuron, flufenoxuron, hexaflumuron, lufenuron, novaluron, noviflumuron, teflubenzuron or triflumuron;

M.16 Inhibitors of the chitin biosynthesis type 1, as for example buprofezin;

M.17 Moulting disruptors, Dipteran, as for example cyromazine;

M.18 Ecdyson receptor agonists such as diacylhydrazines, for example methoxyfenozide, tebufenozide, halofenozide, fufenozide or chromafenozide;

M.19 Octopamin receptor agonists, as for example amitraz;

M.20 Mitochondrial complex III electron transport inhibitors, for example M.20A hydramethylnon, or M.20B acequinocyl, or M.20C fluacrypyrim;

M.21 Mitochondrial complex I electron transport inhibitors, for example M.21A METI acaricides and insecticides such as fenazaquin, fenpyroximate, pyrimidifen, pyridaben, tebufenpyrad or tolfenpyrad, or M.21B rotenone;

M.22 Voltage-dependent sodium channel blockers, for example M.22A indoxacarb, or M.22B metaflumizone, or M.22B.1: 242-(4-Cyanophenyl)-1-[3-(trifluoromethyl)phenyl]ethylidene]-N-[4-(difluoromethoxy)phenyl]-hydrazinecarboxamide or M.22.2: N-(3-Chloro-2-methylphenyl)-2-[(4-chlorophenyl)[4-[methyl(methylsulfonyl)amino]phenyl]methylene]-hydrazinecarboxamide;

M.23 Inhibitors of the of acetyl CoA carboxylase, such as Tetronic and Tetramic acid derivatives, for example spirodiclofen, spiromesifen or spirotetramat;

M.24 Mitochondrial complex IV electron transport inhibitors, for example M.24A phosphine such as aluminium phosphide, calcium phosphide, phosphine or zinc phosphide, or M.24B cyanide;

M.25 Mitochondrial complex II electron transport inhibitors, such as beta-ketonitrile derivatives, for example cyenopyrafen or cyflumetofen;

M.28 Ryanodine receptor-modulators from the class of diamides, as for example flubendiamide, chlorantraniliprole (Rynaxypyr®), cyantraniliprole (Cyazypyr®), tetraniliprole, or the phthalamide compounds M.28.1: (R)-3-Chlor-N1-{2-methyl-4[1,2,2,2-tetrafluor-1-(trifluormethypethyl]phenyl}-N2-(1-methyl-2-methylsulfonylethyl)phthalamid and M.28.2: (S)-3-Chlor-N1-{2-methyl-4-[1,2,2,2-tetrafluor-1-(trifluormethypethyl]phenyl}-N2-(1-methyl-2-methylsulfonylethyl)phthalamid, or the compound M.28.3: 3-bromo-N-{2-bromo-4-chloro-6-[(1-cyclopropylethyl)carbamoyl]phenyl}-1-(3-chlorpyridin-2-yl)-1H-pyrazole-5-carboxamide (proposed ISO name: cyclaniliprole), or the compound M.28.4: methyl-2-[43,5-dibromo-2-({[3-bromo-1-(3-chlorpyridin-2-yl)-1H-pyrazol-5-yl]carbonyl]amino)benzoyl]-1,2-dimethylhydrazinecarboxylate; or a compound selected from M.28.5a) to M.28.5d) and M.28.5h) to M.28.51): M.28.5a) N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide; M.28.5b) N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide; M.28.5c) N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide; M.28.5d) N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide; M.28.5h) N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide; M.28.5i) N-[2-(5-Amino-1,3,4-thiadiazol-2-yl)-4-chloro-6-methylphenyl]-3-bromo-1-(3-chloro-2-pyridinyl)-1H-pyrazole-5-carboxamide; M.28.5j) 3-Chloro-1-(3-chloro-2-pyridinyl)-N-[2,4-dichloro-6-[[(1-cyano-1-methylethyl)amino]carbonyl]phenyl]-1H-pyrazole-5-carboxamide; M.28.5k) 3-Bromo-N-[2,4-dichloro-6-(methylcarbamoyl)phenyl]-1-(3,5-dichloro-2-pyridyl)-1H-pyrazole-5-carboxamide; M.28.5l) N-[4-Chloro-2-[[(1,1-dimethylethyl)amino]carbonyl]-6-methylphenyl]-1-(3-chloro-2-pyridinyl)-3-(fluoromethoxy)-1H-pyrazole-5-carboxamide; or M.28.6: cyhalodiamide; or;

M.29. insecticidal active compounds of unknown or uncertain mode of action, as for example afidopyropen, afoxolaner, azadirachtin, amidoflumet, benzoximate, bifenazate, broflanilide, bromopropylate, chinomethionat, cryolite, dicloromezotiaz, dicofol, flufenerim, flometoquin, fluensulfone, fluhexafon, fluopyram, flupyradifurone, fluralaner, metoxadiazone, piperonyl butoxide, pyflubumide, pyridalyl, pyrifluquinazon, sulfoxaflor, tioxazafen, triflumezopyrim, or the compounds M.29.3: 11-(4-chloro-2,6-dimethylphenyl)-12-hydroxy-1,4-dioxa-9-azadispiro[4.2.4.2]-tetradec-11-en-10-one, or the compound M.29.4: 3-(4'-fluoro-2,4-dimethylbiphenyl-3-yl)-4-hydroxy-8-oxa-1-azaspiro[4.5]dec-3-en-2-one, or the compound M.29.5: 142-fluoro-4-methyl-5-[(2,2,2-trifluoroethyl)sulfinyl]phenyl]-3-(trifluoromethyl)-1H-1,2,4-triazole-5-amine, or actives on basis of *Bacillus firmus* (Votivo, 1-1582); or a compound selected from the group of M.29.6, wherein the compound is selected from M.29.6a) to M.29.6k): M.29.6a) (E/Z)-N-[1-[(6-chloro-3-pyridyl)methyl]-2-pyridylidene]-2,2,2-trifluoro-acetamide; M.29.6b) (E/Z)-N-[1-[(6-chloro-5-fluoro-3-pyridyl)methyl]-2-pyridylidene]-2,2,2-trifluoro-acetamide; M.29.6c) (E/Z)-2,2,2-trifluoro-N-[1-[(6-fluoro-3-pyridyl)methyl]-2-pyridylidene]acetamide; M.29.6d) (E/Z)-N-[1-[(6-bromo-3-pyridyl)methyl]-2-pyridylidene]-2,2,2-trifluoro-acetamide; M.29.6e) (E/Z)-N-[1-[1-(6-chloro-3-pyridyethyl]-2-pyridylidene]-2,2,2-trifluoro-acetamide; M.29.6f) (E/Z)-N-[1-[(6-chloro-3-pyridyl)methyl]-2-pyridylidene]-2,2-difluoro-acetamide; M.29.6g) (E/Z)-2-chloro-N-[1-[(6-chloro-3-pyridyl)methyl]-2-pyridylidene]-2,2-difluoro-acetamide; M.29.6h) (E/Z)-N-[1-[(2-chloro-pyrimidin-5-yl)methyl]-2-pyridylidene]-2,2,2-trifluoro-acetamide; M.29.6i) (E/Z)-N-[1-[(6-chloro-3-pyridyl)methyl]-2-pyridylidene]-2,2,3,3,3-pentafluoropropanamide.); M.29.6j) N-[1-[(6-chloro-3-pyridyl)methyl]-2-pyridylidene]-2,2,2-trifluoro-thioacetamide; or M.29.6k) N-[1-[(6-chloro-3-pyridyl)methyl]-2-pyridylidene]-2,2,2-trifluoro-N'-isopropyl-acetamidine; or the compounds M.29.8: fluazaindolizine; or the compounds M.29.9.a): 4[5-(3,5-dichlorophenyl)-5-(trifluoromethyl)-4H-isoxazol-3-yl]-2-methyl-N-(1-oxothietan-3-yl)benzamide; or M.29.9.b): fluxametamide; or M.29.10: 5[3-[2,6-dichloro-4-(3,3-dichloroallyloxy)phenoxy]propoxy]-1H-pyrazole; or a compound selected from the group of M.29.11, wherein the compound is selected from M.29.11b) to M.29.11p): M.29.11.b) 3-(benzoylmethylamino)-N-[2-bromo-4-[1,2,2,3,3,3-hexafluoro-1-(trifluoromethyl)propyl]-6-(trifluoromethyl)phenyl]-2-fluoro-benzamide; M.29.11.c) 3-(benzoyl-methylamino)-2-fluoro-N-[2-iodo-4-[1,2,2,2-tetrafluoro-1-(trifluoromethypethyl]-6-(trifluoromethyl)phenyl]-benzamide; M.29.11.d) N-[3-[[[2-iodo-4-[1,2,2,2-tetrafluoro-1-(trifluoromethypethyl]-6-(trifluoromethyl)phenyl]amino]carbonyl]phenyl]-N-methyl-benzamide; M.29.11.e) N-[3-[[[2-bromo-4-[1,2,2,2-tetrafluoro-1-(trifluoromethypethyl]-6-(trifluoromethyl)phenyl]amino]carbonyl]-2-fluorophenyl]-4-fluoro-N-methyl-benzamide; M.29.11.f) 4-fluoro-N-[2-fluoro-3-E2-iodo-4-[1,2,2,2-tetrafluoro-1-(trifluoromethypethyl)-6-(trifluoromethyl)phenyl]amino]carbonyl]phenyl]-N-methyl-benzamide; M.29.11.g) 3-fluoro-N-[2-fluoro-3-[[[2-iodo-4-[1,2,2,2-tetrafluoro-1-(trifluoromethypethyl]-6-(trifluoromethyl)phenyl]amino]carbonyl]phenyl]-N-methyl-benzamide; M.29.11.h) 2-chloro-N-[3-[[[2-iodo-4-[1,2,2,2-tetrafluoro-1-(trifluoromethypethyl]-6-(trifluoromethyl)phenyl]amino]carbonyl]phenyl]-3-pyridinecarboxamide; M.29.11.i) 4-cyano-N-[2-cyano-5-[[2,6-dibromo-4-[1,2,2,3,3,3-hexafluoro-1-(trifluoromethyl)propyl]phenyl]carbamoyl]phenyl]-2-methyl-benzamide; M.29.11.j) 4-cyano-3-[(4-cyano-2-methyl-benzoyl)amino]-N-[2,6-dichloro-4-[1,2,2,3,3,3-hexafluoro-1-(trifluoromethyl)propyl]phenyl]-2-fluoro-benzamide; M.29.11.k) N-[5-[[2-chloro-6-cyano-4-[1,2,2,3,3,3-hexafluoro-1-(trifluoromethyl)propyl]phenyl]carbamoyl]-2-cyano-phenyl]-4-cyano-2-methyl-benzamide; M.29.11.l) N-[5-[[2-bromo-6-chloro-[2,2,2-trifluoro-1-hydroxy-1-(trifluoromethypethyl]phenyl]carbamoyl]-2-cyano-phenyl]-4-cyano-2-methyl-benzamide; M.29.11.m) N-[5-[[2-bromo-6-chloro-4-[1,2,2,3,3,3-hexafluoro-1-(trifluoromethyl)propyl]phenyl]carbamoyl]-2-cyano-phenyl]-4-cyano-2-methyl-benzamide; M.29.11.n) 4-cyano-N-[2-cyano-5-[[2,6-dichloro-4-[1,2,2,3,3,3-hexafluoro-1-(trifluoromethyl)propyl]phenyl]carbamoyl]phenyl]-2-methyl-benzamide; M.29.11.O) 4-cyano-N-[2-cyano-5-[[2,6-di-chloro-4-[1,2,2,2-tetrafluoro-1-(trifluoromethypethyl]phenyl]carbamoyl]phenyl]-2-methyl-benzamide; M.29.11.p) N-[5-[[2-bromo-6-chloro-4-[1,2,2,2-tetrafluoro-1-(trifluoromethypethyl]phenyl]carbamoyl]-2-cyano-phenyl]-4-cyano-2-methyl-benzamide; or a compound selected from the group of M.29.12, wherein the compound is selected from M.29.12a) to M.29.12m): M.29.12.a) 2-(1,3-Dioxan-2-yl)-6-[2-(3-pyridinyl)-5-thiazolyl]-pyridine; M.29.12.b) 2-[6-[2-(5-Fluoro-3-pyridinyl)-5-thiazolyl]-2-pyridinyl]-pyrimidine; M.29.12.c) 2-[6-[2-(3-Pyridinyl)-5-thiazolyl]-2-pyridinyl]-pyrimidine; M.29.12.d) N-M ethylsulfonyl-6-[2-(3-pyridyl)thiazol-5-yl]pyridine-2-carboxamide; M.29.12.e) N-Methylsulfonyl-6-[2-(3-pyridyl)thiazol-5-yl]pyridine-2-carboxamide; M.29.12.f) N-Ethyl-N-[4-methyl-2-(3-pyridyl)thiazol-5-yl]-3-methylthio-propanamide; M.29.12.g) N-Methyl-N-[4-methyl-2-(3-pyridyl)thiazol-5-yl]-3-methylthio-propanamide;

M.29.12.h) N,2-Dimethyl-N-[4-methyl-2-(3-pyridyl)thiazol-5-yl]-3-methylthio-propanamide; M.29.12.i) N-Ethyl-2-methyl-N-[4-methyl-2-(3-pyridyl)thiazol-5-yl]-3-methylthio-propanamide; M.29.12.j) N-[4-Chloro-2-(3-pyridyl)thiazol-5-yl]-N-ethyl-2-methyl-3-methylthio-propanamide; M.29.12.k) N-[4-Chloro-2-(3-pyridyl)thiazol-5-yl]-N,2-dimethyl-3-methylthio-propanamide; M.29.12.l) N-[4-Chloro-2-(3-pyridyl)thiazol-5-yl]-N-methyl-3-methylthio-propanamide; M.29.12.m) N-[4-Chloro-2-(3-pyridyl)thiazol-5-yl]-N-ethyl-3-methylthio-propanamide; or the compounds M.29.14a) 1-[(6-Chloro-3-pyridinyl)methyl]-1,2,3,5,6,7-hexahydro-5-methoxy-7-methyl-8-nitro-imidazo[1,2-a]pyridine; or M.29.14b) 1-[(6-Chloropyridin-3-yl)methyl]-7-methyl-8-nitro-1,2,3,5,6,7-hexahydroimidazo[1,2-a]pyridin-5-ol; or the compounds M.29.16a) 1-isopropyl-N,5-dimethyl-N-pyridazin-4-yl-pyrazole-4-carboxamide; or M.29.16b) 1-(1,2-dimethylpropyl)-N-ethyl-5-methyl-N-pyridazin-4-yl-pyrazole-4-carboxamide; M.29.16c) N,5-dimethyl-N-pyridazin-4-yl-1-(2,2,2-trifluoro-1-methyl-ethyl)pyrazole-4-carboxamide; M.29.16d) 1-[1-(1-cyanocyclopropypethyl]-N-ethyl-5-methyl-N-pyridazin-4-yl-pyrazole-4-carboxamide; M.29.16e) N-ethyl-1-(2-fluoro-1-methyl-propyl)-5-methyl-N-pyridazin-4-yl-pyrazole-4-carboxamide; M.29.16f) 1-(1,2-dimethylpropyl)-N,5-dimethyl-N-pyridazin-4-yl-pyrazole-4-carboxamide; M.29.16g) 1-[1-(1-cyanocyclopropypethyl]-N,5-dimethyl-N-pyridazin-4-yl-pyrazole-4-carboxamide; M.29.16h) N-methyl-1-(2-fluoro-1-methyl-propyl]-5-methyl-N-pyridazin-4-yl-pyrazole-4-carboxamide; M.29.16i) 1-(4,4-difluorocyclohexyl)-N-ethyl-5-methyl-N-pyridazin-4-yl-pyrazole-4-carboxamide; or M.29.16j) 1-(4,4-difluorocyclohexyl)-N,5-dimethyl-N-pyridazin-4-yl-pyrazole-4-carboxamide, or M.29.17 a compound selected from the compounds M.29.17a) to M.29.17j): M.29.17a) N-(1-methylethyl)-2-(3-pyridinyl)-2H-indazole-4-carboxamide; M.29.17b) N-cyclopropyl-2-(3-pyridinyl)-2H-indazole-4-carboxamide; M.29.17c) N-cyclohexyl-2-(3-pyridinyl)-2H-indazole-4-carboxamide; M.29.17d) 2-(3-pyridinyl)-N-(2,2,2-trifluoroethyl)-2H-indazole-4-carboxamide; M.29.17e) 2-(3-pyridinyl)-N-[(tetrahydro-2-furanyl)methyl]-2H-indazole-5-carboxamide; M.29.17f) methyl 2-[[2-(3-pyridinyl)-2H-indazol-5-yl]carbonyl]hydrazinecarboxylate; M.29.17g) N-[(2,2-difluorocyclopropyl)methyl]-2-(3-pyridinyl)-2H-indazole-5-carboxamide; M.29.17h) N-(2,2-difluoropropyl)-2-(3-pyridinyl)-2H-indazole-5-carboxamide; M.29.17i) 2-(3-pyridinyl)-N-(2-pyrimidinylmethyl)-2H-indazole-5-carboxamide; M.29.17j) N-[(5-methyl-2-pyrazinyl)methyl]-2-(3-pyridinyl)-2H-indazole-5-carboxamide, or M.29.18 a compound selected from the compounds M.29.18a) to M.29.18d): M.29.18a) N-[3-chloro-1-(3-pyridyl)pyrazol-4-yl]-N-ethyl-3-(3,3,3-trifluoropropylsulfanyl)propanamide; M.29.18b) N-[3-chloro-1-(3-pyridyl)pyrazol-4-yl]-N-ethyl-3-(3,3,3-trifluoropropylsulfinyl)propanamide; M.29.18c) N-[3-chloro-1-(3-pyridyl)pyrazol-4-yl]-3-[(2,2-difluorocyclopropyl)methylsulfanyl]-N-ethyl-propanamide; M.29.18d) N-[3-chloro-1-(3-pyridyl)pyrazol-4-yl]-3-[(2,2-difluorocyclopropyl)methylsulfinyl]-N-ethyl-propanamide; or the compound M.29.19 sarolaner, or the compound M.29.20 lotilaner.

The commercially available compounds of the group M listed above may be found in The Pesticide Manual, 16th Edition, C. MacBean, British Crop Protection Council (2013) among other publications. The online Pesticide Manual is updated regularly and is accessible through http://bcpcdata.com/pesticide-manual.html.

Another online data base for pesticides providing the ISO common names is http://www.alanwood.net/pesticides.

The M.4 neonicotinoid cycloxaprid is known from WO2010/069266 and WO2011/069456, the neonicotinoid M.4A.2, sometimes also to be named as guadipyr, is known from WO2013/003977, and the neonicotinoid M.4A.3 (approved as paichongding in China) is known from WO2007/101369. The metaflumizone analogue M.226.1 is described in CN10171577 and the analogue M.226.2 in CN102126994. The phthalamides M.28.1 and M.28.2 are both known from WO2007/101540. The anthranilamide M.28.3 is described in WO2005/077934. The hydrazide compound M.28.4 is described in WO2007/043677. The anthranilamides M.28.5a) to M.28.5d) and M.28.5h) are described in WO 2007/006670, WO2013/024009 and WO2013/024010, the anthranilamide M.28.5i) is described in WO2011/085575, M.28.5j) in WO2008/134969, M.28.5k) in US2011/046186 and M.28.5l) in WO2012/034403. The diamide compound M.28.6 can be found in WO2012/034472. The spiroketal-substituted cyclic ketoenol derivative M.29.3 is known from WO2006/089633 and the biphenyl-substituted spirocyclic ketoenol derivative M.29.4 from WO2008/067911. The triazoylphenylsulfide M.29.5 is described in WO2006/043635, and biological control agents on the basis of *Bacillus firmus* are described in WO2009/124707. The compounds M.29.6a) to M.29.6i) listed under M.29.6 are described in WO2012/029672, and M.29.6j) and M.29.6k) in WO2013/129688. The nematicide M.29.8 is known from WO2013/055584. The isoxazoline M.29.9.a) is described in WO2013/050317. The isoxazoline M.29.9.b) is described in WO2014/126208. The pyridalyl-type analogue M.29.10 is known from WO2010/060379. The carboxamides broflanilide and M.29.11.b) to M.29.11.h) are described in WO2010/018714, and the carboxamides M.29.11i) to M.29.11.p) in WO2010/127926. The pyridylthiazoles M.29.12.a) to M.29.12.c) are known from WO2010/006713, M.29.12.d) and M.29.12.e) are known from WO2012/000896, and M.29.12.f) to M.29.12.m) from WO2010/129497. The compounds M.29.14a) and M.29.14b) are known from WO2007/101369. The pyrazoles M.29.16.a) to M.29.16h) are described in WO2010/034737, WO2012/084670, and WO2012/143317, respectively, and the pyrazoles M.29.16i) and M.29.16j) are described in U.S. 61/891,437. The pyridinylindazoles M.29.17a) to M.29.17.j) are described in WO2015/038503. The pyridylpyrazoles M.29.18a) to M.29.18d) are described in US2014/0213448. The isoxazoline M.29.19 is described in WO2014/036056. The isoxazoline M.29.20 is known from WO2014/090918.

The following list of fungicides, in conjunction with which the compounds of the present invention can be used, is intended to illustrate the possible combinations but does not limit them:

A) Respiration Inhibitors

Inhibitors of complex III at $Q_o$ site (e.g. strobilurins): azoxystrobin (A.1.1), coumethoxystrobin (A.1.2), coumoxystrobin (A.1.3), dimoxystrobin (A.1.4), enestroburin (A.1.5), fenaminstrobin (A.1.6), fenoxystrobin/flufenoxystrobin (A.1.7), fluoxastrobin (A.1.8), kresoxim-methyl (A.1.9), mandestrobin (A.1.10), metominostrobin (A.1.11), orysastrobin (A.1.12), picoxy.strobin (A.1.13), pyraclostrobin (A.1.14), pyrametostrobin (A.1.15), pyraoxystrobin (A.1.16), trifloxystrobin (A.1.17), 2-(2-(3-(2,6-dichlorophenyl)-1-methyl-allylideneaminooxymethyl)-phenyl)-2-methoxyimino-N-methyl-acetamide (A.1.18), pyribencarb (A.1.19), triclopyricarb/chlorodincarb (A.1.20), famoxadone (A.1.21), fenamidone (A.1.21), methyl-N-[2-[(1,4-dimethyl-5-phenyl-pyrazol-3-yl)oxylmethyl]phenyl]-N-methoxy-carbamate (A.1.22), 1-[3-chloro-2-[[1-(4-chlorophenyl)-1H-pyrazol-3-yl]oxymethyl]phenyl]-4-methyl-tetrazol-5-one (A.1.23), 1-[3-bromo-2-[[1-(4-chlorophenyl)pyrazol-3-yl]oxymethyl]phenyl]-4-methyl-tetrazol-5-one (A.1.24), 1-[2-[[1-(4-chlorophenyl)pyrazol-3-yl]oxymethyl]-3-methyl-phenyl]-4-methyl-tetrazol-5-one (A.1.25), 1-[2-[[1-(4-chlorophenyl)pyrazol-3-yl]oxymethyl]-3-fluoro-phenyl]-4-methyl-tetrazol-5-one (A.1.26), 1-[2-[[1-(2,4-dichlorophenyl)pyrazol-3-yl]oxymethyl]-3-fluoro-phenyl]-4-methyl-tetrazol-5-one (A.1.27), 1-[2-[[4-(4-chlorophenyl)thiazol-2-yl]oxymethyl]-3-methyl-phenyl]-4-methyl-tetrazol-5-one (A.1.28), 1-[3-chloro-2-[[4-(p-tolyl)thiazol-2-yl]oxymethyl]phenyl]-4-methyl-tetrazol-5-one (A.1.29), 1-[3-cyclopropyl-2-[[2-methyl-4-(1-methylpyrazol-3-yl)phenoxy]methyl]phenyl]-4-methyl-tetrazol-5-one (A.1.30), 1-[3-(difluoromethoxy)-2-[[2-methyl-4-(1-methylpyrazol-3-yl)phenoxy]methyl]phenyl]-4-methyl-tetrazol-5-one (A.1.31), 1-methyl-4-[3-methyl-2-[[2-methyl-4-(1-methylpyrazol-3-yl)phenoxy]methyl]phenyl]tetrazol-5-one (A.1.32), 1-methyl-4-[3-methyl-2-[[1-[3-(trifluoromethyl)phenyl]-ethylideneamino]oxymethyl]phenyl]tetrazol-5-one (A.1.33), (Z,2E)-5-[1-(2,4-dichlorophenyl)pyrazol-3-yl]-oxy-2-methoxyimino-N,3-dimethyl-pent-3-enamide (A.1.34), (Z,2E)-5-[1-(4-chlorophenyl)pyrazol-3-yl]oxy-2-methoxyimino-N,3-dimethyl-pent-3-enamide (A.1.35), (Z,2E)-5-[1-(4-chloro-2-fluoro-phenyl)pyrazol-3-yl]oxy-2-methoxyimino-N,3-dimethyl-pent-3-enamide (A.1.36), inhibitors of complex III at Q, site: cyazofamid (A.2.1), amisulbrom (A.2.2), [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate (A.2.3), [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate (A.2.4), [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl]2-methylpropanoate (A.2.5), [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl]2-methylpropanoate (A.2.6); (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl2-methylpropanoate (A.2.7), (3S,6S,7R,8R)-8-benzyl-3-[3-[(isobutyryloxy)methoxy]-4-methoxypicolinamido]-6-methyl-4,9-dioxo-1,5-dioxonan-7-ylisobutyrate (A.2.8);

inhibitors of complex II (e.g. carboxamides): benodanil (A.3.1), benzovindiflupyr (A.3.2), bixafen (A.3.3), boscalid (A.3.4), carboxin (A.3.5), fenfuram (A.3.6), fluopyram (A.3.7), flutolanil (A.3.8), fluxapyroxad (A.3.9), furametpyr (A.3.10), isofetamid (A.3.11), isopyrazam (A.3.12), mepronil (A.3.13), oxycarboxin (A.3.14), penflufen (A.3.14), penthiopyrad (A.3.15), sedaxane (A.3.16), tecloftalam (A.3.17), thifluzamide (A.3.18), N-(4'-trifluoromethylthiobiphenyl-2-yl)-3-difluoromethyl-1-methyl-1H-pyrazole-4-carboxamide (A.3.19), N-(2-(1,3,3-trimethyl-butyl)-phenyl)-1,3-dimethyl-5-fluoro-1H-pyrazole-4-carboxamide (A.3.20), 3-(difluoromethyl)-1-methyl-N-(1,1,3-trimethylindan- 4-yl)pyrazole-4-carboxamide (A.3.21), 3-(trifluoromethyl)-1-methyl-N-(1,1,3-trimethyl-indan-4-yl)pyrazole-4-carboxamide (A.3.22), 1,3-dimethyl-N-(1,1,3-trimethylindan-4-yl)pyrazole-4-carboxamide (A.3.23), 3-(trifluoromethyl)-1,5-dimethyl-N-(1,1,3-trimethylindan-4-yl)pyrazole-4-carboxamide (A.3.24), 1,3,5-trimethyl-N-(1,1,3-trimethylindan-4-yl)pyrazole-4-carboxamide (A.3.25), N-(7-fluoro-1,1,3-trimethyl-indan-4-yl)-1,3-dimethyl-pyrazole-4-carboxamide (A.3.26), N-[2-(2,4-dichlorophenyl)-2-methoxy-1-methyl-ethyl]-3-(difluoromethyl)-1-methyl-pyrazole-4-carboxamide (A.3.27);

other respiration inhibitors (e.g. complex I, uncouplers): diflumetorim (A.4.1), (5,8-difluoro-quinazolin-4-yl)-{2-[2-fluoro-4-(4-trifluoromethylpyridin-2-yloxy)-phenyl]-ethyl}-amine (A.4.2); nitrophenyl derivates: binapacryl (A.4.3), dinobuton (A.4.4), dinocap (A.4.5), fluazinam (A.4.6); ferimzone (A.4.7); organometal compounds: fentin salts, such as fentin-acetate (A.4.8), fentin chloride (A.4.9) or fentin hydroxide (A.4.10); ametoctradin (A.4.11); and silthiofam (A.4.12);

B) Sterol Biosynthesis Inhibitors (SBI Fungicides)

C14 demethylase inhibitors (DMI fungicides): triazoles: azaconazole (B.1.1), bitertanol (B.1.2), bromuconazole (B.1.3), cyproconazole (B.1.4), difenoconazole (B.1.5), diniconazole (B.1.6), diniconazole-M (B.1.7), epoxiconazole (B.1.8), fenbuconazole (B.1.9), fluquinconazole (B.1.10), flusilazole (B.1.11), flutriafol (B.1.12), hexaconazole (B.1.13), imibenconazole (B.1.14), ipconazole (B.1.15), metconazole (B.1.17), myclobutanil (B.1.18), oxpoconazole (B.1.19), paclo-butrazole (B.1.20), penconazole (B.1.21), propiconazole (B.1.22), prothioconazole (B.1.23), simeconazole (B.1.24), tebuconazole (B.1.25), tetraconazole (B.1.26), triadimefon (B.1.27), triadimenol (B.1.28), triticonazole (B.1.29), uniconazole (B.1.30), [rel-(2S;3R)-3-(2-chlorophenyl)-2-(2,4-difluorophenyl)-oxiranylmethyl]-5-thiocyanato-1H-[1,2,4]triazolo (B.1.31), 2-[re/-(2S;3k)-3-(2-chlorophenyl)-2-(2,4-difluorophenyl)-oxiranylmethyl]-2H-[1,2,4]triazole-3-thiol (B.1.32), 2-[2-chloro-4-(4-chlorophenoxy)phenyl]-1-(1,2,4-triazol-1-yl)pentan-2-ol (B.1.33), 1-[4-(4-chlorophenoxy)-2-(trifluoromethyl)phenyl]-1-cyclopropyl-2-(1,2,4-triazol-1-yl)ethanol (B.1.34), 2-[4-(4-chlorophenoxy)-2-(trifluoromethyl)phenyl]-1-(1,2,4-triazol-1-yl)butan-2-ol (B.1.35), 2-[2-chloro-4-(4-chlorophen-oxy)phenyl]-1-(1,2,4-triazol-1-yl)butan-2-ol (B.1.36), 4-[4-(4-chlorophenoxy)-2-(trifluoromethyl)phenyl]-3-methyl-1-(1,2,4-triazol-1-yl)butan-2-ol (B.1.37), 4-[4-(4-chlorophenoxy)-2-(trifluoromethyl)-phenyl]-1-(1,2,4-triazol-1-yl)propan-2-ol (B.1.38), 2-[2-chloro-4-(4-chlorophenoxy)phenyl]-3-methyl-1-(1,2,4-triazol-1-yl)butan-2-ol (B.1.39), 4-[4-(4-chlorophenoxy)-2-(trifluoromethyl)phenyl]-1-(1,2,4-triazol-1-yl)pentan-2-ol (B.1.40), 4-[4-(4-fluorophenoxy)-2-(trifluoromethyl)phenyl]-1-(1,2,4-triazol-1-yl)propan-2-ol (B.1.41), 2-[2-chloro-4-(4-chlorophenoxy)phenyl]-1-(1,2,4-triazol-1-yl)pent-3-yn-2-ol (B.1.51); imidazoles: imazalil (B.1.42), pefurazoate (B.1.43), prochloraz (B.1.44), triflumizol (B.1.45); pyrimidines, pyridines and piperazines: fenarimol (B.1.46), nuarimol (B.1.47), pyrifenox (B.1.48), triforine (B.1.49), [3-(4-chloro-2-fluoro-phenyl)-5-(2,4-difluorophenypisoxazol-4-yl]-(3-pyridyl)methanol (B.1.50);

Delta14-reductase inhibitors: aldimorph (B.2.1), dodemorph (B.2.2), dodemorph-acetate (B.2.3), fenpropimorph (B.2.4), tridemorph (B.2.5), fenpropidin (B.2.6), piperalin (B.2.7), spiroxamine (B.2.8);

Inhibitors of 3-keto reductase: fenhexamid (B.3.1);

C) Nucleic Acid Synthesis Inhibitors phenylamides or acyl amino acid fungicides: benalaxyl (C.1.1), benalaxyl-M (C.1.2), kiralaxyl (C.1.3), metalaxyl (C.1.4), metalaxyl-M (mefenoxam, C.1.5), ofurace (C.1.6), oxadixyl (C.1.7);

others: hymexazole (C.2.1), octhilinone (C.2.2), oxolinic acid (C.2.3), bupirimate (C.2.4), 5-fluorocytosine (C.2.5), 5-fluoro-2-(p-tolylmethoxy)pyrimidin-4-amine (C.2.6), 5-fluoro-2-(4-fluoro-phenylmethoxy)pyrimidin-4-amine (C.2.7);

D) Inhibitors of Cell Division and Cytoskeleton tubulin inhibitors, such as benzimidazoles, thiophanates: benomyl (D1.1), carbendazim (D1.2), fuberidazole (D1.3), thiabendazole (D1.4), thiophanate-methyl (D1.5); triazolopyrimidines: 5-chloro-7-(4-methylpiperidin-1-yl)-6-(2,4,6-trifluorophenyl)-[1,2,4]triazolo[1,5-a]pyrimidine (D1.6);

other cell division inhibitors: diethofencarb (D2.1), ethaboxam (D2.2), pencycuron (D2.3), fluopicolide (D2.4), zoxamide (D2.5), metrafenone (D2.6), pyriofenone (D2.7);

E) Inhibitors of Amino Acid and Protein Synthesis methionine synthesis inhibitors (anilino-pyrimidines): cyprodinil (E.1.1), mepanipyrim (E.1.2), pyrimethanil (E.1.3);

protein synthesis inhibitors: blasticidin-S (E.2.1), kasugamycin (E.2.2), kasugamycin hydrochloride-hydrate (E.2.3), mildiomycin (E.2.4), streptomycin (E.2.5), oxytetracyclin (E.2.6), polyoxine (E.2.7), validamycin A (E.2.8);

F) Signal Transduction Inhibitors

MAP/histidine kinase inhibitors: fluoroimid (F.1.1), iprodione (F.1.2), procymidone (F.1.3), vinclozolin (F.1.4), fenpiclonil (F.1.5), fludioxonil (F.1.6);

G protein inhibitors: quinoxyfen (F.2.1);

G) Lipid and Membrane Synthesis Inhibitors

Phospholipid biosynthesis inhibitors: edifenphos (G.1.1), iprobenfos (G.1.2), pyrazophos (G.1.3), isoprothiolane (G.1.4);

lipid peroxidation: dicloran (G.2.1), quintozene (G.2.2), tecnazene (G.2.3), tolclofos-methyl (G.2.4), biphenyl (G.2.5), chloroneb (G.2.6), etridiazole (G.2.7);

phospholipid biosynthesis and cell wall deposition: dimethomorph (G.3.1), flumorph (G.3.2), mandipropamid (G.3.3), pyrimorph (G.3.4), benthiavalicarb (G.3.5), iprovalicarb (G.3.6), valifenalate (G.3.7) and N-(1-(1-(4-cyano-phenypethanesulfonyl)-but-2-yl) carbamic acid-(4-fluorophenyl) ester (G.3.8);

compounds affecting cell membrane permeability and fatty acides: propamocarb (G.4.1);

fatty acid amide hydrolase inhibitors: oxathiapiprolin (G.5.1), 2-{3-[2-(1-{[3,5-bis(difluoro-methyl-1H-pyrazol-1-yl]acetyllpiperidin-4-yl)-1,3-thiazol-4-yl]-4,5-dihydro-1,2-oxazol-5-yl}phenyl methanesulfonate (G.5.2), 2-{3-[2-(1-{[3,5-bis(difluoromethyl)-1H-pyrazol-1-yl]acetyllpiperidin-4-yl) 1,3-thiazol-4-yl]-4,5-dihydro-1,2-oxazol-5-yl}-3-chlorophenyl methanesulfonate (G.5.3);

H) Inhibitors with Multi Site Action inorganic active substances: Bordeaux mixture (H.1.1), copper acetate (H.1.2), copper hydroxide (H.1.3), copper oxychloride (H.1.4), basic copper sulfate (H.1.5), sulfur (H.1.6);

thio- and dithiocarbamates: ferbam (H.2.1), mancozeb (H.2.2), maneb (H.2.3), metam (H.2.4), metiram (H.2.5), propineb (H.2.6), thiram (H.2.7), zineb (H.2.8), ziram (H.2.9);

organochlorine compounds (e. g. phthalimides, sulfamides, chloronitriles): anilazine (H.3.1), chlorothalonil (H.3.2), captafol (H.3.3), captan (H.3.4), folpet (H.3.5), dichlofluanid (H.3.6), dichlorophen (H.3.7), hexachlorobenzene (H.3.8), pentachlorphenole (H.3.9) and its salts, phthalide (H.3.10), tolylfluanid (H.3.11), N-(4-chloro-2-nitro-phenyl)-N-ethyl-4-methyl-benzenesulfonamide (H.3.12);

guanidines and others: guanidine (H.4.1), dodine (H.4.2), dodine free base (H.4.3), guazatine (H.4.4), guazatine-acetate (H.4.5), iminoctadine (H.4.6), iminoctadine-triacetate (H.4.7), iminoctadine-tris(albesilate) (H.4.8), dithianon (H.4.9), 2,6-dimethyl-1H,5H-[1,4]dithiino[2,3-c:5,6-c']dipyrrole-1,3,5,7(2H,6H)-tetraone (H.4.10);

I) Cell Wall Synthesis Inhibitors inhibitors of glucan synthesis: validamycin (I.1.1), polyoxin B (I.1.2);

melanin synthesis inhibitors: pyroquilon (I.2.1), tricyclazole (I.2.2), carpropamid (1.2.3), dicyclomet (I.2.4), fenoxanil (I.2.5);

J) Plant Defence Inducers acibenzolar-S-methyl (J.1.1), probenazole (J.1.2), isotianil (J.1.3), tiadinil (J.1.4), prohexadione-calcium (J.1.5); phosphonates: fosetyl (J.1.6), fosetyl-aluminum (J.1.7), phosphorous acid and its salts (J.1.8), potassium or sodium bicarbonate (J.1.9);

K) Unknown Mode of Action bronopol (K.1.1), chinomethionat (K.1.2), cyflufenamid (K.1.3), cymoxanil (K.1.4), dazomet (K.1.5), debacarb (K.1.6), diclomezine (K.1.7), difenzoquat (K.1.8), difenzoquat-methylsulfate (K.1.9), diphenylamin (K.1.10), fenpyrazamine (K.1.11), flumetover (K.1.12), flusulfamide (K.1.13), flutianil (K.1.14), methasulfocarb (K.1.15), nitrapyrin (K.1.16), nitrothal-isopropyl (K.1.18), oxathiapiprolin (K.1.19), tolprocarb (K.1.20), oxin-copper (K.1.21), proquinazid (K.1.22), tebufloquin (K.1.23), tecloftalam (K.1.24), triazoxide (K.1.25), 2-butoxy-6-iodo-3-propylchromen-4-one (K.1.26), 2-[3,5-bis(difluoromethyl)-1H-pyrazol-1-yl]-1-[4-(4-{5-[2-(prop-2-yn-1-yl oxy)phenyl]-4,5-dihydro-1,2-oxazol-3-yl1-1,3-thiazol-2-yl)piperidin-1-yl]ethanone (K.1.27), 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone (K.1.28), 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl1-1,3-thiazol-2-yl)piperidin-1-yl]ethanone (K.1.29), N-(cyclopropylmethoxyimino-(6-difluoromethoxy-2,3-difluoro-phenyl)-methyl)-2-phenyl acetamide (K.1.30), N'-(4-(4-chloro-3-trifluoromethyl-phenoxy)-2,5-dimethyl-phenyl)-N-ethyl-N-methyl formamidine (K.1.31), N'-(4-(4-fluoro-3-trifluoromethyl-phenoxy)-2,5-dimethyl-phenyl)-N-ethyl-N-methyl formamidine (K.1.32), N'-(2-methyl-5-trifluoromethyl-4-(3-trimethylsilanyl-propoxy)-phenyl)-N-ethyl-N-methyl formamidine (K.1.33), N'-(5-difluoromethyl-2-methyl-4-(3-trimethylsilanyl-propoxy)-phenyl)-N-ethyl-N-methyl formamidine (K.1.34), methoxy-acetic acid 6-tert-butyl-8-fluoro-2,3-dimethyl-quinolin-4-yl ester (K.1.35), 3-[5-(4-methylphenyl)-2,3-dimethyl-isoxazolidin-3-yl]-pyridine (K.1.36), 3-[5-(4-chloro-phenyl)-2,3-dimethyl-isoxazolidin-3-yl]-pyridine (pyrisoxazole) (K.1.37), N-(6-methoxy-pyridin-3-yl) cyclopropanecarboxylic acid amide (K.1.38), 5-chloro-1-(4,6-dimethoxy-pyrimidin-2-yl)-2-methyl-1H-benzoimidazole (K.1.39), 2-(4-chloro-phenyl)-N-[4-(3,4-dimethoxy-phenyl)-isoxazol-5-yl]-2-prop-2-ynyloxy-acetamide, ethyl (Z)-3-amino-2-cyano-3-phenyl-prop-2-enoate (K.1.40), picarbutrazox (K.1.41), pentyl N46-[[(Z)-[(1-methyl-tetrazol-5-yl)-phenyl-methylene]amino]oxymethyl]-2-pyridyl]carbamate (K.1.42), 2-[2-[(7,8-difluoro-2-methyl-3-quinolyl)oxy]-6-fluoro-phenyl]propan-2-ol (K.1.43), 2-[2-fluoro-6-[(8-fluoro-2-methyl-3-quinolypoxy]phen-yl]propan-2-ol (K.1.44), 3-(5-fluoro-3,3,4,4-tetramethyl-3,4-dihydroisoquinolin-1-yl)quinoline (K.1.45), 3-(4,4-difluoro-3,3-dimethyl-3,4-dihydroisoquinolin-1-yl)quinoline (K.1.46), 3-(4,4,5-trifluoro-3,3-dimethyl-3,4-dihydroisoquinolin-1-yl) quinoline (K.1.47), 9-fluoro-2,2-dimethyl-5-(3-quinolyl)-3H-1,4-benzoxa-zepine (K.1.48).

The fungicides described by common names, their preparation and their activity e.g. against harmful fungi is known (cf.: http://www.alanwood.net/pesticides/); these substances are commercially available.

The fungicides described by IUPAC nomenclature, their preparation and their pesticidal activity is also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. Nos. 3,296,272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657, WO2012/168188, WO 2007/006670, WO 2011/77514; WO13/047749, WO 10/069882, WO 13/047441, WO 03/16303, WO 09/90181, WO 13/007767, WO 13/010862, WO 13/127704, WO 13/024009, WO 13/024010 and WO 13/047441, WO 13/162072, WO 13/092224, WO 11/135833).

The invention also relates to agrochemical compositions comprising an auxiliary and at least one compound of the present invention or a mixture thereof.

An agrochemical composition comprises a pesticidally effective amount of a compound of the present invention or a mixture thereof. The term "pesticidally effective amount" is defined below.

The compounds of the present invention or the mixtures thereof can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Mono-graph No. 2, 6th Ed. May 2008, CropLife International.

The compositions are prepared in a known manner, such as described by Mollet and Grube-mann, Formulation technology, Wiley VCH, Weinheim, 2001; or Knowles, New developments in crop protection product formulation, Agrow Reports DS243, T&F Informa, London, 2005. Examples for suitable auxiliaries are solvents, liquid carriers, solid carriers or fillers, surfactants, dispersants, emulsifiers, wetters, adjuvants, solubilizers, penetration enhancers, protec-tive colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclo¬hexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sul-fates, phosphates, carboxylates, and mixtures thereof. Examples of sulfonates are alkylaryl-sulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkyl naphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Exam-pies of carboxylates are alkyl carboxylates, and carboxylated alcohol or alkylphenol ethoxylates.

Suitable nonionic surfactants are alkoxylates, N-subsituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Exam-pies of N-substitued fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are homo- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compounds of the present invention on the target. Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanofer-rate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:
i) Water-Soluble Concentrates (SL, LS)
10-60 wt % of a compound I according to the invention and 5-15 wt % wetting agent (e.g. alcohol alkoxylates) are dissolved in water and/or in a water-soluble solvent (e.g. alcohols) up to 100 wt %. The active substance dissolves upon dilution with water.

ii) Dispersible Concentrates (DC)
5-25 wt % of a compound I according to the invention and 1-10 wt % dispersant (e. g. polyvinylpyrrolidone) are dissolved in up to 100 wt % organic solvent (e.g. cyclohexanone). Dilution with water gives a dispersion.

iii) Emulsifiable Concentrates (EC)
15-70 wt % of a compound I according to the invention and 5-10 wt % emulsifiers (e.g. calcium dodecylbenzenesulfonate and castor oil ethoxylate) are dissolved in up to 100 wt % water-insoluble organic solvent (e.g. aromatic hydrocarbon). Dilution with water gives an emulsion.

iv) Emulsions (EW, EO, ES)
5-40 wt % of a compound I according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into up to 100 wt % water by means of an emulsifying machine and made into a homogeneous emulsion. Dilution with water gives an emulsion.

v) Suspensions (SC, OD, FS)

In an agitated ball mill, 20-60 wt % of a compound I according to the invention are comminuted with addition of 2-10 wt % dispersants and wetting agents (e.g. sodium lignosulfonate and alcohol ethoxylate), 0,1-2 wt % thickener (e.g. xanthan gum) and up to 100 wt % water to give a fine active substance suspension. Dilution with water gives a stable suspension of the active sub-stance. For FS type composition up to 40 wt % binder (e.g. polyvinylalcohol) is added.

vi) Water-Dispersible Granules and Water-Soluble Granules (WG, SG)

50-80 wt % of a compound I according to the invention are ground finely with addition of up to 100 wt % dispersants and wetting agents (e.g. sodium lignosulfonate and alcohol ethoxylate) and prepared as water-dispersible or water-soluble granules by means of technical appliances (e.g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound I according to the invention are ground in a rotor-stator mill with addition of 1-5 wt % dispersants (e.g. sodium lignosulfonate), 1-3 wt % wetting agents (e.g. alcohol ethoxylate) and up to 100 wt % solid carrier, e.g. silica gel. Dilution with water gives a stable dispersion or solution of the active substance.

viii) Gel (GW, GF)

In an agitated ball mill, 5-25 wt % of a compound I according to the invention are comminuted with addition of 3-10 wt % dispersants (e.g. sodium lignosulfonate), 1-5 wt % thickener (e.g. carboxymethylcellulose) and up to 100 wt % water to give a fine suspension of the active sub-stance. Dilution with water gives a stable suspension of the active substance.

ix) Microemulsion (ME)

5-20 wt % of a compound I according to the invention are added to 5-30 wt % organic solvent blend (e.g. fatty acid dimethylamide and cyclohexanone), 10-25 wt % surfactant blend (e.g. alkohol ethoxylate and arylphenol ethoxylate), and water up to 100%. This mixture is stirred for 1 h to produce spontaneously a thermodynamically stable microemulsion.

x) Microcapsules (CS)

An oil phase comprising 5-50 wt % of a compound I according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insolu-ble organic solvent (e.g. aromatic hydrocarbon), and an isocyanate monomer (e.g. diphenylme-thene-4,4'-diisocyanatae) are dispersed into an aqueous solution of a protective colloid (e.g. polyvinyl alcohol).

The addition of a polyamine (e.g. hexamethylenediamine) results in the formation of a polyurea microcapsule. The monomers amount to 1-10 wt %. The wt % relate to the total CS composition.

xi) Dustable Powders (DP, DS)

1-10 wt % of a compound I according to the invention are ground finely and mixed intimately with up to 100 wt % solid carrier, e.g. finely divided kaolin.

xii) Granules (GR, FG)

0.5-30 wt % of a compound I according to the invention is ground finely and associated with up to 100 wt % solid carrier (e.g. silicate). Granulation is achieved by extrusion, spray-drying or the fluidized bed.

xiii) Ultra-Low Volume Liquids (UL)

1-50 wt % of a compound I according to the invention are dissolved in up to 100 wt % organic solvent, e.g. aromatic hydrocarbon.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably be-tween 0.1 and 90%, and most preferably between 0.5 and 75%, by weight of active sub-stance. The active substances are employed in a purity of from 90% to 100%, preferably from 95% to 100% (according to NMR spectrum).

Various types of oils, wetters, adjuvants, fertilizer, or micronutrients, and other pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage de-vice, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e.g. components comprising compounds of the present invention and/or mixing partners as defined above, may be mixed by the user in a spray tank and further auxiliaries and additives may be added, if appropriate.

In a further embodiment, either individual components of the composition according to the invention or partially premixed components, e.g. components comprising compounds of the present invention and/or mixing partners as defined above, can be applied jointly (e.g. after tank mix) or consecutively.

The compounds of the present invention are suitable for use in protecting crops, plants, plant propagation materials, such as seeds, or soil or water, in which the plants are growing, from attack or infestation by animal pests. Therefore, the present invention also relates to a plant protection method, which comprises contacting crops, plants, plant propagation materials, such as seeds, or soil or water, in which the plants are growing, to be protected from attack or infestation by animal pests, with a pesticidally effective amount of a compound of the present invention.

The compounds of the present invention are also suitable for use in combating or controlling animal pests. Therefore, the present invention also relates to a method of combating or controlling animal pests, which comprises contacting the animal pests, their habitat, breeding ground, or food supply, or the crops, plants, plant propagation materials, such as seeds, or soil, or the area, material or environment in which the animal pests are growing or may grow, with a pesticidally effective amount of a compound of the present invention.

The compounds of the present invention are effective through both contact and ingestion. Furthermore, the compounds of the present invention can be applied to any and all developmental stages, such as egg, larva, pupa, and adult.

The compounds of the present invention can be applied as such or in form of compositions comprising them as defined above. Furthermore, the compounds of the present invention can be applied together with a mixing partner as defined above or in form of compositions comprising said mixtures as defined above. The components of said mixture can be applied simultaneously, jointly or separately, or in succession, that is immediately one after another and thereby creating the mixture "in situ" on the desired location, e.g. the plant, the sequence, in the case of separate application, generally not having any effect on the result of the control measures.

The application can be carried out both before and after the infestation of the crops, plants, plant propagation materials, such as seeds, soil, or the area, material or environment by the pests.

Suitable application methods include inter alia soil treatment, seed treatment, in furrow application, and foliar application. Soil treatment methods include drenching the soil, drip irrigation (drip application onto the soil), dipping roots, tubers or bulbs, or soil injection. Seed treatment techniques include seed dressing, seed coating, seed dusting, seed soaking, and seed pelleting. In furrow applications typically include the steps of making a furrow in cultivated land, seeding the furrow with seeds, applying the pesticidally active compound to the furrow, and closing the furrow. Foliar application refers to the application of the pesticidally active compound to plant foliage, e.g. through spray equipment. For foliar applications, it can be advantageous to modify the behavior of the pests by use of pheromones in combination with the compounds of the present invention. Suitable pheromones for specific crops and pests are known to a skilled person and publicly available from databases of pheromones and semiochemicals, such as http://www.pherobase.com.

As used herein, the term "contacting" includes both direct contact (applying the compounds/compositions directly on the animal pest or plant—typically to the foliage, stem or roots of the plant) and indirect contact (applying the compounds/compositions to the locus, i.e. habitat, breeding ground, plant, seed, soil, area, material or environment in which a pest is growing or may grow, of the animal pest or plant).

The term "animal pest" includes arthropods, gastropods, and nematodes. Preferred animal pests according to the invention are arthropods, preferably insects and arachnids, in particular insects. Insects, which are of particular relevance for crops, are typically referred to as crop insect pests.

The term "crop" refers to both, growing and harvested crops.

The term "plant" includes cereals, e.g. durum and other wheat, rye, barley, triticale, oats, rice, or maize (fodder maize and sugar maize/sweet and field corn); beet, e.g. sugar beet or fodder beet; fruits, such as pomes, stone fruits or soft fruits, e.g. apples, pears, plums, peaches, nectarines, almonds, cherries, papayas, strawberries, raspberries, blackberries or gooseberries; leguminous plants, such as beans, lentils, peas, alfalfa or soybeans; oil plants, such as rapeseed (oilseed rape), turnip rape, mustard, olives, sunflowers, coconut, cocoa beans, castor oil plants, oil palms, ground nuts or soybeans; cucurbits, such as squashes, pumpkins, cucumber or melons; fiber plants, such as cotton, flax, hemp or jute; citrus fruit, such as oranges, lemons, grapefruits or mandarins; vegetables, such as eggplant, spinach, lettuce (e.g. iceberg lettuce), chicory, cabbage, asparagus, cabbages, carrots, onions, garlic, leeks, tomatoes, potatoes, cucurbits or sweet peppers; lauraceous plants, such as avocados, cinnamon or camphor; energy and raw material plants, such as corn, soybean, rapeseed, sugar cane or oil palm; tobacco; nuts, e.g. walnuts; pistachios; coffee; tea; bananas; vines (table grapes and grape juice grape vines); hop; sweet leaf (also called Stevia); natural rubber plants or ornamental and forestry plants, such as flowers (e.g. carnation, petunias, geranium/pelargoniums, pansies and impatiens), shrubs, broad-leaved trees (e.g. poplar) or evergreens, e.g. conifers; eucalyptus; turf; lawn; grass such as grass for animal feed or ornamental uses. Preferred plants include potatoes sugar beets, tobacco, wheat, rye, barley, oats, rice, corn, cotton, soybeans, rapeseed, legumes, sunflowers, coffee or sugar cane; fruits; vines; ornamentals; or vegetables, such as cucumbers, tomatoes, beans or squashes.

The term "plant" is to be understood as including wild type plants and plants, which have been modified by either conventional breeding, or mutagenesis or genetic engineering, or by a combination thereof.

Plants, which have been modified by mutagenesis or genetic engineering, and are of particular commercial importance, include alfalfa, rapeseed (e.g. oilseed rape), bean, carnation, chicory, cotton, eggplant, eucalyptus, flax, lentil, maize, melon, papaya, petunia, plum, poplar, potato, rice, soybean, squash, sugar beet, sugarcane, sunflower, sweet pepper, tobacco, tomato, and cereals (e.g. wheat), in particular maize, soybean, cotton, wheat, and rice. In plants, which have been modified by mutagenesis or genetic engineering, one or more genes have been mutagenized or integrated into the genetic material of the plant. The one or more mutagenized or integrated genes are preferably selected from pat, epsps, cry1Ab, bar, cry1Fa2, cry1Ac, cry34Ab1, cry35AB1, cry3A, cryF, cry1F, mcry3a, cry2Ab2, cry3Bb1, cry1A.105, dfr, barnase, vip3Aa20, barstar, als, bxn, bp40, asn1, and ppo5. The mutagenesis or integration of the one or more genes is performed in order to improve certain properties of the plant. Such properties, also known as traits, include abiotic stress tolerance, altered growth/yield, disease resistance, herbicide tolerance, insect resistance, modified product quality, and pollination control. Of these properties, herbicide tolerance, e.g. imidazolinone tolerance, glyphosate tolerance, or glufosinate tolerance, is of particular importance. Several plants have been rendered tolerant to herbicides by mutagenesis, for example Clearfield® oilseed rape being tolerant to imidazolinones, e.g. imazamox. Alternatively, genetic engineering methods have been used to render plants, such as soybean, cotton, corn, beets and oil seed rape, tolerant to herbicides, such as glyphosate and glufosinate, some of which are commercially available under the trade names RoundupReady® (glyphosate) and LibertyLink® (glufosinate). Furthermore, insect resistance is of importance, in particular lepidopteran insect resistance and coleopteran insect resistance. Insect resistance is typically achieved by modifying plants by integrating cry and/or vip genes, which were isolated from *Bacillus thuringiensis* (Bt), and code for the respective Bt toxins. Genetically modified plants with insect resistance are commercially available under trade names including Wide-Strike®, Bollgard®, Agrisure®, Herculex®, YieldGard®, Genuity®, and Intacta®. Plants may be modified by mutagenesis or genetic engineering either in terms of one property (singular traits) or in terms of a combination of properties (stacked traits). Stacked traits, e.g. the combination of herbicide tolerance and insect resistance, are of increasing importance. In general, all relevant modified plants in connection with singular or stacked traits as well as detailed information as to the mutagenized or integrated genes and the respective events are available from websites of the organizations "International Service for the Acquisition of Agri-biotech Applications (ISAAA)" (http://www.isaaa.org/gmapprovaldatabase) and "Center for Environmental Risk Assessment (CERA)" (http://cera-gmc.org/GMCropDatabase).

It has surprisingly been found that the pesticidal activity of the compounds of the present invention may be enhanced by the insecticidal trait of a modified plant. Furthermore, it has been found that the compounds of the present invention are suitable for preventing insects to become resistant to the insecticidal trait or for combating pests, which already have become resistant to the insecticidal trait of a modified plant. Moreover, the compounds of the present invention are suitable for combating pests, against which the insecticidal trait is not effective, so that a complementary insecticidal activity can advantageously be used.

The term "plant propagation material" refers to all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "seed" embraces seeds and plant propagules of all kinds including but not limited to true seeds, seed pieces, suckers, corms, bulbs, fruit, tubers, grains, cuttings, cut shoots and the like, and means in a preferred embodiment true seeds. In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment, in furrow application or of application to the pests dwelling place or nest, the quantity of active ingredient ranges from 0.0001 to 500 g per 100 m$^2$, preferably from 0.001 to 20 g per 100 m$^2$.

For use in treating crop plants, e.g. by foliar application, the rate of application of the active ingredients of this invention may be in the range of 0.0001 g to 4000 g per hectare, e.g. from 1 g to 2 kg per hectare or from 1 g to 750 g per hectare, desirably from 1 g to 100 g per hectare, more desirably from 10 g to 50 g per hectare, e.g., 10 to 20 g per hectare, 20 to 30 g per hectare, 30 to 40 g per hectare, or 40 to 50 g per hectare.

The compounds of the present invention are particularly suitable for use in the treatment of seeds in order to protect the seeds from insect pests, in particular from soil-living insect pests, and the resulting seedling's roots and shoots against soil pests and foliar insects. The present invention therefore also relates to a method for the protection of seeds from insects, in particular from soil insects, and of the seedling's roots and shoots from insects, in particular from soil and foliar insects, said method comprising treating the seeds before sowing and/or after pregermination with a compound of the present invention. The protection of the seedling's roots and shoots is preferred. More preferred is the protection of seedling's shoots from piercing and sucking insects, chewing insects and nematodes.

The term "seed treatment" comprises all suitable seed treatment techniques known in the art, such as seed dressing, seed coating, seed dusting, seed soaking, seed pelleting, and in-furrow application methods. Preferably, the seed treatment application of the active compound is carried out by spraying or by dusting the seeds before sowing of the plants and before emergence of the plants.

The present invention also comprises seeds coated with or containing the active compound. The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is for example seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkinisquash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment of seeds from plants, which have been modified by mutagenisis or genetic engineering, and which e.g. tolerate the action of herbicides or fungicides or insecticides. Such modified plants have been described in detail above.

Conventional seed treatment formulations include for example flowable concentrates FS, solutions LS, suspoemulsions (SE), powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter. Preferably, the formulations are applied such that germination is not included.

The active substance concentrations in ready-to-use formulations, which may be obtained after two-to-tenfold dilution, are preferably from 0.01 to 60% by weight, more preferably from 0.1 to 40% by weight.

In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of the compounds of the present invention for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

In the treatment of seed, the application rates of the compounds of the invention are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed, e.g. from 1 g to 100 g or from 5 g to 100 g per 100 kg of seed.

The invention therefore also relates to seed comprising a compound of the present invention, or an agriculturally useful salt thereof, as defined herein. The amount of the compound of the present invention or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

The compounds of the present invention may also be used for improving the health of a plant. Therefore, the present invention also relates to a method for improving plant health by treating a plant, plant propagation material and/or the locus where the plant is growing or is to grow with an effective and non-phytotoxic amount of a compound of the present invention.

As used herein "an effective and non-phytotoxic amount" means that the compound is used in a quantity which allows to obtain the desired effect but which does not give rise to any phytotoxic symptom on the treated plant or on the plant grown from the treated propagule or treated soil.

The terms "plant" and "plant propagation material" are defined above.

"Plant health" is defined as a condition of the plant and/or its products which is determined by several aspects alone or in combination with each other such as yield (for example increased biomass and/or increased content of valuable ingredients), quality (for example improved content or composition of certain ingredients or shelf life), plant vigour (for example improved plant growth and/or greener leaves ("greening effect"), tolerance to abiotic (for example drought) and/or biotic stress (for example disease) and production efficiency (for example, harvesting efficiency, processability).

The above identified indicators for the health condition of a plant may be interdependent and may result from each other. Each indicator is defined in the art and can be determined by methods known to a skilled person.

The compounds of the invention are also suitable for use against non-crop insect pests. For use against said non-crop pests, compounds of the present invention can be used as bait composition, gel, general insect spray, aerosol, as ultra-low volume application and bed net (impregnated or surface applied). Furthermore, drenching and rodding methods can be used.

As used herein, the term "non-crop insect pest" refers to pests, which are particularly relevant for non-crop targets, such as ants, termites, wasps, flies, ticks, mosquitos, crickets, or cockroaches.

The bait can be a liquid, a solid or a semisolid preparation (e.g. a gel). The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature (e.g. http://www.pherobase.com), and are known to those skilled in the art.

For use in bait compositions, the typical content of active ingredient is from 0.001 weight % to 15 weight %, desirably from 0.001 weight % to 5% weight % of active compound.

Formulations of the compounds of the present invention as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents, furthermore auxiliaries such as emulsifiers, perfume oils, if appropriate stabilizers, and, if required, propellants.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of the present invention and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of the present invention and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder.

The compounds of the present invention and its compositions can be used for protecting wooden materials such as trees, board fences, sleepers, frames, artistic artifacts, etc. and buildings, but also construction materials, furniture, leathers, fibers, vinyl articles, electric wires and cables etc. from ants and/or termites, and for controlling ants and termites from doing harm to crops or human being (e.g. when the pests invade into houses and public facilities).

Customary application rates in the protection of materials are, for example, from 0.001 g to 2000 g or from 0.01 g to 1000 g of active compound per m² treated material, desirably from 0.1 g to 50 g per m².

Insecticidal compositions for use in the impregnation of materials typically contain from 0.001 to 95 weight %, preferably from 0.1 to 45 weight %, and more preferably from 1 to 25 weight % of at least one repellent and/or insecticide.

The compounds of the the present invention are especially suitable for efficiently combating animal pests such as arthropods, gastropods and nematodes including but not limited to:

insects from the order of Lepidoptera, for example *Achroia grisella, Acleris* spp. such as *A. fimbriana, A. gloverana, A. variana; Acrolepiopsis assectella, Acronicta major, Adoxophyes* spp. such as *A. cyrtosema, A. orana; Aedia leucomelas, Agrotis* spp. such as *A. exclamationis, A. fucosa, A. ipsilon, A. orthogoma, A. segetum, A. subterranea; Alabama argillacea, Aleurodicus dispersus, Alsophila pometaria, Ampelophaga rubiginosa, Amyelois transitella, Anacampsis sarcitella, Anagasta kuehniella, Anarsia lineatella, Anisota senatoria, Antheraea pemyi, Anticarsia* (=*Thermesia*)spp. such as *A. gemmatalis; Apamea* spp., *Aproaerema modicella, Archips* spp. such as *A. argyrospila, A. fuscocupreanus, A. rosana, A. xyloseanus; Argyresthia conjugella, Argyroploce* spp., *Argyrotaenia* spp. such as *A. velutinana; Athetis mindara, Austroasca viridigrisea, Autographa gamma, Autographa nigrisigna, Barathra brassicae, Bedellia* spp., *Bonagota salubricola, Borbo cinnara, Bucculatrix thurberiella, Bupalus piniarius, Busseola* spp., *Cacoecia* spp. such as *C. murinana, C. podana; Cactoblastis cactorum, Cadra cautella, Calingo braziliensis, Calopas theivora, Capua reticulana, Carposina* spp. such as *C. niponensis, C. sasakii; Cephus* spp., *Chaetocnema aridula, Cheirnatobia brumata, Chilo* spp. such as *C. Indicus, C. suppressalis, C. partellus; Choreutis pariana, Choristoneura* spp. such as *C. conflictana, C. fumiferana, C. longicellana, C. murinana, C. occidentalis, C. rosaceana; Chrysodeixis* (=Pseudoplusia) spp. such as *C. eriosoma, C. includens; Cirphis unipuncta, Clysia ambiguella, Cnaphalocerus* spp., *Cnaphalocrocis medinalis, Cnephasia* spp., *Cochylis hospes, Coleophora* spp., *Colias eurytheme, Conopomorpha* spp., *Conotrachelus* spp., *Copitarsia* spp., *Corcyra cephalonica, Crambus caliginosellus, Crambus teterrellus, Crocidosema* (=Epinotia) *aporema, Cydalirna* (=Diaphania) *perspectalis, Cydia* (=Carpocapsa) spp. such as *C. pomonella, C. latiferreana; Dalaca noctuides, Datana integerrima, Dasychira pinicola, Dendrolimus* spp. such as *D. pint, D. spectabnis, D. sibiricus; Desmia Funeralis, Diaphania* spp. such as *D. nitidalis, D. hyalinata; Diatraea grandiosella, Diatraea saccharalis, Diphthera festiva, Earias* spp. such as *E. insulana, E. vittella; Ecdytolopha aurantianu, Egira* (=Xylomyges) *curtails, Elasmopalpus lignosellus, Eldana saccharina, Endopiza viteana, Ennomos subsignaria, Eoreuma loftini, Ephestia* spp. such as *E. cautella, E. elutella, E. kuehniella; Epinotia aporema, Epiphyas postvittana, Erannis tiliaria, Erionota thrax, Etiella* spp., *Eulia* spp., *Eupoecilia ambiguella, Euproctis chrysorrhoea, Euxoa* spp., *Evetria bouliana, Faronta albilinea, Feltia* spp. such as *F. subterranean; Galleria mellonella, Gracillaria* spp., *Grapholita* spp. such as *G. funebrana, G. molesta, G. inopinata; Halysidota* spp., *Harrisina americana, Hedylepta* spp., *Helicoverpa* spp. such as *H. armigera* (=Heliothis armigera), *H. zea* (=Heliothis zea); *Heliothis* spp. such as *H. assulta, H. subflexa, H. virescens; Hellula* spp. such as *H. undalis, H. rogatalis; Helocoverpa gelotopoeon, Hemileuca oliviae, Herpetogramma licarsisalis, Hibernia defoliaria, Hofmannophila pseudospretella, Homoeosoma electellum, Homona magnanima, Hypena scabra, Hyphantria cunea, Hyponomeuta padella, Hyponomeuta malinellus, Kakivoria flavofasciata, Keiferia lycopersicella, Lambdina fiscellaria fiscellaria, Lambdina fiscellaria lugubrosa, Lamprosema indicata, Laspeyresia molesta, Leguminivora glycinivorella, Lerodea eufala, Leucinodes orbonalis, Leucoma sands, Leucoptera* spp. such as *L. coffeella, L. scitella; Leuminivora lycinivorella, Lithocolletis blancardella, Lithophane antennata, Liattia octo* (=*Amyna axis*), *Lobesia botrana, Lophocampa* spp., *Loxagrotis albicosta, Loxostege* spp. such as *L. sticticalis, L. cereralis; Lymantria* spp. such as *L. dispar, L. monacha; Lyonetia clerkella, Lyonetia prunifoliella, Malacosoma* spp. such as *M. americanum, M. calitornicum, M. constrictum, M. neustria; Mamestra* spp. such as *M. brassicae, M. configurata; Mamstra brassicae, Manduca* spp. such as *M. quinquemaculata, M. sexta; Marasmia* spp, *Marmara* spp., *Maruca testulalis, Megalopyge Janata, Melanchra picta, Melanins leda, Mocis* spp. such as *M. lapites, M. repanda; Mocis latipes, Monochroa fragariae, Mythimna separata, Nemapogon cloacella, Neoleucinodes elegantalis, Nepytia* spp., *Nymphula* spp., *Oiketicus* spp., *Omiodes indicata, Omphisa anastomosalis, Operophtera brumata, Orgyia pseudotsugata, Oria* spp., *Orthaga thyrisalis, Ostrinia* spp. such as *O. nubilalis; Oulema oryzae, Paleacrita vernata, Panolis flammea, Parnara* spp., *Papaipema nebris, Papilio cresphontes, Paramyelois transitella, Paranthrene regalis, Paysandisia archon, Pectinophora* spp. such as *P. gossypiella; Peridroma saucia, Perneucoptera* spp., such as *P. coffeella; Phalera bucephala, Phryganidia calitornica, Phthorimaea* spp. such as *P. operculella; Phyllocnitis citrella, Phyllonorycter* spp. such as *P. blancardella, P. crataegella, P. issikii, P. ringoniella; Piers* spp. such as *P. brassicae, P. rapae, P. napi; Pilocrocis tripunctata, Plathypena scabra, Platynota* spp. such as *P. fiavedana, P. idaeusalis, P. stultana; Platyptilia carduidactyla, Plebejus argus, Plodia interpunctella, Plusia* spp, *Plutella maculipennis, Plutella xylostella, Pontia protodica, Prays* spp., *Prodenia* spp., *Proxenus lepigone, Pseudaletia* spp. such as *P. sequax, P. unipuncta; Pyrausta nubilalis, Rachiplusia nu, Richia albicosta, Rhizobius ventralis, Rhyacionia frustrana, Sabulodes aegrotata, Schizura concinna, Schoenobius* spp., *Schreckensteinia festaliella, Scirpophaga* spp. such as *S. incertulas, S. innotata; Scotia segetum, Sesamia* spp. such as *S. inferens, Seudyra subfiava, Sitotroga cerealella, Sparganothis pilleriana, Spilonota lechriaspis, S. ocellana, Spodoptera* (=Lamphygma) spp. such as *S. cosmoides, S. eridania, S. exigua, S. frugiperda, S. lafisfascia, S. littoralis, S. litura, S. omithogalli; Stigmella* spp., *Stomopteryx subsecivella, Strymon bazochii, Sylepta derogata, Synanthedon* spp. such as *S. exitiosa, Tecia solanivora, Telehin licus, Thaumatopoea pityocampa, Thaumatotibia* (=Ctyptophlebia) *leucotreta, Thaumetopoea pityocampa, Thecla* spp., *Theresimima ampelophaga, Thyrinteina* spp, *Tildenia inconspicuella, Tinea* spp. such as *T. cloacella, T. pellionella; Tineola bisselliella, Tortrix* spp. such as *T. viridana; Trichophaga tapetzella, Trichoplusia* spp. such as *T. ni; Tuta* (=Scrobipalpula) *absoluta, Udea* spp. such as *U. rubigalis, U rubigalis; Virachola* spp., *Yponomeuta padella,* and *Zeiraphera canadensis;* insects from the order of Coleoptera, for example *Acalymma vittatum, Acanthoscehdes obtectus, Adoretus* spp., *Agelastica alni, Agrilus* spp. such as *A. anxius, A. planipennis, A. sinuatus; Agriotes* spp. such as *A. fuscicollis, A. lineatus, A. obscurus; Alphitobius diaperinus, Amphimallus solstitialis, Anisandrus dispar, Anisoplia austriaca, Anobium punctatum, Anomala corpulenta, Anomala rufocuprea,*

*Anoplophora* spp. such as *A. glabripennis*; *Anthonomus* spp. such as *A. eugenit, A. grandis, A. pomorum*; *Anthrenus* spp., *Aphthona euphoridae, Apion* spp., *Apogonia* spp., *Athous haemorrhoidalis, Atomaria* spp. such as *A. linearis*; *Attagenus* spp., *Aulacophora femoralis, Blastophagus piniperda, Blitophaga undata, Bruchidius obtectus, Bruchus* spp. such as *B. lentis, B. pisorum, B. rufimanus*; *Byctiscus betulae, Callidiellum rufipenne, Callopistria floridensis, Callosobruchus chinensis, Cameraria ohridella, Cassida nebulosa, Cerotoma trifurcata, Cetonia aurata, Ceuthorhynchus* spp. such as *C. assimilis, C. napi*; *Chaetocnema tibialis, Cleonus mendicus, Conoderus* spp. such as *C. vespertinus*; *Conotrachelus nenuphar, Cosmopolites* spp., *Costelytra zealandica, Crioceris asparagi, Cryptolestes ferrugineus, Cryptorhynchus lapathi, Ctenicera* spp. such as *C. destructor*; *Curculio* spp., *Cylindrocopturus* spp., *Cyclocephala* spp., *Dactylispa balyi, Dectes texanus, Dermestes* spp., *Diabrotica* spp. such as *D. undecimpunctata, D. speciosa, D. longicomis, D. semipunctata, D. virgifera*; *Diaprepes* abbreviates, *Dichocrocis* spp., *Dicladispa armigera, Diloboderus abderus, Diocalandra frumenti* (*Diocalandra stigmaticollis*), *Enaphalodes rufulus, Epilachna* spp. such as *E. varivestis, E. vigintioctomaculata*; *Epitrix* spp. such as *E. hirtipennis, E. similaris*; *Eutheola humilis, Eutinobothrus brasiliensis, Faustinus cubae, Gibbium psylloides, Gnathocerus cornutus, Hellula undalis, Heteronychus arator, Hylamorpha elegans, Hylobius abietis, Hylotrupes bajulus, Hypera* spp. such as *H. brunneipennis, H. postica*; *Hypomeces squamosus, Hypothenemus* spp., *Ips typographus, Lachnosterna consanguinea, Lasioderma serricome, Latheticus oryzae, Lathridius* spp., *Lema* spp. such as *L. bilineata, L. melanopus*; *Leptinotarsa* spp. such as *L. decemlineata*; *Leptispa pygmaea, Limonius californicus, Lissorhoptrus oryzophilus, Lixus* spp., *Luperodes* spp., *Lyctus* spp. such as *L. bruneus*; *Liogenys fuscus, Macrodactylus* spp. such as *M. subspinosus*; *Maladera matrida, Megaplatypus mutates, Megascelis* spp., *Melanotus communis, Meligethes* spp. such as *M. aeneus*; *Melolontha* spp. such as *M. hippocastani, M. melolontha*; *Metamasius hemipterus, Microtheca* spp., *Migdolus* spp. such as *M. fryanus, Monochamus* spp. such as *M. alternatus*; *Naupactus xanthographus, Niptus hololeucus, Oberia brevis, Oemona hirta, Oryctes rhinoceros, Oryzaephilus surinamensis, Oryzaphagus oryzae, Otiorrhynchus sulcatus, Otiorrhynchus ovatus, Otiorrhynchus sulcatus, Oulema melanopus, Oulema oryzae, Oxycetonia jucunda, Phaedon* spp. such as *P. brassicae, P. cochleariae*; *Phoracantha recurva, Phyllobius pyri, Phyllopertha horticola, Phyllophaga* spp. such as *P. helleri*; *Phyllotreta* spp. such as *P. chrysocephala, P. nemorum, P. striolata, P. vittula*; *Phyllopertha horticola, Popillia japonica, Premnotrypes* spp., *Psacothea Maris, Psylliodes chrysocephala, Prostephanus truncates, Psylliodes* spp., *Ptinus* spp., *Pulga saltona, Rhizopertha dominica, Rhynchophorus* spp. such as *R. billineatus, R. ferrugineus, R. palmarum, R. phoenicis, R. vulneratus*; *Saperda candida, Scolytus schevyrewi, Scyphophorus acupunctatus, Sitona lineatus, Sitophilus* spp. such as *S. granaria, S. oryzae, S. zeamais*; *Sphenophorus* spp. such as *S. levis*; *Stegobium paniceum, Sternechus* spp. such as *S. subsignatus*; *Strophomorphus ctenotus, Symphyietes* spp., *Tanymecus* spp., *Tenebrio molitor, Tenebrioides mauretanicus, Tribolium* spp. such as *T. castaneum*; *Trogoderma* spp., *Tychius* spp., *Xylotrechus* spp. such as *X. pyrrhoderus*; and, *Zabrus* spp. such as *Z. tenebrioides*;

insects from the order of Diptera for example *Aedes* spp. such as *A. aegypti, A. albopictus, A. vexans*; *Anastrepha ludens, Anopheles* spp. such as *A. albimanus, A. crucians, A. freeborn, A. gambiae, A. leucosphyrus, A. maculipennis, A. minimus, A. quadrimaculatus, A. sinensis*; *Bactrocera invadens, Bibio hortulanus, Calliphora erythrocephala, Calliphora vicina, Ceratitis capitata, Chrysomyia* spp. such as *C. bezziana, C. hominivorax, C. macellaria*; *Chrysops atlanticus, Chrysops discalis, Chrysops silacea, Cochliomyia* spp. such as *C. hominivorax*; *Contarinia* spp. such as *C. sorghicola*; *Cordylobia anthropophaga, Culex* spp. such as *C. nigripalpus, C. pipiens, C. quinquefasciatus, C. tarsalis, C. tritaeniorhynchus*; *Culicoides furens, Culiseta inomata, Cultiseta melanura, Cuterebra* spp., *Dacus cucurbitae, Dacus oleae, Dasineura brassicae, Dasineura oxycoccana, Delta* spp. such as *D. antique, D. coarctata, D. platura, D. radicum*; *Dermatobia hominis, Drosophila* spp. such as *D. suzukit, Fannia* spp. such as *F. canicularis*; *Gastraphilus* spp. such as *G. intestinalis*; *Geomyza tipunctata, Glossina* spp. such as *G. fuscipes, G. morsitans, G. palpalis, G. tachinoides*; *Haematobia irritans, Haplodiplosis equestris, Hippelates* spp., *Hylemyia* spp. such as *H. platura*; *Hypoderma* spp. such as *H. lineata*; *Hyppobosca* spp., *Hydrellia philippina, Leptoconops torrens, Liriomyza* spp. such as *L. sativae, L. trifolii*; *Lucilia* spp. such as *L. caprina, L. cuprina, L. sericata*; *Lycoria pectoralis, Mansonia titillanus, Mayetiola* spp. such as *M. destructor*; *Musca* spp. such as *M. autumnalis, M. domestica*; *Muscina stabulans, Oestrus* spp. such as *O. ovis*; *Opomyza forum, Oscinella* spp. such as *O. frit*; *Orseolia oryzae, Pegomya hysocyami, Phlebotomus argentipes, Phorbia* spp. such as *P. antiqua, P. brassicae, P. coarctata*; *Phytomyza gymnostoma, Prosimulium mixtum, Psila rosae, Psorophora columbiae, Psorophora discolor, Rhagoletis* spp. such as *R. cerasi, R. cingulate, R. indifferens, R. mendax, R. pomonella*; *Rivellia quadrifasciata, Sarcophaga* spp. such as *S. haemorrhoidalis*; *Simulium vittatum, Sitodiplosis mosellana, Stomoxys* spp. such as *S. calcitrans*; *Tabanus* spp. such as *T. atratus, T. bovinus, T. lineola, T. similis*; *Tannia* spp., *Thecodiplosis japonensis, Tipula oleracea, Tipula paludosa*, and *Wohlfahrtia* spp;

insects from the order of Thysanoptera for example, *Baliothrips biformis, Dichromothrips corbetti, Dichromothrips* ssp., *Echinothrips americanus, Enneothrips Havens, Frankliniella* spp. such as *F. fusca, F. occidentalis, F. tritici*; *Heliothrips* spp., *Hercinothrips femoralis, Kakothrips* spp., *Microcephalothrips abdominalis, Neohydatothrips samayunkur, Pezothrips kellyanus, Rhipiphorothrips cruentatis, Scirtothrips* spp. such as *S. citri*; *S. dorsalis, S. perseae*; *Stenchaetothrips* spp, *Taeniothrips cardamoni, Taeniothrips inconsequens, Thrips* spp. such as *T. imagines, T. hawaiiensis, T. oryzae, T. palmi, T. parvispinus, T. tabaci*;

insects from the order of Hemiptera for example, *Acizzia jamatonica, Acrosternum* spp. such as *A. hilare*; *Acyrthosipon* spp. such as *A. onobrychis, A. pisum*; *Adelges laricis, Adelges tsugae, Adelphocoris* spp., such as *A. rapidus, A. superbus*; *Aeneolamia* spp., *Agonoscena* spp., *Aulacorthum solani, Aleurocanthus woglumi, Aleurodes* spp., *Aleurodicus disperses, Aleurolobus barodensis, Aleurothrixus* spp., *Amrasca* spp., *Anasa tristis, Antestiopsis* spp., *Anuraphis cardui, Aonidiella* spp., *Aphanostigma piri, Aphidula nasturtii, Aphis* spp. such as *A. craccivora, A. fabae, A. forbesi, A. gossypii, A. grossulariae, A. maidiradicis, A. pomi, A. sambuci, A. schneideri, A. spiraecola*; *Arboridia apicalis, Arilus critatus, Aspidiella* spp., *Aspidiotus* spp., *Atanus* spp., *Aulacaspis yasumatsui, Aulacorthum solani, Bactericera cockerelli* (*Paratrioza cockerelli*), *Bemisia* spp. such as *B. argentifolii, B. tabaci* (*Aleurodes tabaci*); *Blissus* spp. such as *B. leucopterus*; *Brachycaudus* spp. such as *B. cardui, B. helichrysi, B. persicae, B. prunicola*; *Brachycolus* spp.,

*Brachycorynella asparagi, Brevicoryne brassicae, Cacopsylla* spp. such as *C. fulguralis, C. pyricola (Psylla piri); Calligypona marginate, Calocoris* spp., *Campylomma livida, Capitophorus horni, Carneocephala fulgida, Cavelerius* spp., *Ceraplastes* spp., *Ceratovacuna lanigera, Ceroplastes ceriferus, Cerosipha gossypii, Chaetosiphon fragaefolii, Chionaspis tegalensis, Chlorita onukii, Chromaphis juglandicola, Chrysomphalus ficus, Cicadulina mbila, Cimex* spp. such as *C. hemipterus, C. lectularius; Coccomytilus halli, Coccus* spp. such as *C. hesperidum, C. pseudomagnoliarum; Corythucha arcuata, Creontiades dilutus, Cryptomyzus ribis, Chrysomphalus aonidum, Cryptomyzus ribis, Ctenarytaina spatulata, Cyrtopeltis notatus, Dalbulus* spp., *Dasynus piperis, Dialeurodes* spp. such as *D. citrifolii; Dalbulus maidis, Diaphorina* spp. such as *D. citri; Diaspis* spp. such as *D. bromeliae; Dichelops furcatus, Diconocoris hewetti, Doralis* spp., *Dreyfusia nordmannianae, Dreyfusia piceae, Drosicha* spp., *Dysaphis* spp. such as *D. plantaginea, D. pyri, D. radicola; Dysaulacorthum pseudosolani, Dysdercus* spp. such as *D. cingulatus, D. intermedius; Dysmicoccus* spp., *Edessa* spp., *Geocoris* spp., *Empoasca* spp. such as *E. fabae, E. solana; Epidiaspis leperii, Eriosoma* spp. such as *E. lanigerum, E. pyricola; Erythroneura* spp., *Eurygaster* spp. such as *E. integriceps; Euscelis bilobatus, Euschistus* spp. such as *E. heros, E. impictiventris, E. servus; Fiorinia theae, Geococcus coffeae, Glycaspis brimblecombei, Halyomorpha* spp. such as *H. halys; Heliopeltis* spp., *Homalodisca vitripennis (=H. coagulata), Horcias nobilellus, Hyalopterus pruni, Hyperomyzus lactucae, Icerya* spp. such as *I. purchase; Idiocerus* spp., *Idioscopus* spp., *Laodelphax striatellus, Lecanium* spp., *Lecanoideus floccissimus, Lepidosaphes* spp. such as *L. ulmi; Leptocorisa* spp., *Leptoglossus phyllopus, Lipaphis erysimi, Lygus* spp. such as *L. hesperus, L. lineolaris, L. pratensis; Maconellicoccus hirsutus, Marchalina hellenica, Macropes excavatus, Macrosiphum* spp. such as *M. rosae, M. avenae, M. euphorbiae; Macrosteles quadrilineatus, Mahanarva fimbriolata, Megacopta cribraria, Megoura viciae, Melanaphis pyrarius, Melanaphis sacchari, Melanocallis (=Tinocallis) calyaefoliae, Metcafiella* spp., *Metopolophium dirhodum, Monellia costalis, Monelliopsis pecanis, Myzocallis coryli, Murgantia* spp., *Myzus* spp. such as *M. ascalonicus, M. cerasi, M. nicotianae, M. persicae, M. varians; Nasonovia ribis nigri, Neotoxoptera formosana, Neomegalotomus* spp, *Nephotettix* spp. such as *N. malayanus, N. nigropictus, N. parvus, N. virescens; Nezara* spp. such as *N. viridula; Nilaparvata lugens, Nysius huttoni, Oebalus* spp. such as *O. pugnax; Oncometopia* spp., *Orthezia praelonga, Oxycaraenus hyalinipennis, Parabemisia myricae, Parlatoria* spp., *Parthenolecanium* spp. such as *P. corni, P. persicae; Pemphigus* spp. such as *P. bursarius, P. populivenae; Peregrinus maidis, Perkinsiella saccharicida, Phenacoccus* spp. such as *P. aceris, P. gossypii; Phloeomyzus passerinii, Phorodon humuli, Phylloxera* spp. such as *P. devastatrix, Piesma quadrata, Piezodorus* spp. such as *P. guildinii; Pinnaspis aspidistrae, Planococcus* spp. such as *P. citri, P. ficus; Prosapia bicincta, Protopulvinaria pyriformis, Psallus seriatus, Pseudacysta persea, Pseudaulacaspis pentagons, Pseudococcus* spp. such as *P. comstocki; Psylla* spp. such as *P. mali; Pteromalus* spp., *Pulvinaria amygdali, Pyrilla* spp., *Quadraspidiotus* spp., such as *Q. perniciosus; Quesada gigas, Rastrococcus* spp., *Reduvius senilis, Rhizoecus americanus, Rhodnius* spp., *Rhopalomyzus ascalonicus, Rhopalosiphum* spp. such as *R. pseudobrassicas, R. insertum, R. maidis, R. padi; Sagatodes* spp., *Sahlbergella singularis, Saissetia* spp., *Sappaphis mala, Sappaphis mali, Scaptocoris* spp., *Scaphoides titanus, Schizaphis graminum, Schizoneura lanuginosa, Scotinophora* spp., *Selenaspidus articulatus, Sitobion avenae, Sogata* spp., *Sogatella furcifera, Solubea insularis, Spissistilus festinus (=Stictocephala festina), Stephanitis nashi, Stephanitis pyrioides, Stephanitis takeyai, Tenalaphara malayensis, Tetraleurodes perseae, Therioaphis maculate, Thyanta* spp. such as *T. accerra, T. perditor; Tibraca* spp., *Tomaspis* spp., *Toxoptera* spp. such as *T. aurantii; Trialeurodes* spp. such as *T. abutilonea, T. ricini, T. vaporariorum; Triatoma* spp., *Trioza* spp., *Typhlocyba* spp., *Unaspis* spp. such as *U. citri, U. yanonensis;* and *Viteus vitifolii,*

Insects from the order Hymenoptera for example *Acanthomyops interjectus, Athalia rosae, Atta* spp. such as *A. capiguara, A. cephalotes, A. cephalotes, A. laevigata, A. robusta, A. sexdens, A. texana, Bombus* spp., *Brachymyrmex* spp., *Camponotus* spp. such as *C. floridanus, C. pennsylvanicus, C. modoc; Cardiocondyla nuda, Chalibion* sp, *Crematogaster* spp., *Dasymutilla occidentalis, Diprion* spp., *Dolichovespula maculata, Dorymyrmex* spp., *Dryocosmus kuriphilus, Formica* spp., *Hoplocampa* spp. such as *H. minuta, H. testudinea; Iridomyrmex humilis, Lasius* spp. such as *L. niger, Linepithema humile, Liometopum* spp., *Leptocybe invasa, Monomorium* spp. such as *M. pharaonis, Monomorium, Nylandria fulva, Pachycondyla chinensis, Paratrechina longicomis, Paravespula* spp., such as *P. germanica, P. pennsylvanica, P. vulgaris; Pheidole* spp. such as *P. megacephala; Pogonomyrmex* spp. such as *P. barbatus, P. californicus, Polistes rubiginosa, Prenolepis impairs, Pseudomyrmex gracilis, Schelipron* spp., *Sirex cyaneus, Solenopsis* spp. such as *S. geminata, S. invicta, S. molesta, S. richteri, S. xyloni, Sphecius speciosus, Sphex* spp., *Tapinoma* spp. such as *T. melanocephalum, T. sessile; Tetramorium* spp. such as *T. caespitum, T. bicarinatum, Vespa* spp. such as *V. crabro; Vespula* spp. such as *V. squamosal; Wasmannia auropunctata, Xylocopa* sp;

Insects from the order Orthoptera for example *Acheta domesticus, Calliptamus italicus, Chortoicetes terminifera, Ceuthophilus* spp., *Diastrammena asynamora, Dociostaurus maroccanus, Gryllotalpa* spp. such as *G. africana, G. gryllotalpa; Gryllus* spp., *Hieroglyphus daganensis, Kraussaria angulifera, Locusta* spp. such as *L. migratoria, L. pardalina; Melanoplus* spp. such as *M. bivittatus, M. femurrubrum, M. mexicanus, M. sanguinipes, M. spretus; Nomadacris septemfasciata, Oedaleus senegalensis, Scapteriscus* spp., *Schistocerca* spp. such as *S. americana, S. gregaria, Stemopelmatus* spp., *Tachycines asynamorus,* and *Zonozerus variegatus;*

Pests from the Class Arachnida for example Acari, e.g. of the families Argasidae, Ixodidae and Sarcoptidae, such as *Amblyomma* spp. (e.g. *A. americanum, A. variegatum, A. maculatum), Argas* spp. such as *A. persicu), Boophilus* spp. such as *B. annulatus, B. decoloratus, B. microplus, Dermacentor* spp. such as *D. silvarum, D. andersoni, D. variabilis, Hyalomma* spp. such as *H. truncatum, Ixodes* spp. such as *I. ricinus, I. rubicundus, I. scapularis, I. holocyclus, I. pacificus, Rhipicephalus sanguineus, Ornithodorus* spp. such as *O. moubata, O. hermsi, O. turicata, Omithonyssus bacoti, Otobius megnini, Dermanyssus gallinae, Psoroptes* spp. such as *P. ovis, Rhipicephalus* spp. such as *R. sanguineus, R. appendiculatus, Rhipicephalus evertsi, Rhizoglyphus* spp., *Sarcoptes* spp. such as *S. Scabiei;* and Family Eriophyidae including *Aceria* spp. such as *A. sheldoni, A. anthocoptes, Acallitus* spp., *Aculops* spp. such as *A. lycopersici, A. pelekassi; Aculus* spp. such as *A. schlechtendali; Colomerus vitis, Epitrimerus gyri, Phyllocoptruta oleivora; Eriophytes ribis* and *Eriophyes* spp. such as *Eriophyes sheldoni;* Family Tarsonemidae including *Hemitarsonemus* spp., *Phytonemus* pallidus and Polyphagotarsonemus latus, Stenotarsonemus spp. Steneotarsonemus spinki; Family Tenuipalpidae including Brevipalpus spp. such as B. phoenicis; Family Tetranychidae including Eotetranychus spp., Eutetranychus spp., Oligonychus spp., Petrobia latens, Tetranychus spp. such as T. cinnabarinus, T. evansi, T. kanzawai, T. pacificus, T. phaseulus, T. telarius and T. urticae; Blyobia praetiosa; Panonychus spp. such as P. ulmi, P. citri; Metatetranychus spp. and Oligonychus spp. such as O. pratensis, O. perseae, Vasates lycopersici; Raoiella indica, Family Carpoglyphidae including Carpoglyphus spp.; Penthaleidae spp. such as Halotydeus destructor; Family Demodicidae with species such as Demodex spp.; Family Trombicidea including Trombicula spp.; Family Macronyssidae including Omothonyssus spp.; Family Pyemotidae including Pyemotes tritici; Tyrophagus putrescentiae; Family Acaridae including Acarus siro; Family Araneida including Latrodectus mactans, Tegenaria agrestis, Chiracanthium sp, Lycosa sp Achaearanea tepidariorum and Loxosceles reclusa;

Pests from the Phylum Nematoda, for example, plant parasitic nematodes such as root-knot nematodes, Meloidogyne spp. such as M. hapla, M. incognita, M. javanica; cyst-forming nematodes, Globodera spp. such as G. rostochiensis; Heterodera spp. such as H. avenae, H. glycines, H. schachtii, H. trifolii; Seed gall nematodes, Anguina spp.; Stem and foliar nematodes, Aphelenchoides spp. such as A. bessenyi; Sting nematodes, Belonolaimus spp. such as B. longicaudatus; Pine nematodes, Bursaphelenchus spp. such as B. lignicolus, B. xylophilus; Ring nematodes, Criconema spp., Criconemella spp. such as C. xenoplax and C. ornata; and, Criconemoides spp. such as Criconemoides informis; Mesocriconema spp.; Stem and bulb nematodes, Ditylenchus spp. such as D. destructor, D. dipsaci; Awl nematodes, Dolichodorus spp.; Spiral nematodes, Heliocotylenchus multicinctus; Sheath and sheathoid nematodes, Hemicycliophora spp. and Hemicriconemoides spp.; Hirshmanniella spp.; Lance nematodes, Hoploaimus spp.; False rootknot nematodes, Nacobbus spp.; Needle nematodes, Longidorus spp. such as L. elongatus; Lesion nematodes, Pratylenchus spp. such as P. brachyurus, P. neglectus, P. penetrans, P. curvitatus, P. goodeyi; Burrowing nematodes, Radopholus spp. such as R. similis; Rhadopholus spp.; Rhodopholus spp.; Reniform nematodes, Rotylenchus spp. such as R. robustus, R. reniformis; Scutellonema spp.; Stubby-root nematode, Trichodorus spp. such as T. obtusus, T. primitivus; Paratrichodorus spp. such as P. minor; Stunt nematodes, Tylenchorhynchus spp. such as T. claytoni, T. dubius; Citrus nematodes, Tylenchulus spp. such as T. semipenetrans; Dagger nematodes, Xiphinema spp.; and other plant parasitic nematode species;

Insects from the order Isoptera for example Calotermes flavicollis, Coptotermes spp. such as C. formosanus, C. gestroi, C. acinaciformis; Cornitermes cumulans, Cryptotermes spp. such as C. brevis, C. cavifrons; Globitermes sulfureus, Heterotermes spp. such as H. aureus, H. longiceps, H. tenuis; Leucotermes fiavipes, Odontotermes spp., Incisitermes spp. such as I. minor, I. Snyder; Marginitermes hubbardi, Mastotermes spp. such as M. darwiniensis Neocapritermes spp. such as N. opacus, N. parvus; Neotermes spp., Procornitermes spp., Zootermopsis spp. such as Z. angusticollis, Z. nevadensis, Reticulitermes spp. such as R. hesperus, R. tibialis, R. speratus, R. flavipes, R. grassei, R. lucifugus, R. santonensis, R. virginicus; Termes natalensis, Insects from the order Blattaria for example Blatta spp. such as B. orientalis, B. lateralis; Blattella spp. such as B. asahinae, B. germanica; Leucophaea maderae, Panchlora nivea, Periplaneta spp. such as P. americana, P. australasiae, P. brunnea, P. fuligginosa, P. japonica; Supella longipalpa, Parcoblatta pennsylvanica, Eutycotis floridana, Pycnoscelus surinamensis, Insects from the order Siphonoptera for example Cediopsylla simples, Ceratophyllus spp., Ctenocephalides spp. such as C. felis, C. canis, Xenopsylla cheopis, Pulex irritans, Trichodectes canis, Tunga penetrans, and Nosopsyllus fasciatus, Insects from the order Thysanura for example Lepisma saccharina, Ctenolepisma urbana, and Thermobia domestica, Pests from the class Chilopoda for example Geophilus spp., Scutigera spp. such as Scutigera coleoptrata;

Pests from the class Diplopoda for example Blaniulus guttulatus, Julus spp., Narceus spp., Pests from the class Symphyla for example Scutigerella immaculata, Insects from the order Dermaptera, for example Forficula auricularia, Insects from the order Collembola, for example Onychiurus spp., such as Onychiurus armatus, Pests from the order Isopoda for example, Armadillidium vulgare, Oniscus asellus, Porcellio scaber, Insects from the order Phthiraptera, for example Damalinia spp., Pediculus spp. such as Pediculus humanus capitis, Pediculus humanus corporis, Pediculus humanus humanus; Pthirus pubis, Haematopinus spp. such as Haematopinus eurysternus, Haematopinus suis; Linognathus spp. such as Linognathus vituli; Bovicola bovis, Menopon gallinae, Menacanthus stramineus and Solenopotes capillatus, Trichodectes spp., Examples of further pest species which may be controlled by compounds of fomula (I) include: from the Phylum Mollusca, class Bivalvia, for example, Dreissena spp.; class Gastropoda, for example, Arion spp., Biomphalaria spp., Bulinus spp., Deroceras spp., Galba spp., Lymnaea spp., Oncomelania spp., Pomacea canaliclata, Succinea spp.; from the class of the helminths, for example, Ancylostoma duodenale, Ancylostoma ceylanicum, Acylostoma braziliensis, Ancylostoma spp., Ascaris lubricoides, Ascaris spp., Brugia malayi, Brugia timori, Bunostomum spp., Chabertia spp., Clonorchis spp., Cooperia spp., Dicrocoelium spp., Dictyocaulus filaria, Diphyllobothrium latum, Dracunculus medinensis, Echinococcus granulosus, Echinococcus multilocularis, Enterobius vermicularis, Faciola spp., Haemonchus spp. such as Haemonchus contortus; Heterakis spp., Hymenolepis nana, Hyostrongulus spp., Loa Loa, Nematodirus spp., Oesophagostomum spp., Opisthorchis spp., Onchocerca volvulus, Ostertagia spp., Paragonimus spp., Schistosomen spp., Strongyloides fuelleborni, Strongyloides stercora lis, Stronyloides spp., Taenia saginata, Taenia solium, Trichinella spiralis, Trichinella nativa, Trichinella britovi, Trichinella nelsoni, Trichinella pseudopsiralis, Trichostrongulus spp., Trichuris trichuria, Wuchereria bancrofti.

The compounds of the present invention are suitable for use in treating or protecting animals against infestation or infection by parasites. Therefore, the present invention also relates to the use of a compound of the present invention for the manufacture of a medicament for the treatment or protection of animals against infestation or infection by parasites. Furthermore, the present invention relates to a method of treating or protecting animals against infestation and infection by parasites, which comprises orally, topically or parenterally administering or applying to the animals a parasiticidally effective amount of a compound of the present invention.

The present invention also relates to the non-therapeutic use of compounds of the present invention for treating or protecting animals against infestation and infection by parasites. Moreover, the present invention relates to a non-therapeutic method of treating or protecting animals against infestation and infection by parasites, which comprises applying to a locus a parasiticidally effective amount of a compound of the present invention.

The compounds of the present invention are further suitable for use in combating or controlling parasites in and on animals. Furthermore, the present invention relates to a method of combating or controlling parasites in and on animals, which comprises contacting the parasites with a parasitically effective amount of a compound of the present invention.

The present invention also relates to the non-therapeutic use of compounds of the present invention for controlling or combating parasites. Moreover, the present invention relates to a non-therapeutic method of combating or controlling parasites, which comprises applying to a locus a parasiticidally effective amount of a compound of the present invention.

The compounds of the present invention can be effective through both contact (via soil, glass, wall, bed net, carpet, blankets or animal parts) and ingestion (e.g. baits). Furthermore, the compounds of the present invention can be applied to any and all developmental stages.

The compounds of the present invention can be applied as such or in form of compositions comprising the compounds of the present invention.

The compounds of the present invention can also be applied together with a mixing partner, which acts against pathogenic parasites, e.g. with synthetic coccidiosis compounds, polyetherantibiotics such as Amprolium, Robenidin, Toltrazuril, Monensin, Salinomycin, Maduramicin, Lasalocid, Narasin or Semduramicin, or with other mixing partners as defined above, or in form of compositions comprising said mixtures.

The compounds of the present invention and compositions comprising them can be applied orally, parenterally or topically, e.g. dermally. The compounds of the present invention can be systemically or non-systemically effective.

The application can be carried out prophylactically, therapeutically or non-therapeutically. Furthermore, the application can be carried out preventively to places at which occurrence of the parasites is expected.

As used herein, the term "contacting" includes both direct contact (applying the compounds/compositions directly on the parasite, including the application directly on the animal or excluding the application directly on the animal, e.g. at it's locus for the latter) and indirect contact (applying the compounds/compositions to the locus of the parasite). The contact of the parasite through application to its locus is an example of a non-therapeutic use of the compounds of the present invention.

The term "locus" means the habitat, food supply, breeding ground, area, material or environment in which a parasite is growing or may grow outside of the animal.

As used herein, the term "parasites" includes endo- and ectoparasites. In some embodiments of the present invention, endoparasites can be preferred. In other embodiments, ectoparasites can be preferred. Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of the present invention are especially useful for combating parasites of the following orders and species, respectively:

fleas (Siphonaptera), e.g. *Ctenocephalides felts, Ctenocephalides canis, Xenopsylla cheopis, Pulex irritans, Tunga penetrans,* and *Nosopsyllus fasciatus*; cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae,* and *Blatta orientalis*; flies, mosquitoes (Diptera), e.g. *Aedes aegypti, Aedes albopictus, Aedes vexans, Anastrepha ludens, Anopheles maculipennis, Anopheles crucians, Anopheles albirnanus, Anopheles gambiae, Anopheles Freeborni, Anopheles leucosphyrus, Anopheles minimus, Anopheles quadrirnaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inomata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprin, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola,* and *Tabanus similis*; lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus*; ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabills, Amblyomma americanum, Amblyomma maculatum, Ornithodorus hermsi, Ornithodorus turicata* and parasitic mites (Mesostigmata), e.g. *Ornithonyssus bacofi* and *Dermanyssus gallinae*; Actinedida (Prostigmata) and Acaridida (Astigmata), e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp; Bugs (Heteropterida): *Cirnex lectularius, Cimex hemipterus, Reduvius senilis, Triatoma* spp., *Rhodnius* ssp., *Panstrongylus* ssp., and *Arilus critatus*; Anoplurida, e.g. *Haematopinus* spp., *Linognathus* spp., *Pediculus* spp., *Phtirus* spp., and *Solenopotes* spp.; Mallophagida (suborders Arnblycerina and lschnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp.; Roundworms Nematoda: Wipeworms and Trichinosis (Trichosyringida), e.g. Trichinellidae (*Trichinella* spp.), (Trichuridae) *Trichuris* spp., *Capillaria* spp.; Rhabditida, e.g. *Rhabditis* spp., *Strongyloides* spp., *Helicephalobus* spp.; Strongylida, e.g. *Strongylus* spp., *Ancylostoma* spp., *Necator americanus, Bunostomum* spp. (Hookworm), *Trichostrongylus* spp., *Haemonchus contortus, Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp., *Aleurostrongylus abstrusus*, and *Dioctophyma renale*; Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi*; Camallanida, e.g. *Dracunculus medinensis* (guinea worm); Spirurida, e.g. *Thelazia* spp., *Wuchereria* spp., *Brugia* spp., *Onchocerca* spp., *Dirofilari* spp.a, *Dipetalonema* spp., *Setaria* spp., *Elaeophora* spp., *Spirocerca lupi*, and *Habronema* spp.; Thorny headed worms (Acanthocephala), e.g. *Acanthocephalus* spp., *Macracanthorhynchus hirudinaceus* and *Oncicola* spp.; Planarians (Plathelminthes): Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp.; Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

As used herein, the term "animal" includes warm-blooded animals (including humans) and fish. Preferred are mammals, such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels. Particularly preferred are domestic animals, such as dogs or cats.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

Generally, it is favorable to apply the compounds of the present invention in total amounts of 0.5 mg/kg to 100 mg/kg per day, preferably 1 mg/kg to 50 mg/kg per day.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable preparations are:

Solutions such as oral solutions, concentrates for oral administration after dilution, solutions for use on the skin or in body cavities, pouring-on formulations, gels;

Emulsions and suspensions for oral or dermal administration; semi-solid preparations;

Formulations in which the active compound is processed in an ointment base or in an oil-in-water or water-in-oil emulsion base;

Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further auxiliaries such as acids, bases, buffer salts, preservatives, and solubilizers. Suitable auxiliaries for injection solutions are known in the art. The solutions are filtered and filled sterile.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on. Solutions for use on the skin are prepared according to the state of the art and according to what is described above for injection solutions, sterile procedures not being necessary.

Gels are applied to or spread on the skin or introduced into body cavities. Gels are prepared by treating solutions which have been prepared as described in the case of the injection solutions with sufficient thickener that a clear material having an ointment-like consistency results. Suitable thickeners are known in the art.

Pour-on formulations are poured or sprayed onto limited areas of the skin, the active compound penetrating the skin and acting systemically. Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added. Suitable such auxiliaries are known in the art.

Emulsions can be administered orally, dermally or as injections. Emulsions are either of the water-in-oil type or of the oil-in-water type. They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances. Suitable hydrophobic phases (oils), suitable hydrophilic phases, suitable emulsifiers, and suitable further auxiliaries for emulsions are known in the art.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers. Suitable suspending agents, and suitable other auxiliaries for suspensions including wetting agents are known in the art.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form. Suitable auxiliaries for this purpose are known in the art.

The compositions which can be used in the invention can comprise generally from about 0.001 to 95% of the compound of the present invention.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formula I against endoparasites in concentrations of 10 ppm to 2 percent by weight, preferably of 0.05 to 0.9 percent by weight, very particularly preferably of 0.005 to 0.25 percent by weight.

Topical application may be conducted with compound-containing shaped articles such as collars, medallions, ear tags, bands for fixing at body parts, and adhesive strips and foils.

Generally it is favorable to apply solid formulations which release compounds of the present invention in total amounts of 10 mg/kg to 300 mg/kg, preferably 20 mg/kg to 200 mg/kg, most preferably 25 mg/kg to 160 mg/kg body weight of the treated animal in the course of three weeks.

EXAMPLES

The present invention is now illustrated in further details by the following examples, without imposing any limitation thereto.

With appropriate modification of the starting materials, the procedures as described in the examples below were used to obtain further compounds of formula I. The compounds obtained in this manner are listed in the Tables that follows, together with physical data.

Compounds can be characterized e.g. by coupled High Performance Liquid Chromatography/mass spectrometry (HPLC/MS), by $^1$H-NMR and/or by their melting points.

Analytical HPLC—Method 1: Phenomenex Kinetex 1,7 μm XB-C18 100A; 50×2,1 mm. Elution: acetonitrile+0.1% trifluoroacetic acid (TFA)/water+0.1% trifluoroacetic acid (TFA) in a ratio of from 5:95 to 95:5 in 1.5 minutes at 50° C. Method 2: BEH C18 1.7 μm; 50×2,1 mm. Elution: acetonitrile+0.1% formic acid (FA)/water+0.1% 0.1% formic acid (FA) in a ratio of from 5:95 to 95:5 in 5 minutes at 40° C.

$^1$H-NMR: The signals are characterized by chemical shift (ppm, δ [delta]) vs. tetramethylsilane, respectively CDCl$_3$ for $^{13}$C-NMR, by their multiplicity and by their integral (relative number of hydrogen atoms given). The following abbreviations are used to characterize the multiplicity of the signals: m=multiplet, q=quartet, t=triplet, d=doublet and s=singlet.

Abbreviations used are: d for day(s), h for hour(s), min for minute(s), r.t./room temperature for 20-25° C., Rt for retention time; DMSO for dimethyl sulfoxide, OAc for acetate, EtOAc for ethyl acetate, THF for tetrahydrofuran, m-CPBA for meta-chloroperbenzoic acid, Tf$_2$O for triflic anhydride, PE for petroleum ether, MeI for methyl iodide, dppfPdCl$_2$ for [1,1'-bis(diphenylphosphino)ferrocene]-dichloropalladium(II), DIPEA for diisopropylethylamine and t-BuOH for tert-butanol.

Example C-1

2-(2-chlorophenyl)-6-methyl-7-(trifluoromethyl)imidazo[1,2-c]pyrimidin-5-one (C-1 of Table 1)

Step 1: To a solution of triphosgene (29.6 g) in CH$_2$Cl$_2$ (200 mL) was added a solution of p-methoxybenzylamine (13.7 g) in CH$_2$Cl$_2$ (200 mL), followed by the dropwise addition of Et$_3$N (30 mL) in CH$_2$Cl$_2$ (100 mL). The resulting mixture was stirred at 25° C. for 14 h. Water (500 mL) was added and the reaction mixture was extracted with CH$_2$Cl$_2$ (3×200 mL). The organic layers were combined, washed with sat. NH$_4$C$_1$ (600 mL), brine (600 mL), dried over Na$_2$SO$_4$, filtered, and concentrated to afford 1-(isocyanatomethyl)-4-methoxy-benzene (17 g, crude) as yellow oil. $^1$H NMR (CDCl$_3$, 400 MHz) δ 7.26 (d, J=8.8 Hz, 2H), 6.95 (d, J=8.4 Hz, 2H), 4.45 (s, 2H), 3.85 (s, 3H).

Step 2: To a solution of ethyl (Z)-3-amino-4,4,4-trifluoro-but-2-enoate (19 g) in DMF (500 mL) was added NaH (6 g) in portions at 0° C. The reaction mixture was then stirred at 0° C. for 1 h. The mixture was then added to 1-(isocyanatomethyl)-4-methoxy-benzene (17 g) at 0° C. The resulting mixture was stirred at 0° C. to 25° C. for 14 h. The solvent was removed under reduced pressure and water (1 L) was added, and the organic layer was separated. The aqueous layer was extracted with EtOAc (3×500 mL). The organic layers were combined, washed with brine (500 mL), dried over Na$_2$SO$_4$, filtered, and concentrated to afford crude 3-[(4-methoxyphenyl)methyl]-6-(trifluoromethyl)-1H-pyrimidine-2,4-dione (15 g) as yellow oil. $^1$H NMR (MeOD, 400 MHz) δ 7.27 (d, J=8.8 Hz, 2H), 6.77 (d, J=8.4 Hz, 2H), 5.80 (s, 1H), 5.02 (s, 2H) 3.70 (s, 3H).

Step 3: To a solution of 3-[(4-methoxyphenyl)methyl]-6-(trifluoromethyl)-1H-pyrimidine-2,4-dione (35 g) and K$_2$CO$_3$ (16 g) in DMF (300 mL) was added MeI (16.5 g, 7.24 mL, 116.2 mmol) at 25° C. The resulting mixture was then stirred at 25° C. for 12 h. The solvent was removed under reduced pressure. Water (300 mL) was added and the organic layer was separated. The aqueous layer was extracted with EtOAc (3×300 mL). The organic layers were combined, washed with brine (500 mL), dried over Na$_2$SO$_4$, filtered, and concentrated to afford crude 3-[(4-methoxyphenyl)methyl]-1-methyl-6-(trifluoromethyl)pyrimidine-2,4-dione (30 g) as yellow solid. $^1$H NMR (MeOD, 400 MHz) δ 7.35 (d, J=8.8 Hz, 2H), 6.83 (d, J=8.8 Hz, 2H), 6.28 (s, 1H), 5.02 (s, 2H), 3.75 (s, 3H), 3.46 (s, 3H).

Step 4: To a solution of 3-[(4-methoxyphenyl)methyl]-1-methyl-6-(trifluoromethyl)pyrimidine-2,4-dione (30 g) in CH$_3$CN (200 mL) and water (50 mL) was added ceric ammonium nitrate (78.5 g) at 25° C. Then the reaction mixture was stirred at 25° C. for 14 h then an additional portion (50 g) of ceric ammonium nitrate was added. The resulting mixture was stirred at 25° C. for 14 h. Water (200 mL) was added and the organic layer was separated The aqueous layer was extracted with EtOAc (3×100 mL). The organic layers were combined, washed with aq. NaHCO$_3$ (500 mL), dried over Na$_2$SO$_4$, filtered, and concentrated. The residue was purified by silica gel chromatography (PE:EtOAc=10:1 to 1:1 gradient) to afford 1-methyl-6-(trifluoromethyl)pyrimidine-2,4-dione (8 g) as yellow solid. $^1$H NMR (MeOD, 400 MHz) δ 6.20 (s, 1H), 3.44 (s, 3H).

Step 5: To a solution of 1-methyl-6-(trifluoromethyl)pyrimidine-2,4-dione (8 g) in DCM (150 mL) and pyridine (30 mL) was added dropwise Tf$_2$O (36.7 g) at 0° C. The mixture was then stirred at 0° C. to 25° C. for 3 h. Gaseous ammonia was passed through MeOH (50 mL) at −700° C. for 20 mins and the resulting methanol ammonia solution was poured into the reaction mixture. The resulting mixture was stirred at 25° C. for 12 h. The solvent was removed under reduced pressure. The residue was purified by preparative HPLC to afford 4-amino-1-methyl-6-(trifluoromethyl)pyrimidin-2-one (3.4 g) as yellow solid. $^1$H NMR (DMSO-d$_6$, 400 MHz) δ 7.62 (s, 1H), 7.52 (s, 1H), 6.24 (s, 1H), 3.30 (s, 3H).

Step 6: A solution of 4-amino-1-methyl-6-(trifluoromethyl)pyrimidin-2-one (300 mg), 2-bromo-1-(2-chlorophenyl)ethanone (435 mg) in dimethylcarbonate (6 mL) was stirred at 110° C. for 13 h. The solvent was removed under reduced pressure. The residue was purified by preparative HPLC to afford 2-(2-chlorophenyl)-6-methyl-7-(trifluoromethyl)imidazo[1,2-c]pyrimidin-5-one (197 mg) as an off-white solid. $^1$H NMR (DMSO-d$_6$, 400 MHz) δ 8.38 (s, 1H), 8.14 (dd, J=2.0, 8.0 Hz, 1H), 7.59 (dd, J=1.2, 8.0 Hz, 1H), 7.53-7.38 (m, 3H), 3.59 (s, 3H).

Example C-4

2-(3-ethylsulfonyl-2-pyridyl)-3-methyl-7-(trifluoromethyl)-[1,2,4]triazolo[1,5-a]pyridin-5-one (C-4 of Table 2)

Step 1: A solution of ethyl 4,4,4-trifluoro-3-oxo-butanoate (46.0 g) and 2-(triphenylphosphoranylidene)acetonitrile (112.8 g) in ether (1 L) was stirred for 12 h at 20° C. The mixture was filtered and the filtrate was concentrated to give a residue, which was purified by chromatography (PE:EtOAc=10:1) to give ethyl 4-cyano-3-(trifluoromethyl)but-3-enoate (43.0 g, 83% yield) as light yellow oil. $^1$H NMR (CDCl$_3$, 400 MHz) δ 6.15 (s, 1H), 4.24 (q, J=7.2 Hz, 2H), 3.56 (s, 2H), 1.30 (t, J=7.2 Hz, 3H).

Step 2: To a solution of ethyl 4-cyano-3-(trifluoromethyl)but-3-enoate (43.0 g) in EtOH (500 mL) was added N$_2$H$_4$.H$_2$O (52.0 g), then the mixture was stirred for 12 h at 20° C. The mixture was filtered and the filtrate was concentrated to give a residue, which was purified by preparative HPLC to afford 1,6-diamino-4-(trifluoromethyl)pyridin-2-one (4.5 g) as an off-white solid.

Step 3: To a solution of 1,6-diamino-4-(trifluoromethyl)pyridin-2-one (7.0 g) in DMF (105 mL) was added MeI (5.1 g), then the mixture was sealed and stirred for 12 h at 70° C. The mixture was concentrated to give a residue, which was purified by preparative HPLC to afford 6-amino-1-(methylamino)-4-(trifluoromethyl)pyridin-2-one (2.8 g) as yellow solid. $^1$H NMR (CDCl$_3$, 400 MHz) δ 6.21 (d, J=1.8 Hz, 1H), 5.67 (d, J=1.9 Hz, 1H), 5.39 (br s, 2H), 2.76 (s, 3H).

Step 4: A mixture of 6-amino-1-(methylamino)-4-(trifluoromethyl)pyridin-2-one (1.5 g,) and 3-ethylsulfanylpyridine-2-carbaldehyde (1.2 g) in DMF (20 mL) was stirred at 130° C. for 12 h. The solvent was removed to afford 2-(3-ethylsulfanyl-2-pyridyl)-3-methyl-7-(trifluoromethyl)-1,2-dihydro-[1,2,4]triazolo[1,5-a]pyridin-5-one (2.5 g, crude) as light yellow solid.

Step 5: To a mixture of 2-(3-ethylsulfanyl-2-pyridyl)-3-methyl-7-(trifluoromethyl)-1,2-dihydro-[1,2,4]triazolo[1,5-a]pyridin-5-one (550 mg,) in CH$_2$Cl$_2$ (10 mL) was added m-CPBA (938 mg, 85% purity) and the mixture was stirred for 1 h at 25° C. The solvent was removed to give a residue, which was purified by preparative HPLC to afford 2-(3-ethylsulfonyl-2-pyridyl)-3-methyl-7-(trifluoromethyl)-1,2-dihydro-[1,2,4]triazolo[1,5-a]pyridin-5-one (45 mg) as off-white solid. $^1$H NMR (CDCl$_3$, 400 MHz) δ 8.69 (d, J=4.6 Hz, 1H), 8.38-8.33 (m, 1H), 7.56 (dd, J=4.9, 7.9 Hz, 1H), 6.49 (s, 1H), 6.22 (s, 1H), 6.18 (s, 1H), 5.86 (d, J=1.5 Hz, 1H), 4.09-3.99 (m, 1H), 3.98-3.88 (m, 1H), 1.39 (t, J=7.4 Hz, 3H).

Step 6: A mixture of 2-(3-ethylsulfonyl-2-pyridyl)-3-methyl-7-(trifluoromethyl)-1,2-dihydro-[1,2,4]triazolo[1,5-a]pyridin-5-one (200 mg,) and Pd/C (100 mg) in xylene (10 mL) was stirred for 12 h at 130° C. under O$_2$ (15 psi). The mixture was filtered and the filtrate was concentrated to give a residue, which was purified by preparative-HPLC to afford 2-(3-ethylsulfonyl-2-pyridyl)-3-methyl-7-(trifluoromethyl)-[1,2,4]triazolo[1,5-a]pyridin-5-one (38 mg, 17.4% yield) as light yellow solid. LC/MS t$_R$=2.39 min, M+1=389.

By analogous procedures to the procedure described above for example C-1, the following examples of formula I-A were prepared, wherein the substituents Ar, R$^1$, R$^2$, R$^x$, R$^4$ and X are as depicted in the Table 1.

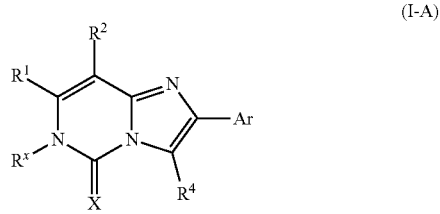

(I-A)

TABLE 1

| Example No | Ar | R¹ | R² | Rˣ | R⁴ | X | M + 1 | $t_R$ (min) |
|---|---|---|---|---|---|---|---|---|
| C-1 | 2-chlorophenyl | CF₃ | H | CH₃ | H | O | 329[2] | 3.48[2] |
| C-2 | 3-(ethylsulfonyl)pyridin-2-yl | CF₃ | H | CH₃ | H | O | 387[2] | 3.82[2] |
| C-5 | 3-(ethylsulfonyl)-5-(trifluoromethyl)pyridin-2-yl | CF₃ | H | CH₃ | H | O | 455 | 1.151 |
| C-6 | 4-bromo-2-(ethylsulfonyl)phenyl | CF₃ | H | CH₃ | H | O | 465.9 | 1.164 |
| C-7 | 3-methoxyphenyl | CF₃ | H | CH₃ | H | O | 324 | 1.126 |
| C-8 | thiazol-2-yl | CF₃ | H | CH₃ | H | O | 301 | 0.955 |
| C-9 | thiophen-2-yl | CF₃ | H | CH₃ | H | O | 300 | 1.086 |
| C-10 | 2-(trifluoromethyl)phenyl | CF₃ | H | CH₃ | H | O | 362 | 1.19 |
| C-11 | 2-methoxyphenyl | CF₃ | H | CH₃ | H | O | 324.1 | 1.142 |

TABLE 1-continued

| Example No | Ar | R¹ | R² | Rˣ | R⁴ | X | M + 1 | $t_R$ (min) |
|---|---|---|---|---|---|---|---|---|
| C-12 | 4-Br-C₆H₄ | CF₃ | H | CH₃ | H | O | 371.9 | 1.243 |
| C-13 | C₆H₅ | CF₃ | H | CH₃ | H | O | 294.1 | 1.114 |
| C-14 | 4-CN-C₆H₄ | CF₃ | H | CH₃ | H | O | 455 | 1.151 |
| C-15 | 2,4-Cl₂-C₆H₃ | CF₃ | H | CH₃ | H | O | 361.9 | 1.329 |
| C-16 | 4-CF₃-C₆H₄ | CF₃ | H | CH₃ | H | O | 361.9 | 1.261 |
| C-17 | 4-OCF₃-C₆H₄ | CF₃ | H | CH₃ | H | O | 378 | 1.277 |
| C-18 | 3,5-(CF₃)₂-C₆H₃ | CF₃ | H | CH₃ | H | O | 430 | 1.381 |
| C-19 | 3-OCF₃-C₆H₄ | CF₃ | H | CH₃ | H | O | 278 | 1.283 |
| C-20 | 5-Cl-thiophen-2-yl | CF₃ | H | CH₃ | H | O | 333.9 | 1.228 |
| C-21 | 4-Ph-C₆H₄ | CF₃ | H | CH₃ | H | O | 370 | 1.317 |
| C-22 | 2-Br-C₆H₄ | CF₃ | H | CH₃ | H | O | 186 | 1.213 |
| C-23 | 2-CF₃-4-F-C₆H₃ | CF₃ | H | CH₃ | H | O | 380 | 1.278 |

TABLE 1-continued

| Example No | Ar | R¹ | R² | Rˣ | R⁴ | X | M + 1 | $t_R$ (min) |
|---|---|---|---|---|---|---|---|---|
| C-24 | 2-(ethylsulfonyl)-4-phenylphenyl | CF₃ | H | CH₃ | H | O | 462 | 1.252 |
| C-25 | 2,6-difluorophenyl | CF₃ | H | CH₃ | H | O | 330 | 1.105 |
| C-26 | 3-(trifluoromethyl)phenyl | CF₃ | H | CH₃ | H | O | 362 | 1.258 |
| C-27 | 3,6-dichloropyridin-2-yl | CF₃ | H | CH₃ | H | O | 363 | 1.112 |
| C-28 | 4-bromo-2-(ethylthio)phenyl | CF₃ | H | CH₃ | H | O | 434 | 1.361 |
| C-29 | 2-(ethylsulfonyl)-5-(trifluoromethyl)pyridin-3-yl | OCH₂CF₃ | H | CH₃ | H | O | 417[2] | 2.15[2] |
| C-30 | 2-(ethylsulfonyl)thiophen-3-yl | CF₃ | H | CH₃ | H | O | 392 | 1.035 |
| C-31 | phenyl | CF₃ | H | CH₃ | CH₃ | O | 308 | 1.143 |

TABLE 1-continued

| Example No | Ar | $R^1$ | $R^2$ | $R^x$ | $R^4$ | X | M + 1 | $t_R$ (min) |
|---|---|---|---|---|---|---|---|---|
| C-32 | 3-Cl, 6-Ph-pyridin-2-yl | $CF_3$ | H | $CH_3$ | H | O | 405 | 1.259 |
| C-33 | 3-(ethylsulfonyl), 5-$CF_3$-pyridin-2-yl | $CF_3$ | H | $CH_3$ | H | S | 471 | 1.269 |
| C-34 | 3-(ethylsulfonyl), 5-Ph-pyridin-2-yl | $CF_3$ | H | $CH_3$ | H | O | 463 | 1.20 |
| C-35 | 3-(ethylsulfonyl), 5-cyclopropyl-pyridin-2-yl | $CF_3$ | H | $CH_3$ | H | O | 427 | 1.09 |
| C-36 | 3-(ethylsulfonyl), 5-(4-Cl-phenyl)-pyridin-2-yl | $CF_3$ | H | $CH_3$ | H | O | 497 | 1.304 |

1) Analytical HPLC - Method 1 unless otherwise stated;
2) Analytical HPLC - Method 2

By analogous procedures to the procedure described above for example C-4, the following examples of formula I-B were prepared, wherein the substituents Ar, $R^1$, $R^2$, $R^3$, $R^y$ and X are as depicted in the Table 2.

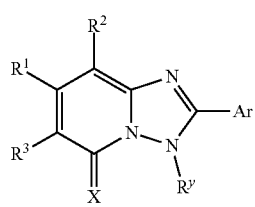

(I-B)

TABLE 2

| Example No | Ar | R¹ | R² | R³ | Rʸ | X | Physicochemical data: HPLC-Retention [mm][1] M + 1 | $t_R$ (min) |
|---|---|---|---|---|---|---|---|---|
| C-3 | 2-chlorophenyl | CF$_3$ | H | H | CH$_3$ | O | 329 | 2.77 |
| C-4 | 3-(ethylsulfonyl)pyridin-2-yl | CF$_3$ | H | H | CH$_3$ | O | 387 | 2.39 |

1) Analytical HPLC - Method 2

The biological activity of the compounds of formula (I) of the present invention can be evaluated in biological tests as described in the following.

If not otherwise specified, most test solutions are prepared as follow:

The active compound is dissolved at the desired concentration in a mixture of 1:1 (vol:vol) distilled water:acetone. The test solution is prepared at the day of use.

Test solutions are prepared in general at concentrations of 1000 ppm, 500 ppm, 300 ppm, 100 ppm and 30 ppm (wt/vol).

Boll Weevil (*Anthonomus gandis*)

For evaluating control of boll weevil (*Anthonomus grandis*) the test unit consisted of 96-well-microtiter plates containing an insect diet and 5-10 *A. grandis* eggs.

The compounds were formulated using a solution containing 75% v/v water and 25% v/v DMSO. Different concentrations of formulated compounds were sprayed onto the insect diet at 5 μl, using a custom built micro atomizer, at two replications.

After application, microtiter plates were incubated at about 25±1° C. and about 75±5% relative humidity for 5 days. Egg and larval mortality was then visually assessed.

In this test, compound C-1 and C-2 at 800 ppm showed over 75% mortality in comparison with untreated controls.

Tobacco Budworm (*Heliothis virescens*) (2nd Instar Larvae)

The active compounds were formulated by a Tecan liquid handler in 100% cyclohexanone as a 10,000 ppm solution supplied in tubes. The 10,000 ppm solution was serially diluted in 100% cyclohexanone to make interim solutions. These served as stock solutions for which final dilutions were made by the Tecan in 50% acetone:50% water (v/v) into 10 or 20 ml glass vials. A nonionic surfactant (Kinetic®) was included in the solution at a volume of 0.01% (v/v). The vials were then inserted into an automated electrostatic sprayer equipped with an atomizing nozzle for application to plants/insects.

Cotton plants were grown 2 plants to a pot and selected for treatment at the cotyledon stage. Test solutions were sprayed onto the foliage by an automated electrostatic plant sprayer equipped with an atomizing spray nozzle. The plants were dried in the sprayer fume hood and then removed from the sprayer. Each pot was placed into perforated plastic bags with a zip closure. About 10 to 11 budworm larvae were placed into the bag and the bags zipped closed. Test plants were maintained in a growth room at about 25° C. and about 20-40% relative humidity for 4 days, avoiding direct exposure to fluorescent light (24 hour photoperiod) to prevent trapping of heat inside the bags. Mortality and reduced feeding were assessed 4 days after treatment, compared to untreated control plants.

In this test, compound C-2 at 800 ppm showed over 75% mortality in comparison with untreated controls.

Vetch Aphid (*Megoura viciae*)

For evaluating control of vetch aphid (*Megoura viciae*) through contact or systemic means the test unit consisted of 24-well-microtiter plates containing broad bean leaf disks.

The compounds were formulated using a solution containing 75% v/v water and 25% v/v DMSO. Different concentrations of formulated compounds were sprayed onto the leaf disks at 2.5 μl, using a custom built micro atomizer, at two replications.

After application, the leaf disks were air-dried and 5-8 adult aphids placed on the leaf disks inside the microtiter plate wells. The aphids were then allowed to suck on the treated leaf disks and incubated at about 23±1° C. and about 50±5% relative humidity for 5 days. Aphid mortality and fecundity was then visually assessed.

In this test, compound C-2 and C-4 at 800 ppm showed over 75% mortality in comparison with untreated controls.

Cowpea Aphid (*Aphis craccivora*)

The active compound is dissolved at the desired concentration in a mixture of 1:1 (vol:vol) distilled water:acetone. Surfactant (Kinetic® HV) is added at a rate of 0.01% (vol/vol). The test solution is prepared at the day of use.

Potted cowpea plants were colonized with approximately 30-50 aphids of various stages by manually transferring a leaf tissue cut from infested plant 24 hours before application. Plants were sprayed with the test solutions using a DeVilbiss® hand atomizer at 20-30 psi (≈1.38 to 2.07 bar) after the pest population has been checked. Treated plants are maintained on light carts at about 25-26° C. Percent mortality was assessed after 72 hours.

In this test, compound C-2 at 300 ppm showed over 75% mortality in comparison with untreated controls.

Rice Green Leafhopper (*Nephotettix virescens*)

Four to five-week old rice seedlings with cut upper leaf portion were cleaned and washed 24 hours before spraying. The active compounds were formulated in 1:1 acetone:water (vol:vol), and 0.01% vol/vol surfactant (Kinetic® HV) was added. Potted rice seedlings were sprayed with 5-6 ml test solution, air dried, covered with Mylar cages and inoculated with 10 adults. Treated rice plants were kept at about 28-29° C. and relative humidity of about 50-60%. Percent mortality was recorded after 72 hours.

In this test, compound C-2 at 300 ppm showed over 75% mortality in comparison with untreated controls.

Rice Brown Plant Hopper (*Nilaparvata lugens*)

Four to five-week old rice seedlings were cleaned and washed 24 hours before spraying. The active compounds were formulated in 1:1 acetone:water (vol:vol) and 0.01% vol/vol surfactant (Kinetic® HV) was added. Potted rice seedlings were sprayed with 5-6 ml test solution, air dried, covered with Mylar cages and inoculated with 10 adults. Treated rice plants were kept at about 28-29° C. and relative humidity of about 50-60%. Percent mortality was recorded after 72 hours.

In this test, compound C-2 at 300 ppm showed over 75% mortality in comparison with untreated controls.

Diamond Back Moth (*Plutella xylostella*)

The active compound is dissolved at the desired concentration in a mixture of 1:1 (vol:vol) distilled water:acetone. Surfactant (Kinetic® HV) is added at a rate of 0.01% (vol/vol). The test solution is prepared at the day of use.

Leaves of cabbage were dipped in test solution and air-dried. Treated leaves were placed in petri dishes lined with moist filter paper and inoculated with ten $3^{rd}$ instar larvae. Mortality was recorded 72 hours after treatment. Feeding damages were also recorded using a scale of 0-100%.

In this test, compound C-2 and C-4 at 300 ppm showed over 75% mortality in comparison with untreated controls.

Green Peach Aphid (*Myzus persicae*) (Mixed Life Stages)

The active compounds were formulated by a Tecan liquid handler in 100% cyclohexanone as a 10,000 ppm solution supplied in tubes. The 10,000 ppm solution was serially diluted in 100% cyclohexanone to make interim solutions. These served as stock solutions for which final dilutions were made by the Tecan in 50% acetone:50% water (v/v) into 10 or 20 ml glass vials. A nonionic surfactant (Kinetic®) was included in the solution at a volume of 0.01% (v/v). The vials were then inserted into an automated electrostatic sprayer equipped with an atomizing nozzle for application to plants/insects.

Bell pepper plants at the first true-leaf stage were infested prior to treatment by placing heavily infested leaves from the main colony on top of the treatment plants. Aphids were allowed to transfer overnight to accomplish an infestation of 30-50 aphids per plant and the host leaves were removed. The infested plants were then sprayed by an automated electrostatic plant sprayer equipped with an atomizing spray nozzle. The plants were dried in the sprayer fume hood, removed, and then maintained in a growth room under fluorescent lighting in a 24-hr photoperiod at about 25° C. and about 20-40% relative humidity. Aphid mortality on the treated plants, relative to mortality on untreated control plants, was determined after 5 days.

In this test, compound C-2 at 300 ppm showed over 75% mortality in comparison with untreated controls.

Southern Armyworm (*Spodoptera eridania*), 2nd Instar Larvae

The active compounds were formulated by a Tecan liquid handler in 100% cyclohexanone as a 10,000 ppm solution supplied in tubes. The 10,000 ppm solution was serially diluted in 100% cyclohexanone to make interim solutions. These served as stock solutions for which final dilutions were made by the Tecan in 50% acetone:50% water (v/v) into 10 or 20 ml glass vials. A nonionic surfactant (Kinetic®) was included in the solution at a volume of 0.01% (v/v). The vials were then inserted into an automated electrostatic sprayer equipped with an atomizing nozzle for application to plants/insects.

Lima bean plants (variety Sieva) were grown 2 plants to a pot and selected for treatment at the 1st true leaf stage. Test solutions were sprayed onto the foliage by an automated electrostatic plant sprayer equipped with an atomizing spray nozzle. The plants were dried in the sprayer fume hood and then removed from the sprayer. Each pot was placed into perforated plastic bags with a zip closure. About 10 to 11 armyworm larvae were placed into the bag and the bags zipped closed. Test plants were maintained in a growth room at about 25° C. and about 20-40% relative humidity for 4 days, avoiding direct exposure to fluorescent light (24 hour photoperiod) to prevent trapping of heat inside the bags. Mortality and reduced feeding were assessed 4 days after treatment, compared to untreated control plants.

In this test, compound C-2 at 300 ppm showed over 75% mortality in comparison with untreated controls.

The invention claimed is:

1. A compound of formula (I) selected from the group consisting of a compound of formula (I-A) or (I-B):

(I-A)

(I-B)

wherein

X is O or S;

$R^x$, $R^y$ independently of each other are selected from the group consisting of $C_1$-$C_6$-alkyl, $C_1$-$C_6$-alkoxy, $C_2$-$C_6$-alkenyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which are unsubstituted or substituted by halogen; C(O)—$OR^a$, $NR^bR^c$, $C_1$-$C_6$-alkylen-$NR^bR^c$, O—$C_1$-$C_6$-alkylen-$NR^bR^c$, $C_1$-$C_6$-alkylen-CN, NH—$C_1$-$C_6$-alkylen-$NR^bR^c$, C(O)—$NR^bR^c$, C(O)—$R^d$, $SO_2NR^bR^c$, $S(=O)_mR^c$; phenyl and benzyl, wherein the phenyl ring is unsubstituted or substituted by radicals $R^f$;

$R^1$ is partially or fully halogenated $C_1$-$C_6$-alkyl, partially or fully halogenated $C_1$-$C_6$-alkoxy, partially or fully halogenated $C_2$-$C_6$-alkenyl, partially or fully halogenated $C_2$-$C_6$-alkynyl, partially or fully halogenated $C_3$-$C_6$-cycloalkyl, partially or fully halogenated $C_3$-$C_6$- cycloalkoxy, partially or fully halogenated $C_1$-$C_6$-sulfenyl, partially or fully halogenated $C_1$-$C_6$-sulfinyl, or partially or fully halogenated $C_1$-$C_6$-sulfonyl;

$R^2$, $R^3$, $R^4$ independently of each other are selected from the group consisting of H, halogen, $N_3$, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxyx-$C_1$-$C_4$-alkyl, which are unsubstituted or substituted by halogen, C(O)—$OR^a$, $NR^bR^c$, $C_1$-$C_6$-alkylen-$NR^bR^c$, O—$C_1$-$C_6$-alkylen-$NR^bR^c$, $C_1$-$C_6$-alkylen-CN, NH—$C_1$-$C_6$-alkylen-$NR^bR^c$, C(O)—$NR^bR^c$, C(O)—$R^d$, $SO_2NR^bR^c$ and S(=O)$_m R^e$, phenyl which is unsubstituted or substituted by radicals $R^f$, phenoxy which is unsubstituted or substituted by radicals $R^f$, phenylcarbonyl which is unsubstituted or substituted by radicals $R^f$, phenylthio which is unsubstituted or substituted by radicals $R^f$, or benzyl which is unsubstituted or substituted by radicals $R^f$;

Ar is phenyl or 5- or 6-membered heteroaryl, which are unsubstituted or substituted by radicals $R^{Ar}$, which are identical or different, wherein $R^{Ar}$ independently of each other, are selected from the group consisting of halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, which are unsubstituted or substituted by halogen, C(O)—$OR^a$, $NR^bR^c$, $C_1$-$C_6$-alkylen-$NR^bR^c$, O—$C_1$-$C_6$-alkylen-$NR^bR^c$, $C_1$-$C_6$-alkylen-CN, NH—$C_1$-$C_6$-alkylen-$NR^bR^c$, C(O)—$NR^bR^c$, C(O)—$R^d$, $SO_2NR^bR^c$ and S(=O)$_m R^e$, phenyl which is unsubstituted or substituted by radicals $R^f$, phenoxy which is unsubstituted or substituted by radicals $R^f$, phenylcarbonyl which is unsubstituted or substituted by radicals $R^f$, phenylthio which is unsubstituted or substituted by radicals $R^f$, or benzyl which is unsubstituted or substituted by radicals $R^f$;

each $R^a$ is selected from H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which are unsubstituted or substituted by halogen, $C_1$-$C_6$-alkylen-$NR^bR^c$, $C_1$-$C_6$-alkylen-CN, phenyl and benzyl, wherein the phenyl ring is unsubstituted or substituted by radicals $R^f$;

each $R^b$ is selected from H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which are unsubstituted or substituted by halogen, $C_1$-$C_6$-alkylen-CN, phenyl and benzyl, wherein the phenyl is unsubstituted or substituted by radicals $R^f$;

each $R^c$ is selected from H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which are unsubstituted or substituted by halogen, $C_1$-$C_6$-alkylen-CN, phenyl and benzyl, wherein the phenyl ring is unsubstituted or substituted by radicals $R^f$;

each moiety $NR^bR^c$ may also form an N-bound, saturated 5- to 8-membered heterocycle, which in addition to the nitrogen atom may have 1 or 2 further heteroatoms or heteroatom moieties selected from O, S(=O)$_m$ and N—R', wherein R' is H or $C_1$-$C_6$-alkyl and wherein the N-bound heterocycle is unsubstituted or substituted by radicals selected from halogen, $C_1$-$C_4$-alkyl, $C_1$-$C_4$-haloalkyl, $C_1$-$C_4$-alkoxy and $C_1$-$C_4$-haloalkoxy;

each $R^d$ is selected from H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which are unsubstituted or substituted by halogen, phenyl and benzyl, wherein the phenyl ring is unsubstituted or substituted by radicals $R^f$;

each $R^e$ is selected from $C_1$-$C_6$-alkyl, $C_3$-$C_6$-cycloalkyl, $C_3$-$C_6$-cycloalkyl-$C_1$-$C_4$-alkyl, which are unsubstituted or substituted by halogen, phenyl and benzyl, wherein the phenyl ring is unsubstituted or substituted by $R^f$;

each $R^f$ is selected from halogen, $N_3$, OH, CN, $NO_2$, SCN, $SF_5$, $C_1$-$C_6$ alkyl, $C_1$-$C_6$ alkoxy, $C_2$-$C_6$ alkenyl, $C_2$-$C_6$ alkynyl, $C_1$-$C_6$ alkoxy-$C_1$-$C_4$ alkyl, $C_1$-$C_6$ alkoxy-$C_1$-$C_4$ alkoxy, $C_3$-$C_6$ cycloalkyl, $C_3$-$C_6$ cycloalkoxy, $C_3$-$C_6$ cycloalkyl-$C_1$-$C_4$ alkyl, $C_3$-$C_6$ cycloalkoxy-$C_1$-$C_4$ alkyl, which are unsubstituted or substituted by halogen;

m is 0, 1 or 2;

and the N-oxides, stereoisomers, tautomers and agriculturally or veterinarily acceptable salts thereof.

2. The compound of formula (I-A) according to claim 1, wherein $R^x$ is selected from $C_1$-$C_3$ alkyl, $C_2$-$C_3$ alkenyl, $C_2$-$C_3$ alkynyl, $C_3$-$C_6$ cycloalkyl, and $C_1$-$C_3$ haloalkyl;

$R^1$ is selected from partially or fully halogenated $C_1$-$C_6$ alkyl, partially or fully halogenated $C_1$-$C_6$ sulfenyl, partially or fully halogenated $C_1$-$C_6$ sulfinyl, and partially or fully halogenated $C_1$-$C_6$ sulfonyl;

$R^2$ is selected from H, $CH_3$, $C_2H_5$, n-propyl, isopropyl, cyclopropyl, allyl and propargyl;

$R^4$ is selected from H, $CH_3$, $C_2H_5$, n-propyl, isopropyl, cyclopropyl, allyl and propargyl;

Ar is a phenyl or 5- or 6-membered heteroaryl substituted with $R^{Ar}$, $R^{Ar}$ is selected from halogen, $C_1$-$C_6$ alkyl, $C_1$-$C_6$ haloalkyl, $C_1$-$C_6$ alkoxy, $C_1$-$C_6$ haloalkoxy, S(=O)$_m R^e$, phenyl, phenoxy, phenylcarbonyl, phenylthio and benzyl, wherein the phenyl ring is unsubstituted or substituted by radicals $R^f$;

$R^e$ is selected from $C_1$-$C_3$ alkyl, $C_3$-$C_6$ cycloalkyl, $C_1$-$C_3$ haloalkyl, and $C_3$-$C_6$ halocycloalkyl;

$R^f$ is selected from Cl, F, Br, $OCH_3$, $OC_2H_5$, $SCH_3$, $SC_2H_5$, CN, $CH_3$, $C_2H_5$, n-propyl, isopropyl, cyclopropyl, allyl, propargyl, $CF_3$, $CHF_2$, and $CF_2CF_3$.

3. The compound of formula (I-A) according to claim 1, wherein $R^x$ is $CH_3$ or $C_2H_5$;

$R^1$ is selected from $CF_3$, $CF_2CF_3$, $CF(CF_3)_2$, $SCF_3$, $OCF_3$, $OCHF_2$, S(=O)$CF_3$, and S(=O)$_2CF_3$;

$R^2$ is selected from H, $CH_3$, and $C_2H_5$;

$R^4$ is selected from H, $CH_3$, and $C_2H_5$;

Ar is a phenyl or 5- or 6-membered heteroaryl substituted with S(=O)$_m R^e$ at the ortho position to bond connecting to 9-membered heteroaryl of compound of formula (I), and optionally further substituted with 1 or 2 $R^{Ar}$.

4. The compound of formula (I-B) according to claim 1, wherein $R^y$ is selected from $C_1$-$C_3$ alkyl, $C_2$-$C_3$ alkenyl, $C_2$-$C_3$ alkynyl, $C_3$-$C_6$ cycloalkyl, and $C_1$-$C_3$ haloalkyl;

$R^1$ is selected from partially or fully halogenated $C_1$-$C_6$ alkyl, partially or fully halogenated $C_1$-$C_6$ sulfenyl, partially or fully halogenated $C_1$-$C_6$ sulfinyl, and partially or fully halogenated $C_1$-$C_6$ sulfonyl;

$R^2$ is selected from H, $CH_3$, $C_2H_5$, n-propyl, isopropyl, cyclopropyl, allyl and propargyl;

$R^3$ is selected from H, $CH_3$, $C_2H_5$, n-propyl, isopropyl, cyclopropyl, allyl and propargyl;

Ar is a phenyl or 5- or 6-membered heteroaryl substituted with $R^{Ar}$;

$R^{Ar}$ is selected from halogen, $C_1$-$C_6$ alkyl, $C_1$-$C_6$ haloalkyl, $C_1$-$C_6$ alkoxy, $C_1$-$C_6$ haloalkoxy, $S(=O)_mR^e$, phenyl, phenoxy, phenylcarbonyl, phenylthio and benzyl, wherein the phenyl ring is unsubstituted or substituted by radicals $R^f$;

$R^e$ is selected from $C_1$-$C_3$ alkyl, $C_3$-$C_6$ cycloalkyl, $C_1$-$C_3$ haloalkyl, and $C_3$-$C_6$ halocycloalkyl;

$R^f$ is selected from Cl, F, Br, $OCH_3$, $OC_2H_5$, $SCH_3$, $SC_2H_5$, CN, $CH_3$, $C_2H_5$, n-propyl, isopropyl, cyclopropyl, allyl, propargyl, $CF_3$, $CHF_2$, and $CF_2CF_3$.

5. The compound of formula (I-B) according to claim 1, wherein $R^Y$ is $CH_3$ or $C_2H_5$;

$R^1$ is selected from $CF_3$, $CF_2CF_3$, $CF(CF_3)_2$, $SCF_3$, $OCF_3$, $OCHF_2$, $S(=O)CF_3$, and $S(=O)_2CF_3$;

$R^2$ is selected from H, $CH_3$, and $C_2H_5$;

$R^3$ is selected from H, $CH_3$, and $C_2H_5$;

Ar is a phenyl or 5- or 6-membered heteroaryl substituted with $S(=O)_mR^e$ at the ortho position to bond connecting to 9-membered heteroaryl of compound of formula (I), and optionally further substituted with 1 or 2 $R^{Ar}$.

6. The compound of formula (I) according to claim 1, wherein $R^1$ is partially or completely halogenated $C_1$-$C_2$-alkyl.

7. The compound of formula (I) according to claim 1, wherein Ar is substituted with $S(=O)_2R^e$ at the ortho-position to the bond connecting to the 9-membered heteroaryl of formula (I), and further substituted with one radical $R^{Ar}$.

8. The compound of formula (I) according to claim 7, wherein Re is $CH_2CH_3$.

9. The compound of formula (I) according to claim 1, wherein Ar is pyridyl.

10. The compound of formula (I) according to claim 1, wherein Ar is a group of formula Ar-10h:

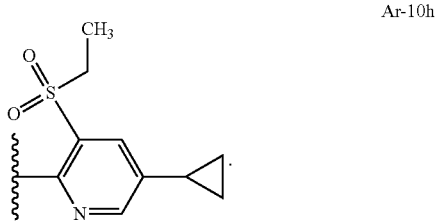 [SMILES: *c1ncc(C2CC2)cc1S(=O)(=O)CC]

Ar-10h

11. The compound of formula (I) according to claim 1, wherein $R^x$ is selected from partially or fully halogenated $C_1$-$C_3$-alkyl.

12. The compound of formula (I) according to claim 1, wherein $R^2$ is H.

13. The compound of formula (I) according to claim 1, wherein:

the compound of formula (I) is selected to be the compound of formula (I-A);

$R^x$ selected from the group consisting of $C_1$-$C_6$-alkyl, $C_1$-$C_6$-alkoxy, $C_2$-$C_6$-alkenyl, $C_2$-$C_6$-alkynyl, $C_1$-$C_4$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, which are unsubstituted or substituted by halogen; phenyl and benzyl, wherein the phenyl ring is unsubstituted or substituted by radicals $R^f$;

$R^2$ is selected from H, $CH_3$, and $C_2H_5$;

$R^4$ is selected from H, $CH_3$, and $C_2H_5$; and

Ar is a phenyl or 5- or 6-membered heteroaryl substituted with $S(=O)_mR^e$ at the ortho position to bond connecting to 9-membered heteroaryl of compound of formula (I-A), and optionally further substituted with 1 or 2 $R^{Ar}$.

14. A composition comprising the compound of formula I, as defined in claim 1, an N-oxide or an agriculturally acceptable salt thereof.

15. The composition according to claim 14, comprising additionally a further active substance.

16. A seed treated with a compound of the formula (I), as defined in claim 15, or the enantiomers, diastereomers or salts thereof, or the composition, as defined in claim 14, in an amount of from 0.1 g to 10 kg per 100 kg of seed.

17. A method for combating or controlling invertebrate pests, which method comprises contacting said pest or its food supply, habitat or breeding grounds with a pesticidally effective amount of at least one compound of the formula (I) according to claim 16 or the composition according to claim 14.

18. A method for protecting growing plants from attack or infestation by invertebrate pests, which method comprises contacting a plant, or soil or water in which the plant is growing, with a pesticidally effective amount of at least one compound of the formula (I), according to claim 1.

19. A method for protecting growing plants from attack or infestation by invertebrate pests, which method comprises contacting a plant, or soil or water in which the plant is growing, with a pesticidally effective amount of at least one compound of the formula (I), according to the composition according to claim 14.

20. A method for treating or protecting an animal from infestation or infection by invertebrate pests which comprises bringing the animal in contact with a pesticidally effective amount of at least one compound of the formula (I) as defined in claim 1, a stereoisomer thereof and/or at least one veterinarily acceptable salt thereof.

21. The method of claim 18, wherein the compound of formula (I) is the compound of formula (I-A), $R^x$ is selected from $C_1$-$C_3$ alkyl, $C_2$-$C_3$ alkenyl, $C_2$-$C_3$ alkynyl, $C_3$-$C_6$ cycloalkyl, and $C_1$-$C_3$ haloalkyl;

$R^1$ is selected from partially or fully halogenated $C_1$-$C_6$ alkyl, partially or fully halogenated $C_1$-$C_6$ sulfenyl, partially or fully halogenated $C_1$-$C_6$ sulfinyl, and partially or fully halogenated $C_1$-$C_6$ sulfonyl;

$R^2$ is selected from H, $CH_3$, $C_2H_5$, n-propyl, isopropyl, cyclopropyl, allyl and propargyl;

$R^4$ is selected from H, $CH_3$, $C_2H_5$, n-propyl, isopropyl, cyclopropyl, allyl and propargyl;

Ar is a phenyl or 5- or 6-membered heteroaryl substituted with $R^{Ar}$;

$R^{Ar}$ is selected from halogen, $C_1$-$C_6$ alkyl, $C_1$-$C_6$ haloalkyl, $C_1$-$C_6$ alkoxy, $C_1$-$C_6$ haloalkoxy, $S(=O)_mR^e$, phenyl, phenoxy, phenylcarbonyl, phenylthio and benzyl, wherein the phenyl ring is unsubstituted or substituted by radicals $R^f$, $R^e$ is selected from $C_1$-$C_3$ alkyl, $C_3$-$C_6$ cycloalkyl, $C_1$-$C_3$ haloalkyl, and $C_3$-$C_6$ halocycloalkyl;

$R^f$ is selected from Cl, F, Br, $OCH_3$, $OC_2H_5$, $SCH_3$, $SC_2H_5$, CN, $CH_3$, $C_2H_5$, n-propyl, isopropyl, cyclopropyl, allyl, propargyl, $CF_3$, $CHF_2$, and $CF_2CF_3$.

22. The method of claim 18, wherein
the compound of formula (I) is the compound of formula (I-A),
$R^x$ is $CH_3$ or $C_2H_5$;
$R^1$ is selected from $CF_3$, $CF_2CF_3$, $CF(CF_3)_2$, $SCF_3$, $OCF_3$, $OCHF_2$, $S(=O)CF_3$, and $S(=O)_2CF_3$;
$R^2$ is selected from H, $CH_3$, and $C_2H_5$;
$R^4$ is selected from H, $CH_3$, and $C_2H_5$;
Ar is a phenyl or 5- or 6-membered heteroaryl substituted with $S(=O)_m R^e$ at the ortho position to bond connecting to 9-membered heteroaryl of compound of formula (I), and optionally further substituted with 1 or 2 $R^{Ar}$.

23. The method of claim 18, wherein
the compound of formula (I) is the compound of formula (I-B),
$R^y$ is selected from $C_1$-$C_3$ alkyl, $C_2$-$C_3$ alkenyl, $C_2$-$C_3$ alkynyl, $C_3$-$C_6$ cycloalkyl, and $C_1$-$C_3$ haloalkyl;
$R^1$ is selected from partially or fully halogenated $C_1$-$C_6$ alkyl, partially or fully halogenated $C_1$-$C_6$ sulfenyl, partially or fully halogenated $C_1$-$C_6$ sulfinyl, and partially or fully halogenated $C_1$-$C_6$ sulfonyl;
$R^2$ is selected from H, $CH_3$, $C_2H_5$, n-propyl, isopropyl, cyclopropyl, allyl and propargyl;
$R^3$ is selected from H, $CH_3$, $C_2H_5$, n-propyl, isopropyl, cyclopropyl, allyl and propargyl;
Ar is a phenyl or 5- or 6-membered heteroaryl substituted with $R^{Ar}$;
$R^{Ar}$ is selected from halogen, $C_1$-$C_6$ alkyl, $C_1$-$C_6$ haloalkyl, $C_1$-$C_6$ alkoxy, $C_1$-$C_6$ haloalkoxy, $S(=O)_m R^e$, phenyl, phenoxy, phenylcarbonyl, phenylthio and benzyl, wherein the phenyl ring is unsubstituted or substituted by radicals $R^f$,
$R^e$ is selected from $C_1$-$C_3$ alkyl, $C_3$-$C_6$ cycloalkyl, $C_1$-$C_3$ haloalkyl, and $C_3$-$C_6$ halocycloalkyl;
$R^f$ is selected from Cl, F, Br, $OCH^3$, $OC_2H_5$, $SCH_3$, $SC_2H_5$, CN, $CH_3$, $C_2H_5$, n-propyl, isopropyl, cyclopropyl, allyl, propargyl, $CF_3$, $CHF_2$, and $CF_2CF_3$.

24. The method of claim 18, wherein
the compound of formula (I) is the compound of formula (I-B),
$R^Y$ is $CH_3$ or $C_2H_5$;
$R^1$ is selected from $CF_3$, $CF_2CF_3$, $CF(CF_3)_2$, $SCF_3$, $OCF_3$, $OCHF_2$, $S(=O)CF_3$, and $S(=O)_2CF_3$;
$R^2$ is selected from H, $CH_3$, and $C_2H_5$;
$R^3$ is selected from H, $CH_3$, and $C_2H_5$;
Ar is a phenyl or 5- or 6-membered heteroaryl substituted with $S(=O)_m R^e$ at the ortho position to bond connecting to 9-membered heteroaryl of compound of formula (I), and optionally further substituted with 1 or 2 $R^{Ar}$.

* * * * *